United States Patent
Higgins

(10) Patent No.: US 9,938,557 B2
(45) Date of Patent: Apr. 10, 2018

(54) RED BLOOD CELL DYNAMICS FOR ADMINISTERING TREATMENT FOR IRON-DEFICIENCY ANEMIA

(75) Inventor: John M. Higgins, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 1 day.

(21) Appl. No.: 13/823,338

(22) PCT Filed: Sep. 16, 2011

(86) PCT No.: PCT/US2011/052038
§ 371 (c)(1),
(2), (4) Date: May 28, 2013

(87) PCT Pub. No.: WO2012/037524
PCT Pub. Date: Mar. 22, 2012

(65) Prior Publication Data
US 2013/0236566 A1    Sep. 12, 2013

Related U.S. Application Data

(60) Provisional application No. 61/383,357, filed on Sep. 16, 2010.

(51) Int. Cl.
| C12Q 1/02 | (2006.01) |
| G01N 33/72 | (2006.01) |
| G01N 33/80 | (2006.01) |
| G01N 33/94 | (2006.01) |
| G01N 33/68 | (2006.01) |

(52) U.S. Cl.
CPC ........... *C12Q 1/02* (2013.01); *G01N 33/6893* (2013.01); *G01N 33/721* (2013.01); *G01N 33/80* (2013.01); *G01N 33/94* (2013.01); *G01N 2800/06* (2013.01); *G01N 2800/22* (2013.01); *G01N 2800/224* (2013.01)

(58) Field of Classification Search
None
See application file for complete search history.

(56) References Cited

U.S. PATENT DOCUMENTS

| 5,017,497 A | 5/1991 | Gerard de Grooth et al. |
| 5,266,269 A | 11/1993 | Niiyama et al. |
| 5,378,633 A | 1/1995 | von Behrens et al. |
| 5,631,165 A | 5/1997 | Chupp et al. |
| 5,812,419 A | 9/1998 | Chupp et al. |
| 6,030,838 A | 2/2000 | Telmissani |
| 6,228,652 B1 | 5/2001 | Rodriguez et al. |
| 6,320,656 B1 | 11/2001 | Ferrante et al. |
| 6,524,858 B1 | 2/2003 | Zelmanovic et al. |
| 7,324,194 B2 | 1/2008 | Roche et al. |
| 7,981,681 B2 | 7/2011 | Champseix et al. |
| 2007/0172956 A1* | 7/2007 | Magari et al. .................. 436/66 |
| 2008/0153170 A1 | 6/2008 | Garrett et al. |
| 2008/0158561 A1 | 7/2008 | Vacca et al. |
| 2008/0268494 A1 | 10/2008 | Linssen |
| 2011/0070210 A1 | 3/2011 | Andrijauskas |
| 2011/0070606 A1 | 3/2011 | Winkelman et al. |
| 2011/0077871 A1 | 3/2011 | Fukuma et al. |
| 2011/0149061 A1 | 6/2011 | Wardlaw et al. |
| 2011/0164803 A1 | 7/2011 | Wang et al. |
| 2011/0178716 A1 | 7/2011 | Krockenberger et al. |
| 2011/0190143 A1 | 8/2011 | Payen de la Garanderie et al. |
| 2013/0236566 A1 | 9/2013 | Higgins |

FOREIGN PATENT DOCUMENTS

| JP | 1995-105166 | 4/1995 |
| JP | 1999-326315 | 11/1999 |
| JP | A-H-11-326315 | 11/1999 |
| JP | A-2005-503559 | 2/2005 |
| JP | 2009-36587 | 2/2009 |
| JP | 2009-510402 | 3/2009 |
| JP | 2009-524068 | 6/2009 |
| JP | 2009-524069 | 6/2009 |
| JP | A-2009-524069 | 6/2009 |
| JP | 2010-526873 | 8/2010 |
| WO | WO 03/025583 | 3/2003 |
| WO | WO 2007/0084977 | 7/2007 |
| WO | 2011/057744 | 5/2011 |
| WO | WO 2012/037524 | 3/2012 |
| WO | WO 2014/074889 | 5/2014 |

OTHER PUBLICATIONS

Prommer, "Total Hemoglobin Mass—A New Parameter to Detect Blood Doping," Medicine & Science in Sports & Exercise, vol. 40, p. 2112-2118, 2008.*

Kleophas, "Dose tailoring strategies in haemodialysis patients: a discussion of case histories," Nephrol Dial Transplant, vol. 20 [Suppl 6], p. vi31—vi36, 2005.*

Cook, "Diagnosis and management of iron-deficiency anaemia," Best Practice & Research Clinical Haematology, vol. 18, p. 319-332, 2005.*

Lundby, "Erythropoietin treatment elevates haemoglobin concentration by increasing red cell volume and depressing plasma volume," J Physiol, vol. 578, p. 309-314, 2007.*

International Search Report and Written Opinion issued in PCT/US2011/052038 dated May 2, 2012, 11 pages.

International Preliminary Report on Patentability in International Application No. PCT/US2011/052038, dated Mar. 19, 2013, 7 pages.

(Continued)

*Primary Examiner* — G. Steven Vanni
(74) *Attorney, Agent, or Firm* — Fish & Richardson P.C.

(57) ABSTRACT

Methods for identifying patients with anemia, distinguishing thalassemia-trait anemia from iron-deficiency anemia, and identifying pre-anemic patients several weeks before anemia becomes clinically detectable. Also, methods for detecting blood doping in athletes and for optimizing therapy with erythropoiesis stimulating agents or iron supplementation. Computer-readable storage devices and systems, e.g., for use in the described methods.

5 Claims, 53 Drawing Sheets

(56) References Cited

OTHER PUBLICATIONS

D'Onofrio et al., "Simultaneous Measurement of Reticulocyte and Red-Blood-Cell Indexes in Healthy-Subjects and Patients with Microcytic Anemia," Blood, 1995, 85(3):818-823.
Gardner and Benz Jr., "Anemia of chronic diseases." In: Hoffman et al., eds. Hematology: Basic Principles and Practice. 5th ed. Philadelphia, Pa: Elsevier Churchill Livingstone; 2008:chap 37, 8 pages.
Garner et al., "Genetic influences on F cells and other hematologic variables: a twin heritability study," Blood, 2000, 95(1):342-346.
Gifford et al., "A detailed study of time-dependent changes in human red blood cells: from reticulocyte maturation to erythrocyte senescence," Br J Haematol., 2006, 135(3):395-404.
Harrington et al., "Iron Deficiency Anemia, β-Thalassemia Minor, and Anemia of Chronic Disease: A Morphologic Reappraisal," Am J Clin Pathol., Dec. 2008, 129:466-471.
Higgins and Mahadevan, "Physiological and Pathological Population Dynamics of Circulating Human Red Blood Cells," PNAS, Nov. 2010, 107(47):20587-20595.
Jelkmann and Lundby, "Blood doping and its detection," Blood, Sep. 2011, 118(9):2395-2404.
Jopang et al., "False Positive Rates of Thalassemia Screening in Rural Clinical Setting: 10-Year Experience in Thailand," Southeast Asian J Trop. Med. Public Health, 2009, 40(3):576-580.
Lang et al., "Mechanisms of suicidal erythrocyte death," Cell Physiol Biochem., 2005, 15(5):195-202.
Lew et al., "Generation of Normal Human Red-Cell Volume, Hemoglobin Content, and Membrane Area Distributions by "Birth" or Regulation," Blood, 1995, 86(1):334-341.
Lippi et al., "Stability of blood cell counts, hematologic parameters and reticulocytes indexes on the Advia A120 hematologic analyzer," J Lab. Clin. Med., 2005, 146(6):333-340.
Milbrandt et al., "Predicting late anemia in critical illness," Crit. Care, 2006, 10(1), 8 pages.
Ntaios et al., "Discrimination indices as screening tests for beta-thalassemic Trait," Ann. Hematol., 2007, 86(7):487-491.
Rockey and Cello, "Evaluation of the Gastrointestinal Tract in Patients With Iron-Deficiency Anemia," New Engl J Med., Dec. 1992, 329(23):1691-1695.
Segura et al., "Current strategic approaches for the detection of blood doping practices," Forensic Sci Int., 2011, 42-48.
Sens and Gov, "Force balance and membrane shedding at the red blood-cell surface," Phys Rev Lett., 2007, 98(018102):1-4.
Waugh et al., "Rheologic properties of senescent erythrocytes: loss of surface area and volume with red blood cell age," Blood, 1992, 79(5):1351-1358.
Willekens et al., "Hemoglobin loss from erythrocytes in vivo results from spleen-facilitated vesiculation," Blood, 2003, 101(2):747-751.
Willekens et al., "Liver Kupffer cells rapidly remove red blood cell-derived vesicles from the circulation by scavenger receptors," Blood, 2005, 105(5):2141-2145.
Zenker et al., "From inverse problems in mathematical physiology to quantitative differential diagnoses," PLoS Comput. Biol., 2007, 3(11):2072-2086.
Supplementary European Search Report issued in EP 11826059 dated Feb. 21, 2014 (.
Office Action issued in JP2013-529382 dated May 26, 2015 (6 pages).
European Office Action in European Application No. 11826059, dated Jan. 29, 2016, 8 pages.
Israeli Office Action in Israel Application No. 225275, dated Dec. 13, 2015, 7 pages (with English translation).
"How to read complete blood count," JIM, 2006, 16: 792-795 (with English abstract).
Japanese Office Action in Japanese Application No. 2015-189343, dated Sep. 6, 2016, 15 pages (with English translation).
Kitcharoen et al., "A New Screening Program for Thalassemias in Thailand Based on the Complete Blood Count," Medical Online, 1994, 17: 178-183.
Yunoki et al., "MCH is useful for early diagnosis of thalassemia," 2003, 44: 771 PS-1-169 (with English Abstract).
Allen et al., "Validation and Potential 10 Mechanisms of Red Cell Distribution Width as a Prognostic Marker in Heart Failure," J Card Fail, Mar. 2010, 16:230-238.
Anderson et al, "Usefulness of a complete blood count-derived risk score to predict incident mortality in patients with suspected cardiovascular disease," Am J Cardiol, 2007, 99: 169-174.
Beutler and Waalen, "The definition of anemia: what is the lower limit of normal of the blood hemoglobin concentration?," Blood, 2006, 107: 1747-1750.
Bunn et al., "The glycosylation of hemoglobin: relevance to diabetes mellitus," Science, Apr. 1978, 200:21-27.
Cohen et al, "Red cell life span heterogeneity in hematologically normal people is sufficient to alter HbA1 c," Blood, Nov. 2008, 112:4284-4291.
Engstrom et al, "Red cell distribution width, haemoglobin A1e and incidence of diabetes mellitus," Journal of Internal Medicine, Aug. 2014, 276: 174-183.
Felker et al, "Red cell distribution width as a novel prognostic marker in heart failure—Data from the CHARM program and the Duke Databank," J Am Coll Cardiol, 2007, 50:40-47.
Franco et al., "Changes in the properties of normal human red blood cells during in vivo aging," Am J Hematol, Jan. 2013, 88:44-51.
Franco, "The measurement and importance of red cell survival," Am J Hematol, Feb. 2009, 84:109-114.
Gram-Hansen et al, "Glycosylated Hemoglobin (HbA1c) as an Index of the Age of the Erythrocyte Population in NonDiabetic Patients," Eur J Haematol, 1990, 44:201-203.
Horne, "A Changing Focus on the Red Cell Distribution Width: Why Does It Predict Mortality and Other Adverse Medical Outcomes?," Cardiology, 2012, 122:213-215.
Horne, "The Red Cell Distribution Width: What Is Its Value for Risk Prognostication and for Understanding Disease Pathophysiology?," Cardiology, 2011, 119:140-141.
International Preliminary Report on Patentability in International Application No. PCT/US2015/034508, dated Dec. 6, 2016, 9 pages.
International Search Report and Written Opinion in International Application No. PCT/US2016/066860, dated Mar. 2, 2017, 12 pages.
International Search Report and Written Opinion dated Aug. 27, 2015 in International application No. PCT/US2015/034508, 13 pages.
Jansen et al, "Determinants ofHbA1c in nondiabetic Dutch adults: genetic loci and clinical and lifestyle parameters, and their interactions in the lifelines cohort study," Journal of Internal Medicine, 2013, 273:283-293.
Ladyzynski et al, "Hemoglobin Glycation Rate Constant in Nondiabetic Individuals," Ann Biomed Eng, 2011, 39:2721-2734.
Ladyzynski et al, "Validation of hemoglobin glycation models using glycemia monitoring in vivo and culturing of erythrocytes in vitro," Ann Biomed Eng, 2008, 36: 1188-1202.
Leslie and Cohen, "Biologic variability in plasma glucose, hemoglobin A1e, and advanced glycation end products associated with diabetes complications," Journal of Diabetes Science and Technology, Jul. 2009, 3:635-643.
Lozoff et al., "Long-Term Developmental Outcome of Infants with Iron-Deficiency," N Engl J Med, Sep. 1991, 325:687-694.
Mock et al., "Measurement of Posttransfusion Red Cell Survival With the Biotin Label," Transf Med Rev, Jul. 2014, 28: 114-125.
Office Action in Israeli Application No. 225275, dated Jan. 8, 2017, 4 pages, with English translation.
Pascual-Figal et al., "Red blood cell distribution width predicts new-onset anemia in heart failure patients," Int J Cardiol, 2012, 160: 196-200.
Patel et al., "Red Blood Cell Distribution Width and the Risk of Death in Middle-aged and Older Adults," Arch Intern Med, Mar. 2009, 169:515-523.
Perlstein et al., "Red Blood Cell Distribution 30 Width and Mortality Risk in a Community-Based Prospective Cohort," Arch Intern Med, Mar. 2009, 169:588-594.

(56) References Cited

OTHER PUBLICATIONS

Piva et al., "Automated reticulocyte counting: state of the art and clinical applications in the evaluation of erythropoiesis," Clinical Chemistry and Laboratory Medicine, Oct. 2010, 48:1369-1380.
Spell et al., "The value of a complete blood 5 count in predicting cancer of the colon," Cancer Detect Prev, 2004, 28:37-42.
Veeranna et al., "The Association of Red Cell Distribution Width with Glycated Hemoglobin among Healthy Adults without Diabetes Mellitus," Cardiology, 2012, 122:129-132.
Willekens et al., "Erythrocyte vesiculation: a self-protective mechanism?," Br J Haematol, Apr. 2008, 141:549-556.
European Search Report in Application No. 17160811.1, dated Sep. 25, 2017, 18 pages.
Mosior et al., "Critical cell volume and shape of bovine erythrocytes," General Physiology and Biophysics, Oct. 1992, 499-506.
Pande et al., "The sweep constant concept in phase coarsening," Metallurgical and Materials Transactions, Sep. 1998, 29: 2395-2398.
Eliaz et al., "Modeling failure of metallic glasses due to hydrogen embrittlement in the absence of external loads," Acta Materialia, Jan. 2004, 52: 93-105.
European Search Report in Application No. 17160801.1, dated Jan. 16, 2018, 14 pages.

\* cited by examiner

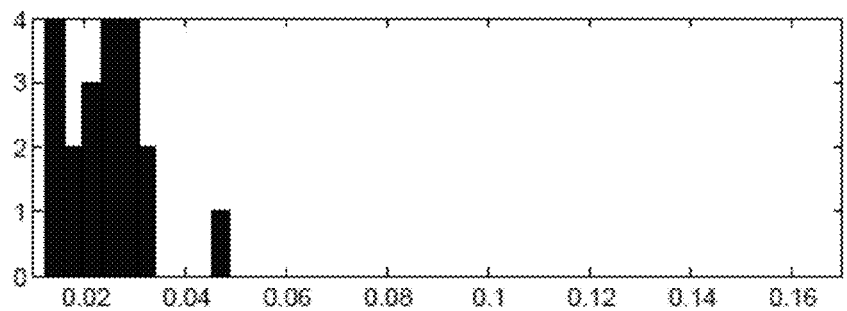
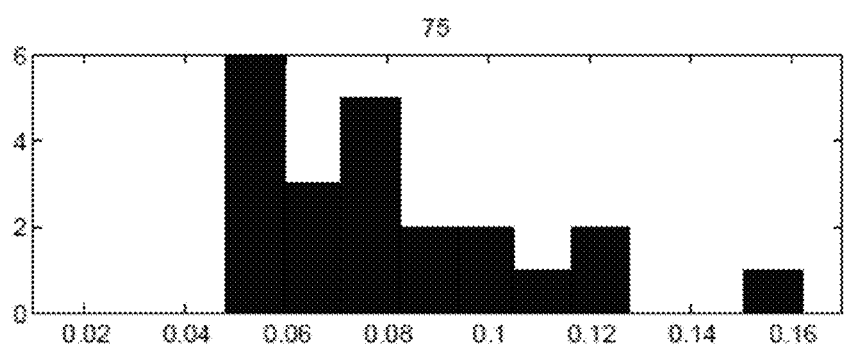
FIG. 8C
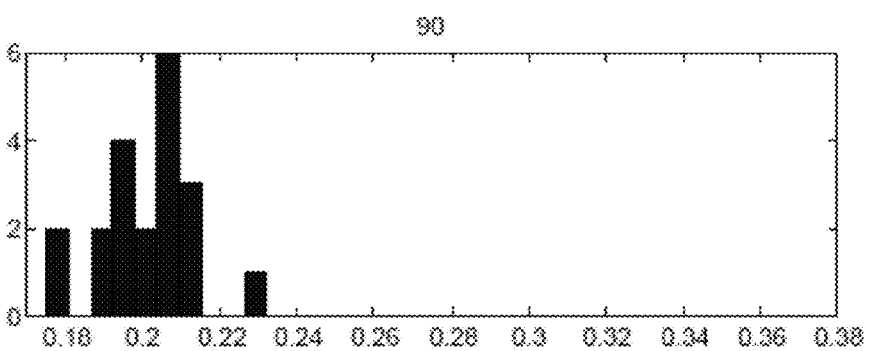
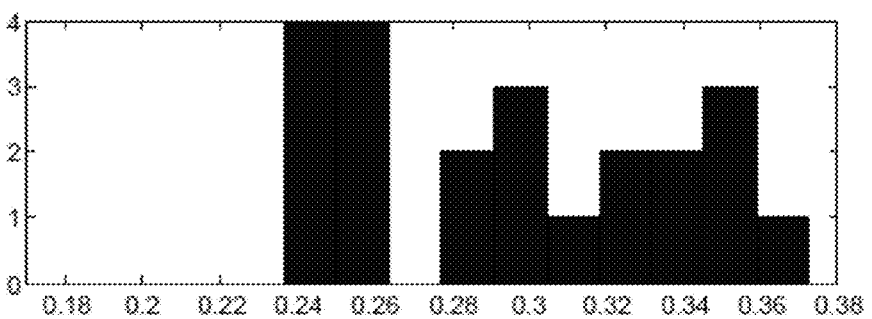
FIG. 8D

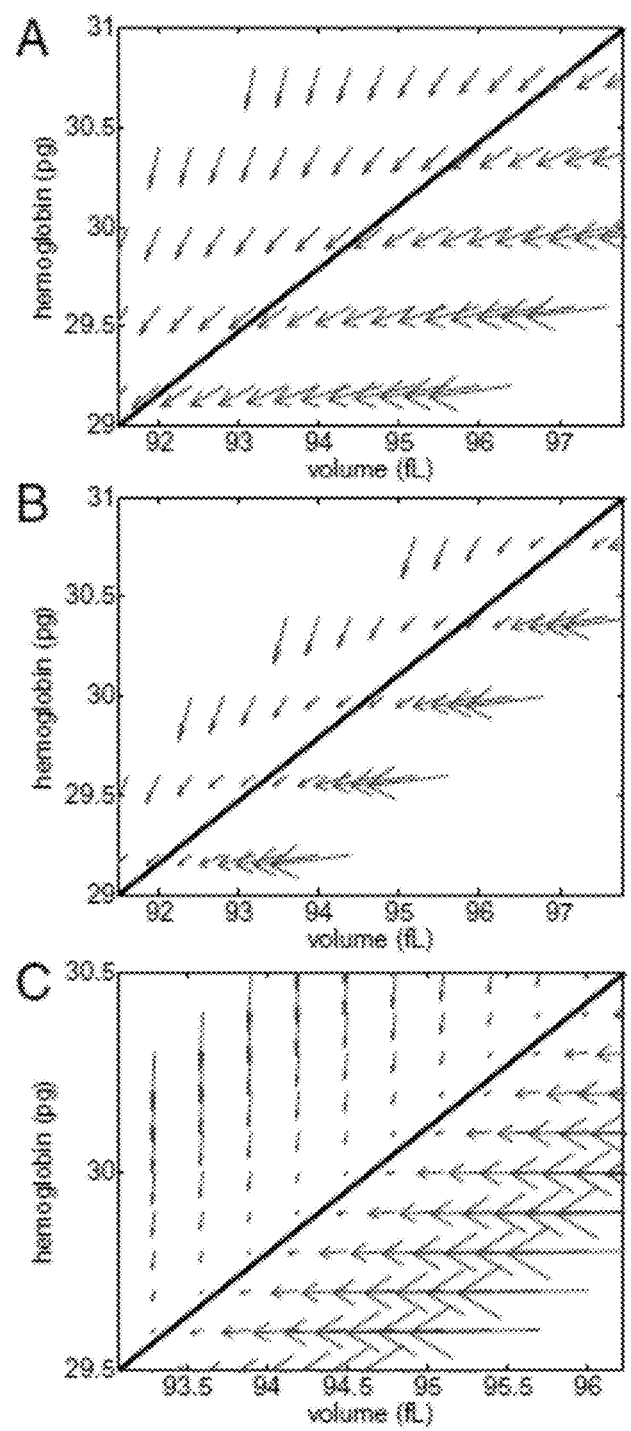
FIGs. 9A-C

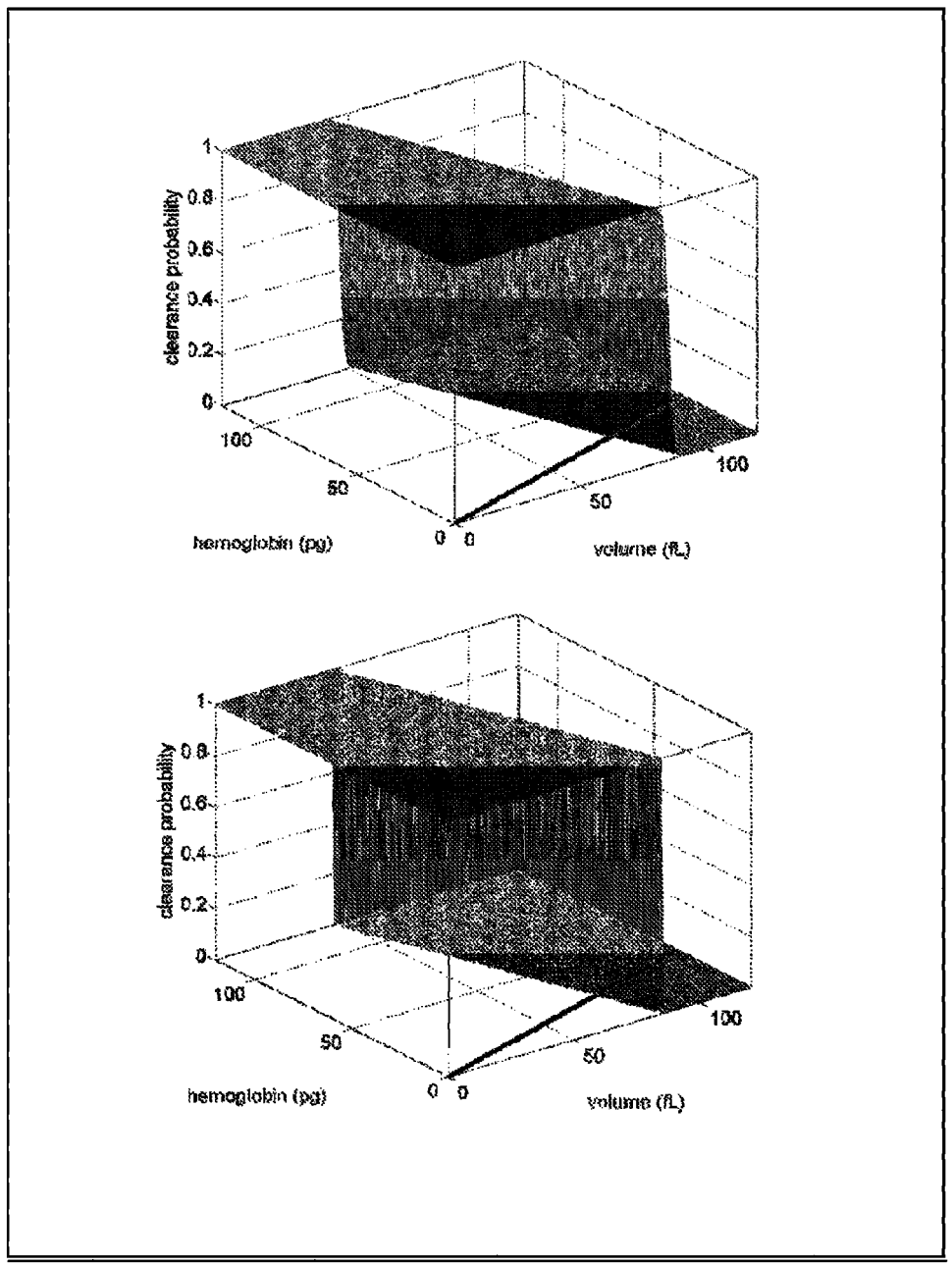
FIGs. 10A-B

```
function r = modelSample(sAccession, bDB, bParallel, vSimID, nStartingPoints,
vMuAge)
    % Given an accession, calculate optimal model parameters and store
    % them.
    r = 0;
    if (nargin == 1)
        bDB = 1;
        bParallel = 0;
        vSimID = [72];
        nStartingPoints = 10;
        vMuAge = [50 25 40 60 75];
    end
    rand('twister', sum(100*clock));

% If running in parallel with more than 1 starting point, try to
    % execute all starting points in parallel at the same time.
    if (bParallel)
        if (nStartingPoints > 1)
            jm = findResource('scheduler','type','lsf');
            set(jm,'ClusterMatlabRoot','/opt/matlab');
            set(jm, 'SubmitArguments', '-q all_12h');
            job=createJob(jm);
        else if (~matlabpool('size'))
                matlabpool local
            end
        end
    end % And for each set of simulation parameters.
    stSimulationParameters = getSimulationParameters(bDB, '7/01/09', vSimID);

% Get the steady state values for this accession.
    stSteadyState = getSteadyState(bDB, sAccession, '7/01/09',
stSimulationParameters);
%return
    % For each starting point.
    stStartingPoints = getStartingPoints(bDB, '7/01/09', stSimulationParameters,
nStartingPoints);

for ixSimParams = 1:length(stSimulationParameters)
        for ixMuAge = 1:length(vMuAge)
            stSteadyState.muAge = vMuAge(ixMuAge);
            vStart = randperm([length(stStartingPoints)]);
            for (ixStart = 1:length(vStart))
                if (bParallel && (nStartingPoints > 1))
                    csInputs = {stSteadyState; stStartingPoints(vStart(ixStart));
stSimulationParameters(ixSimParams); bDB; sAccession; bParallel};
                    createTask(job, @findOptimalParams, 1, csInputs);
                else
                    % Find the optimal parameters.
                    stParameters = findOptimalParams(stSteadyState,
stStartingPoints(vStart(ixStart)), stSimulationParameters(ixSimParams), bDB,
sAccession, bParallel);
                end
            end
        end
    end
    if (bParallel && (nStartingPoints > 1))
        submit(job);
```

FIG. 15A

```
    end
end function stSteadyState = getSteadyState(bDB, sAccession, sDate,
stSimulationParameters)
    stSteadyState = [];
    if (bDB)
        stSteadyState = queryFCSSteadyState(sAccession, sDate,
stSimulationParameters(1).nSteadyStateVersion);
        %return
    else
        stSteadyState = readFCSSteadyState(sAccession, sDate,
stSimulationParameters(1).nSteadyStateVersion);
    end assert(~any([diff([stSimulationParameters(:).nMinV])
diff([stSimulationParameters(:).nMeshWidth])
diff([stSimulationParameters(:).nMaxV])])); 
    assert(~any([diff([stSimulationParameters(:).nMinH])
diff([stSimulationParameters(:).nMeshWidth])
diff([stSimulationParameters(:).nMaxH])]));

[V,H] =
meshgrid([stSimulationParameters(1).nMinV:stSimulationParameters(1).nMeshWidth:st
SimulationParameters(1).nMaxV], ...

[stSimulationParameters(1).nMinH:stSimulationParameters(1).nMeshWidth:stSimulatio
nParameters(1).nMaxH]);
    H = flipud(H);
    vEmpirical = strcmp({stSimulationParameters(:).sInitialDistribution}',
'Empirical');
    bEmpirical = all(vEmpirical);
    if (bEmpirical)
        [Phat, P, vi, hi] = makeEmpiricalPDF(stSteadyState.rVData,
stSteadyState.rHCData);
        P_0 = interp2(vi, hi, Phat, V, H, 'linear', 0);
    else
        sdV = (stSteadyState.rMCV*stSteadyState.rRDW);
        sdH = (stSteadyState.rHDW*stSteadyState.rMCH);
        nCovar = stSteadyState.rRho*sdV*sdH;
        mSigma = [sdV^2 nCovar; nCovar sdH^2];
        P_0 = mvnpdf([V(:) H(:)], [stSteadyState.rMCV stSteadyState.rMCH],
mSigma);

sdV = (stSteadyState.stAdviaFile.MCV*stSteadyState.stAdviaFile.rRDW);
        sdH = (stSteadyState.stAdviaFile.HDW*stSteadyState.stAdviaFile.MCH);
        nCovar = stSteadyState.rho*sdV*sdH;
        mSigma = [sdV^2 nCovar; nCovar sdH^2];
        [vData] = mvnrnd([stSteadyState.stAdviaFile.MCV
stSteadyState.stAdviaFile.MCH], mSigma, numel(stSteadyState.vData));
        stSteadyState.vData = vData(:,1);
        stSteadyState.hcData = 100*vData(:,2)./vData(:,1);
    end
    P_0 = P_0(:)/sum(P_0(:));
    stSteadyState.P_0 = P_0;
end function stSteadyState = readFCSSteadyState(sAccession, sDate, nVersion)
    if (nargin < 3)
        nVersion = 0;
    end
```

FIG. 15B

```
% Read the sample XLS file to get the Advia File ID.
[num, txt, raw] = xlsread('sample.xls');
ixRow = find(num(:,2) == str2num(sAccession));
idAdvia = num(ixRow, 1);

% Read the advia file XLS file to get the FCS location and the steady
% state measurements.
%[num, txt, raw] = xlsread('advia.xls');
%save('advia.mat','num','txt','raw');
load('advia.mat');
nOffset = size(txt, 1) - size(num, 1);
ixRow = find(num(:,2) == idAdvia, 1, 'last');
stAdviaFile.ID = num(ixRow, 1);
stAdviaFile.RawDataFile = txt{ixRow + nOffset, 3};
stAdviaFile.MasterFCSFile = txt{ixRow + nOffset, 4};
stAdviaFile.RBCFCSFile = txt{ixRow + nOffset, 5};
stAdviaFile.ReticFCSFile = txt{ixRow + nOffset, 6};
stAdviaFile.HCT = num(ixRow, 7);
stAdviaFile.MCV = num(ixRow, 8);
stAdviaFile.RDW = num(ixRow, 9);
stAdviaFile.MCH = num(ixRow, 10);
stAdviaFile.HDW = num(ixRow, 11);
stAdviaFile.rMCV = num(ixRow, 12);
stAdviaFile.rPDW = num(ixRow, 13);
stAdviaFile.rMCH = num(ixRow, 14);
stAdviaFile.rHDW = num(ixRow, 15);
stAdviaFile.rFraction = num(ixRow, 16);

% Read the calculated steady state information.
% [num, txt, raw] = xlsread('steadystate.xls');
% save('steadystate.mat','num','txt','raw');
load('steadystate.mat');
ixRow = find(num(:,3) == stAdviaFile.ID);

if (isfinite(nVersion))
    ixID = find(num(ixRow, 15) == nVersion, 1, 'last');
    num = num(ixRow(ixID), :);
    nOffset = size(txt, 1) - size(num, 1);
    ixRow = 1;
else
    ixRow = ixRow(end);
end tSteadyState.ID = num(ixRow, 1);
tSteadyState.nDate = num(ixRow, 2);
tSteadyState.MCV = num(ixRow, 4);
tSteadyState.RDW = num(ixRow, 5);
tSteadyState.MCH = num(ixRow, 6);
tSteadyState.HDW = num(ixRow, 7);
tSteadyState.rho = num(ixRow, 8);
tSteadyState.rFraction = num(ixRow, 9);
tSteadyState.rMCV = num(ixRow, 10);
tSteadyState.rRDW = num(ixRow, 11);
tSteadyState.rMCH = num(ixRow, 12);
tSteadyState.rHDW = num(ixRow, 13);
tSteadyState.rRho = num(ixRow, 14);
tSteadyState.nSteadyStateVersion = num(ixRow, 15);
if (isnan(tSteadyState.nSteadyStateVersion))
    tSteadyState.nSteadyStateVersion = 0;
end stAdviaFile = expandFCSFilenames(stAdviaFile);
```

FIG. 15C

```
    stAdviaFile.RBCFCSFile = mapFileName(stAdviaFile.RBCFCSFile);
    stAdviaFile.ReticFCSFile = mapFileName(stAdviaFile.ReticFCSFile);
    stAdviaFile.RawDataFile = mapFileName(stAdviaFile.RawDataFile);
    [nMCV, nRDW, nCHCM, nHDW, nRho, tSteadyState.vData, tSteadyState.hcData] =
getRBCPDF(stAdviaFile, tSteadyState.nSteadyStateVersion);
    [f, nMCV, nRDW, nMCH, nHDW, nRho, tSteadyState.rVData, tSteadyState.rHCData]
= getReticPDF(stAdviaFile,
tSteadyState.nSteadyStateVersion);
    tSteadyState.stAdviaFile = stAdviaFile;

stSteadyState = tSteadyState;
end function sNewName = mapFileName(sName)
    if (~exist('Z:\Research\Microcytosis'))
        if (~ispc())
            if (~isempty(sName))
                if (sName(1) ~= '\')
                    sName = ['~/research/Microcytosis/' sName];
                end
            end
            sNewName = strrep(sName, 'Z:\Research\Microcytosis',
'~/research/Microcytosis');
            sNewName = strrep(sName, 'C:\local\jhiggins\research\microcytosis',
'~/research/Microcytosis');
            sNewName = strrep(sNewName, '\', '/');
        else
            sNewName = strrep(sName, 'Z:\Research\Microcytosis', '.');
            if ((sName(1) ~= '\'))

end
            sNewName = strrep(sNewName, '/', '\');
        end
    else
        sNewName = sName;
    end
end function stStartingPoints = getStartingPoints(bDB, sDate, stSimulationParameters,
nStartingPoints)
    bLatinHypercube = 1;
    if (bLatinHypercube)
        stStartingPoints = sampleLatinHypercube(stSimulationParameters,
nStartingPoints);
    else
        if (bDB)
            stStartingPoints = queryStartingPoints(sDate);
        else
            stStartingPoints = readStartingPoints(sDate);
        end
    end
end function stStartingPoints = readStartingPoints(sDate)
    % Read the starting point XLS file to get all possible starting points.
    [num, txt, raw] = xlsread('startingpoint.xls');

stStartingPoints = [];
    for ixStart = 1:size(num, 2)
        nDate = num(ixStart, 2);
        tStartingPoint.ID = num(ixStart, 1);
        tStartingPoint.nDate = nDate;
```

FIG. 15D

```
        tStartingPoint.alpha = num(ixStart, 3);
        tStartingPoint.betav = num(ixStart, 4);
        tStartingPoint.betah = num(ixStart, 5);
        tStartingPoint.Dv = num(ixStart, 6);
        tStartingPoint.Dh = num(ixStart, 7);
        tStartingPoint.v50 = num(ixStart, 8);
        stStartingPoints = [stStartingPoints; tStartingPoint];
    end
end function stStartingPointsLatin = sampleLatinHypercube(stSimulationParameters,
nStartingPoints)
    nDims = 6;
    nPoints = nStartingPoints;
    stStartingPointsLatin = [];

vStartingPointsNarrow =
strcmp({stSimulationParameters(:).sStartPointMethod}', 'Narrow');
    bNarrow = all(vStartingPointsNarrow);

vExponential = strcmp({stSimulationParameters(:).sFunctionalForm}',
'Exponential');
    bExponential = all(vExponential);
    vHybrid = strcmp({stSimulationParameters(:).sFunctionalForm}', 'Hybrid');
    bHybrid = all(vHybrid);
    vSimple = strcmp({stSimulationParameters(:).sFunctionalForm}', 'Simple');
    bSimple = all(vSimple);
    vAdditiveExponential = strcmp({stSimulationParameters(:).sFunctionalForm}',
'Additive Exponential');
    bAdditiveExponential = all(vAdditiveExponential);
    vDecayingAdditiveExponential =
strcmp({stSimulationParameters(:).sFunctionalForm}', 'Decaying Additive
Exponential');
    bDecayingAdditiveExponential = all(vDecayingAdditiveExponential);

if (bHybrid)
        if (~bNarrow)
            vRangeAlpha = [0 0.1];
            vRangeBetaV = [0 50];
            vRangeBetaH = [0 50];
            vRangeDV = [0 50];
            vRangeDH = [0 50];
            vRangeV50 = [0 95];
        else
            vRangeAlpha = [0 0.05];
            vRangeBetaV = [0 30];
            vRangeBetaH = [0 30];
            vRangeDV = [0 10];
            vRangeDH = [0 10];
            vRangeV50 = [50 95];
        end
    elseif (bSimple || bExponential || bAdditiveExponential ||
bDecayingAdditiveExponential)
        vRangeAlpha = [0 0.05];
        vRangeBetaV = [0 500];
        vRangeBetaH = [0 500];
        vRangeDV = [0 50];
        vRangeDH = [0 50];
        vRangeV50 = [50 95];
    end mIX = lhsdesign(nPoints, nDims);
```

FIG. 15E

```
    for ix = 1:nPoints
        tStartingPoint.ID = -1;
        tStartingPoint.nDate = datenum(now);
        tStartingPoint.alpha = vRangeAlpha(1) + range(vRangeAlpha)*mIX(ix, 1);
        tStartingPoint.betav = vRangeBetaV(1) + range(vRangeBetaV)*mIX(ix, 2);
        tStartingPoint.betah = vRangeBetaH(1) + range(vRangeBetaH)*mIX(ix, 3);
        tStartingPoint.Dv = vRangeDV(1) + range(vRangeDV)*mIX(ix, 4);
        tStartingPoint.Dh = vRangeDH(1) + range(vRangeDH)*mIX(ix, 5);
        tStartingPoint.v50 = vRangeV50(1) + range(vRangeV50)*mIX(ix, 6);
        stStartingPointsLatin = [stStartingPointsLatin; tStartingPoint];
    end
end function stStartingPoints = adjustStartingPoints(stStartingPoints)
    vRangeAlpha = range([stStartingPoints.alpha]);
    vRangeBetaV = range([stStartingPoints.betav]);
    vRangeBetaH = range([stStartingPoints.betah]);
    vRangeDV = range([stStartingPoints.Dv]);
    vRangeDH = range([stStartingPoints.Dh]);
    vRangeV50 = range([stStartingPoints.v50]);

for ix = 1:length(stStartingPoints)
        stStartingPoints(ix).alpha =
bumpStartingPoint(stStartingPoints(ix).alpha, vRangeAlpha);
        stStartingPoints(ix).betav =
bumpStartingPoint(stStartingPoints(ix).betav, vRangeBetaV);
        stStartingPoints(ix).betah =
bumpStartingPoint(stStartingPoints(ix).betah, vRangeBetaH);
        stStartingPoints(ix).Dv = bumpStartingPoint(stStartingPoints(ix).Dv,
vRangeDV);
        stStartingPoints(ix).Dh = bumpStartingPoint(stStartingPoints(ix).Dh,
vRangeDH);
        stStartingPoints(ix).v50 = bumpStartingPoint(stStartingPoints(ix).v50,
vRangeV50);
    end
end function nStartingPoint = bumpStartingPoint(nStartingPoint, nRange)
    nBump = 0.01;
    if (nStartingPoint)
        nStartingPoint = nStartingPoint - nBump*nRange;
    else
        nStartingPoint = nStartingPoint + nBump*nRange;
    end
end function stParameters = storeModelParams(bDB, sAccession, stParameters,
stSteadyState, stStartingPoint, stSimulationParameters)
    if (~isfield(stParameters.output, 'firstorderopt'))
        stParameters.output.firstorderopt = -1;
    end nDate = now;
    sDate = datestr(nDate, 'mm/dd/yyyy HH:MM:SS PM');
    colNamesStart = {'DateEntered', 'alpha', 'beta_v', 'beta_h', 'Dv', 'Dh',
'v50'};
    newDataStart = {sDate, stStartingPoint.alpha, stStartingPoint.betav,
stStartingPoint.betah, ...
        stStartingPoint.Dv, stStartingPoint.Dh,
100*stStartingPoint.v50/stSteadyState.MCV};
```

FIG. 15F

```
if (bDB)
    sODBC = 'microcytosis';
    r = [];
    conn = database(sODBC, '', '');

% Insert the starting point if necessary.
    if (stStartingPoint.ID == -1)
        fastinsert(conn, 'StartingPoint', colNamesStart, newDataStart);
        commit(conn);

curs = exec(conn, ['select max(ID) from StartingPoint']);
        curs = fetch(curs);
        nStartingPointID = curs.Data;
        stStartingPoint.ID = cell2mat(nStartingPointID);

close(curs);
    end
end

% Insert the best fit model parameters.
colNames = {'"Steady State Parameters"', '"Simulation Parameters"',
'"Starting Point"', 'DateEntered', ...
    'rho', 'MCV', 'RDW', 'MCH', 'HDW', ...
    'muAge', 'alphaV', 'alphaH', ...
    'betaV', 'betaH', 'v50', 'Dv', 'Dh', ...
    '"alphaV~"', '"alphaH~"', ...
    '"Dv~"', '"Dh~"', ...
    'Nu', 'chi2', 'df', '"first order optimality"', 'nSlope', 'alphaDecay'};
if (~isfield(stParameters, 'sOptimalTrend'))
    stParameters.sOptimalTrend = [];
end
if (strcmp(stParameters.sOptimalTrend, 'Quasi-linear'))
    newData = {stSteadyState.ID, stSimulationParameters.ID,
stStartingPoint.ID, datestr(now), ...
        stParameters.r, stParameters.mcv, stParameters.rdw, stParameters.mch,
stParameters.hdw, ...
        stParameters.muAge, stParameters.x(1), stParameters.x(7), ...
        stParameters.x(2), stParameters.x(3), stParameters.x(4),
stParameters.x(5), stParameters.x(6), ...
        stParameters.x(1)*stParameters.muAge,
stParameters.x(7)*stParameters.muAge, ...
        stParameters.x(5)*stParameters.muAge/stParameters.mcv^2,
stParameters.x(6)*stParameters.muAge/stParameters.mch^2, ...
        stParameters.x(4)/stParameters.mcv, stParameters.resnorm,
stParameters.df, stParameters.output.firstorderopt, stParameters.nSlope,
stParameters.alphaDecay};
else
    newData = {stSteadyState.ID, stSimulationParameters.ID,
stStartingPoint.ID, datestr(now), ...
        stParameters.r, stParameters.mcv, stParameters.rdw, stParameters.mch,
stParameters.hdw, ...
        stParameters.muAge, stParameters.x(1), stParameters.x(1), ...
        stParameters.x(2), stParameters.x(3), stParameters.x(4),
stParameters.x(5), stParameters.x(6), ...
        stParameters.x(1)*stParameters.muAge,
stParameters.x(1)*stParameters.muAge, ...
        stParameters.x(5)*stParameters.muAge/stParameters.mcv^2,
stParameters.x(6)*stParameters.muAge/stParameters.mch^2, ...
        stParameters.x(4)/stParameters.mcv, stParameters.resnorm,
stParameters.df, stParameters.output.firstorderopt, stParameters.nSlope,
stParameters.alphaDecay};
end
```

FIG. 15G

```
    if (bDB)
        fastinsert(conn, 'ModelParameters', colNames, newData);
        close(conn);
    else
        newDataStart{1} = datenum(newDataStart{1});
        newData{4} = datenum(newData{4});
        t = cell2mat([newDataStart, newData]);
        sTimestamp = [datestr(now, 'yyyymmdd') '.' datestr(now,'HHMMSS')];
        dlmwrite([sAccession '.' sTimestamp '.txt'], t, '-append', 'precision',
10);
    end
end function stParameters = findOptimalParams(stSteadyState,
stStartingPoint, stSimulationParameters, bDB, sAccession, bParallel)
    stParameters = getRBCPDFParameters();

stParameters.nMeshWidth = stSimulationParameters.nMeshWidth;
    stParameters.nMinVolume = stSimulationParameters.nMinV;
    stParameters.nMaxVolume = stSimulationParameters.nMaxV;
    stParameters.nMinHb = stSimulationParameters.nMinH;
    stParameters.nMaxHb = stSimulationParameters.nMaxH;
    [V,H] =
meshgrid([stParameters.nMinVolume:stParameters.nMeshWidth:stParameters.nMaxVolume
], ...
        [stParameters.nMinHb:stParameters.nMeshWidth:stParameters.nMaxHb]);
    H = flipud(H);
    stParameters.V = V;
    stParameters.H = H;

vEmpirical = strcmp({stSimulationParameters(:).sInitialDistribution}',
'Empirical');
    bEmpirical = all(vEmpirical);
    if (bEmpirical)
        stParameters.nMeanMarrowVolume = stSteadyState.rMCV;
        stParameters.nCVMarrowVolume = stSteadyState.rRDW;
        stParameters.nMeanMarrowHb = stSteadyState.rMCH;
        stParameters.nCVMarrowHb = stSteadyState.rHDW;
        stParameters.vStar = stSteadyState.MCV;
        stParameters.hStar = stSteadyState.MCH;
    else
        stParameters.nMeanMarrowVolume = stSteadyState.stAdviaFile.rMCV;
        stParameters.nCVMarrowVolume = stSteadyState.stAdviaFile.rRDW;
        stParameters.nMeanMarrowHb = stSteadyState.stAdviaFile.rMCH;
        stParameters.nCVMarrowHb = stSteadyState.stAdviaFile.rHDW;
        stParameters.vStar = stSteadyState.stAdviaFile.MCV;
        stParameters.hStar = stSteadyState.stAdviaFile.MCH;
    end stParameters.P_0 = stSteadyState.P_0;

stParameters.nMarrowRho = stSteadyState.rRho;
    stParameters.muAgeTarg = stSteadyState.muAge;

stParameters.alphav = stStartingPoint.alpha;
    stParameters.alphah = stStartingPoint.alpha;
    stParameters.betav = stStartingPoint.betav;
    stParameters.betah = stStartingPoint.betah;
    stParameters.v50 = stSteadyState.MCV*stStartingPoint.v50/100;
    stParameters.Dv = stStartingPoint.Dv;
    stParameters.Dh = stStartingPoint.Dh;
```

FIG. 15H

```
    stParameters.nSlope = 1;
    stParameters.alphaDecay = 6;

stParameters.bParallel = bParallel;
    stParameters.sOptimizer = stSimulationParameters.sOptimizer;
    stParameters.sFunctionalForm = stSimulationParameters.sFunctionalForm;
    stParameters.nMinAlpha = stSimulationParameters.nMinAlpha;
    stParameters.nMaxAlpha = stSimulationParameters.nMaxAlpha;
    stParameters.sDeathFunction = stSimulationParameters.sDeathFunction;
    stParameters.sOptimalTrend = stSimulationParameters.sOptimalTrend;
    stParameters.oQuasiLinearFit = getQuasiLinearFit(stParameters,
stSteadyState.vData, stSteadyState.hcData);
    stParameters.bPenalizeFalsePositives =
stSimulationParameters.bPenalizeFalsePositives;

[x, resnorm, output, jacobian, stParameters] = optFDPDF(stSteadyState.vData,
stSteadyState.hcData, stParameters);
    stParameters.x = x;
    stParameters.output = output;
    stParameters.resnorm = resnorm;

% Store them.
    stParameters = storeModelParams(bDB, sAccession, stParameters, stSteadyState,
stStartingPoint, stSimulationParameters);
end % Get the simulation parameter sets entered after an input date.
function stSimulationParameters = getSimulationParameters(bDB, sDate, vSimID)
    if (bDB)
        stSimulationParameters = querySimulationParameters(sDate);
    else
        stSimulationParameters = readSimulationParameters(sDate);
    end if (~isempty(vSimID))
        vID = [stSimulationParameters(:).ID];
        ix = ismember(vID, vSimID);
        stSimulationParameters = stSimulationParameters(ix);
    else
        %%%%%
        %%%
        % Pick the simulation approach.
        %%%
        %%%%%
        bLSQ = 0;
        bFMinSearch = 0;
        bPatternSearch = 1;
        bBounded = 1;

sStartingPointMethod = 'Narrow';

sFunctionalForm = 'Simple';      % Linear alpha, exponential beta, sigmoid
v50.
        sFunctionalForm = 'Hybrid';      % Linear alpha, exponential beta, sigmoid
v50.
        sFunctionalForm = 'Exponential'; % Exponential alpha,
exponential beta, and sigmoid v50.
        sFunctionalForm = 'Simple';      % Linear alpha, exponential beta, relational
v50.

sInitialDistribution = 'MVN';
        sInitialDistribution = 'Empirical';
```

FIG. 15I

```
        ixOpt = [];
        if (bLSQ)
            csOptimizers = {stSimulationParameters(:).sOptimizer}';
            ixOpt = [ixOpt; find(strcmp(csOptimizers, 'lsqnonlin'))];
        end
        if (bFMinSearch)
            csOptimizers = {stSimulationParameters(:).sOptimizer}';
            ixOpt = [ixOpt; find(strcmp(csOptimizers, 'fminsearch'))];
        end
        if (bPatternSearch)
            csOptimizers = {stSimulationParameters(:).sOptimizer}';
            ixOpt = [ixOpt; find(strcmp(csOptimizers, 'patternsearch'))];
        end stSimulationParameters = stSimulationParameters(ixOpt);

csMethods = {stSimulationParameters(:).sStartPointMethod}';
        ixSim = strcmp(csMethods, sStartingPointMethod);
        stSimulationParameters = stSimulationParameters(ixSim);

csFunctions =
cellstr(strvcat(stSimulationParameters(:).sFunctionalForm));
        ixFunction = strcmp(csFunctions, sFunctionalForm);
        stSimulationParameters = stSimulationParameters(ixFunction);

csDist = {stSimulationParameters(:).sInitialDistribution}';
        ixDist = strcmp(csDist, sInitialDistribution);
        stSimulationParameters = stSimulationParameters(ixDist);

ixNoBounds = isnan([stSimulationParameters(:).nMinAlpha]);
        if (bBounded)
            ixBounds = ~ixNoBounds;
            stSimulationParameters = stSimulationParameters(ixBounds);
        else
            stSimulationParameters = stSimulationParameters(ixNoBounds);
        end
    end
    stSimulationParameters
end function stSimulationParameters = readSimulationParameters(sDate)
    % Read the sample XLS file to get the Advia File ID.
    [num, txt, raw] =
xlsread('simulation.xls','SimulationParameters','','basic');
    nOffset = size(txt, 1) - size(num, 1);
    stSimulationParameters = [];
    for ixRow = 1:size(num,1)
        % Read the advia file XLS file to get the FCS location and the steady
        % state measurements.
        tSimulationParameters.ID = num(ixRow, 1);
        tSimulationParameters.sDate = txt{ixRow + nOffset, 2};
        tSimulationParameters.sOptimizer = txt{ixRow + nOffset, 3};
        tSimulationParameters.nMeshWidth = num(ixRow, 5);
        tSimulationParameters.nMinV = num(ixRow, 6);
        tSimulationParameters.nMaxV = num(ixRow, 7);
        tSimulationParameters.nMinH = num(ixRow, 8);
        tSimulationParameters.nMaxH = num(ixRow, 9);
        tSimulationParameters.sStartPointMethod = txt{ixRow + nOffset, 10};
        tSimulationParameters.sFunctionalForm = txt{ixRow + nOffset, 11};
        tSimulationParameters.sInitialDistribution = txt{ixRow + nOffset, 12};
        tSimulationParameters.nMinAlpha = num(ixRow, 13);
```

FIG. 15J

```
        tSimulationParameters.nMaxAlpha = num(ixRow, 14);
        tSimulationParameters.sDeathFunction = txt{ixRow + nOffset, 15};
        tSimulationParameters.sOptimalTrend = txt{ixRow + nOffset, 16};
        tSimulationParameters.nSteadyStateVersion = num(ixRow, 17);
        if (~isfinite(tSimulationParameters.nSteadyStateVersion))
            tSimulationParameters.nSteadyStateVersion = 0;
        end
        tSimulationParameters.bPenalizeFalsePositives = num(ixRow, 18);
        if (~isfinite(tSimulationParameters.bPenalizeFalsePositives))
            tSimulationParameters.bPenalizeFalsePositives = 0;
        end
        stSimulationParameters = [stSimulationParameters; tSimulationParameters];
    end
end function stSimulationParameters = querySimulationParameters(sDate)
    sODBC = 'microcytosis';
    r = [];
    conn = database(sODBC, '', '');

curs = exec(conn, ['select * from SimulationParameters']);
    curs = fetch(curs);
    csSimulationParameters = curs.Data;

stSimulationParameters = [];
    for ixStart = 1:size(csSimulationParameters, 1)
        nDate = datenum(csSimulationParameters{ixStart, 2});
        if (nDate > datenum(sDate))
            tSimulationParameters.ID = csSimulationParameters{ixStart, 1};
            tSimulationParameters.nDate = nDate;
            tSimulationParameters.sOptimizer = csSimulationParameters{ixStart, 3};
            tSimulationParameters.nMeshWidth = csSimulationParameters{ixStart, 5};
            tSimulationParameters.nMinV = csSimulationParameters{ixStart, 6};
            tSimulationParameters.nMaxV = csSimulationParameters{ixStart, 7};
            tSimulationParameters.nMinH = csSimulationParameters{ixStart, 8};
            tSimulationParameters.nMaxH = csSimulationParameters{ixStart, 9};
            tSimulationParameters.sStartPointMethod = csSimulationParameters{ixStart, 10};
            tSimulationParameters.sFunctionalForm = csSimulationParameters{ixStart, 11};
            tSimulationParameters.sInitialDistribution = csSimulationParameters{ixStart, 12};
            tSimulationParameters.nMinAlpha = csSimulationParameters{ixStart, 13};
            tSimulationParameters.nMaxAlpha = csSimulationParameters{ixStart, 14};
            tSimulationParameters.sDeathFunction = csSimulationParameters{ixStart, 15};
            tSimulationParameters.sOptimalTrend = csSimulationParameters{ixStart, 16};
            tSimulationParameters.nSteadyStateVersion = csSimulationParameters{ixStart, 17};
            if (isnan(tSimulationParameters.nSteadyStateVersion))
                tSimulationParameters.nSteadyStateVersion = 0;
            end
            tSimulationParameters.bPenalizeFalsePositives = csSimulationParameters{ixStart, 18};
            if (isnan(tSimulationParameters.bPenalizeFalsePositives))
                tSimulationParameters.bPenalizeFalsePositives = 0;
```

FIG. 15K

```
            end
            stSimulationParameters = [stSimulationParameters;
tSimulationParameters];
        end
    end
    close(curs);
    close(conn);
end % Get the starting points entered after the threshold date.
function stStartingPoints = queryStartingPoints(sDate)
    sODBC = 'microcytosis';
    r = [];
    conn = database(sODBC, '', '');

curs = exec(conn, ['select * from StartingPoint']);
    curs = fetch(curs);
    csStartingPoint = curs.Data;
    stStartingPoints = [];
    for ixStart = 1:size(csStartingPoint, 1)
        nDate = datenum(csStartingPoint{ixStart, 2});
        if (nDate > datenum(sDate))
            tStartingPoint.ID = csStartingPoint{ixStart, 1};
            tStartingPoint.nDate = nDate;
            tStartingPoint.alpha = csStartingPoint{ixStart, 3};
            tStartingPoint.betav = csStartingPoint{ixStart, 4};
            tStartingPoint.betah = csStartingPoint{ixStart, 5};
            tStartingPoint.Dv = csStartingPoint{ixStart, 6};
            tStartingPoint.Dh = csStartingPoint{ixStart, 7};
            tStartingPoint.v50 = csStartingPoint{ixStart, 8};
            stStartingPoints = [stStartingPoints; tStartingPoint];
        end
    end
    close(curs);
    close(conn);
end function [Phat, P, vi, hi] = makeEmpiricalPDF(vData, hcData)
    P = [];
    % Convert hemoglobin content (mass), not concentration.
    hData = vData.*hcData/100;

% Assume the true RBC population distribution is bivariate normal.
    % Approximate the true distribution from a smoothing of the sample.
    vi = linspace(min(vData), max(vData), round(range(vData)));
    hi = linspace(min(hData), max(hData), round(range(hData)));

ctrs{1} = hi;
    ctrs{2} = vi;

% Calculate the empirical distribution.
    P = hist3([hData, vData], ctrs);
    P = flipud(P);
    hi = fliplr(hi);
    vi = repmat(vi(:)', size(P, 1), 1);
    hi = repmat(hi(:), 1, size(P, 2));

% Also approximate the true distribution by smoothing the raw data.
    n = 3;
    nCenterWeight = 1/n;
    k = (1 - nCenterWeight)*(1/(n^2 - 1))*ones(n,n);
```

FIG. 15L

```
    k(ceil(n/2),ceil(n/2)) = nCenterWeight;
    Phat = conv2(P, k, 'same');
    Phat = sum(P(:))*Phat/sum(Phat(:));
    %ixCells = find(P > 5);
    %Phat = sum(P(ixCells))*Phat/sum(Phat(ixCells));
    %chi2 = sum((P(ixCells) - Phat(ixCells)).^2./P(ixCells));
end function xi = getNormSpace(x)
    mu = median(x);
    sigma = iqr(x)*0.7314;
    normx = linspace((min(x) - mu)/sigma, (max(x) - mu)/sigma, round(range(x)));
    xi = abs(2*normx.*exp(-1*normx.^2));
    xi = xi/sum(xi);
    xi = cumsum(xi);
    xi = [0 xi];
    xi = xi*range(x) + min(x);
end function stSteadyState = queryFCSSteadyState(sAccession, sDate, nVersion)
    % Given an accession number, return, calculate, and populate the steady
    % state parameters after a given date as necessary.

sODBC = 'microcytosis';
    r = [];
    conn = database(sODBC, '', '');

% Get all sample IDs.
    nSampleID = getSampleID(conn, sAccession);

if (~isempty(nSampleID))

% Get the ADVIA file names and measured results.
        stAdviaFile = getAdviaFile(conn, nSampleID);

% Get the calculated steady state values.
        stSteadyState = getCalculatedSteadyState(conn, stAdviaFile);

% Get those calculated after a certain date.
        stSteadyState = getCurrentSteadyState(stSteadyState, sDate, nVersion);

% If there's no fresh steady state:
        if (isempty(stSteadyState))
            % Calculate and store the steady state if not already stored.
            stSteadyState = calculateSteadyState(conn, stAdviaFile, nVersion);
            stSteadyState = getCalculatedSteadyState(conn, stAdviaFile);
            stSteadyState = getCurrentSteadyState(stSteadyState, sDate,
nVersion);
        end % Add the advia-calculated parameters in case the simulation wants
        % to use them.
        for ix = 1:numel(stSteadyState)
            stSteadyState(ix).stAdviaFile = stAdviaFile;
        end
    end close(conn);
end
```

FIG. 15M

```
function stSteadyState = calculateSteadyState(conn, stAdviaFile, nVersion)
    stSteadyState = [];

% Calculate the moments of the RBC distribution.
    [nMCV, nRDW, nCHCM, nHDW, nRho, v, h, nVersion] = getRBCPDF(stAdviaFile,
nVersion);

% Calculate the moments of the reticulocyte distribution.
    [f, nrMCV, nrRDW, nrCHCM, nrHDW, nrRho, vr, hr, nVersion] =
getReticPDF(stAdviaFile, nVersion);

nDate = now;
    sDate = datestr(nDate, 'mm/dd/yyyy HH:MM:SS PM');
    colNames = {'DateEntered', 'AdviaFile', 'MCV', 'RDW', 'MCH', 'HDW', 'rho',
...
        'rFraction', 'rMCV', 'rRDW', 'rMCH', 'rHDW', 'rRho', 'nVersion'};
    newData = {sDate, stAdviaFile.ID, nMCV, nRDW/100, nCHCM, nHDW/100, nRho(1,2),
...
        f, nrMCV, nrRDW/100, nrCHCM, nrHDW/100, nrRho(1,2), nVersion};
    fastinsert(conn, 'SteadyStateParameters', colNames, newData);
    commit(conn);

curs = exec(conn, ['select max(ID) from SteadyStateParameters']);
    curs = fetch(curs);
    nID = curs.Data;
    stSteadyState.ID = cell2mat(nID);
end % Return a list of steady state caculations with dates after an input and
% sorted.
function stSteadyState = getCurrentSteadyState(stSteadyState, sDate, nVersion)
    if (isfinite(nVersion))
        if (numel(stSteadyState))
            vVersions = [stSteadyState(:).nSteadyStateVersion];
            ix = find(vVersions == nVersion);
            stSteadyState = stSteadyState(ix);
        end
    end
    if numel(stSteadyState)
        vDates = [stSteadyState(:).nDate];
        ixCurrent = find(vDates > datenum(sDate));
        [t, ix] = sort([stSteadyState(ixCurrent).nDate]);
        stSteadyState = stSteadyState(ixCurrent(ix));
        stSteadyState = stSteadyState(end);
    end
end function [nMCV, nRDW, nMCH, nHDW, nRho, v, hc, nVersion] = getRBCPDF(stAdviaFile,
nVersion)
    if (nargin < 2)
        nVersion = 0;
    end if (isstruct(stAdviaFile))
        sFCS = stAdviaFile.RBCFCSFile;
    else
        sFCS = stAdviaFile;
    end
```

FIG. 15N

```
    if (~isempty(sFCS) && ~strcmp(sFCS, 'null'))
        % Old version using FCS files.
        [nMCV, nRDW, nMCH, nHDW, nRho, v, hc, nVersion] =
compareMieTransforms(sFCS, nVersion);
    else
        % Assume it's an Abbott-supplied file.
        [nMCV, nRDW, nMCH, nHDW, nRho, v, hc] = getCSVPDF(stAdviaFile);
    end
end function [nMCV, nRDW, nMCH, nHDW, nRho, v, hc] = getCSVPDF(stAdviaFile)
    [n, t, r] = xlsread(stAdviaFile.RawDataFile);
    ixRetic = (n(:,1) == 1);
    ixRBC = (n(:,1) == 2);

v = n(ixRBC, 3);
    hc = n(ixRBC, 2);
    h = v.*hc/100;
    nMCH = mean(h);
    nMCV = mean(v);
    nRDW = 100*std(v)/nMCV;
    nHDW = 100*std(h)/nMCH;
    nRho = corrcoef([v h]);
end function [f, nrMCV, nrRDW, nrCHCM, nrHDW, nrRho, vr, hcr, nVersion] =
getReticPDF(stAdviaFile, nVersion)
    if (nargin < 2)
        nVersion = 0;
    end if (isstruct(stAdviaFile))
        sFCS = stAdviaFile.ReticFCSFile;
    else
        sFCS = stAdviaFile;
    end if (~isempty(sFCS) && ~strcmp(sFCS, 'null'))
        % Old version using FCS files.
        [f, nrMCV, nrRDW, nrCHCM, nrHDW, nrRho, vr, hcr, nVersion] =
estimateReticFraction(sFCS, nVersion);
    else
        % Assume it's an Abbott-supplied file.
        [f, nrMCV, nrRDW, nrCHCM, nrHDW, nrRho, vr, hcr] =
getCSVReticPDF(stAdviaFile);
    end
end function [f, nrMCV, nrRDW, nrCHCM, nrHDW, nrRho, vr, hcr] =
getCSVReticPDF(stAdviaFile)
    [n, t, r] = xlsread(stAdviaFile.RawDataFile);
    ixRetic = (n(:,1) == 1);
    ixRBC = (n(:,1) == 2);

vr = n(ixRetic, 3);
    hcr = n(ixRetic, 2);
    hr = vr.*hcr/100;
    nrCHCM = mean(hr);
    nrMCV = mean(vr);
```

FIG. 15O

```
    nrRDW = 100*std(vr)/nrMCV;
    nrHDW = 100*std(hr)/nrCHCM;
    nrRho = corrcoef([vr hr]);
    f = 100*sum(ixRetic)/sum(ixRBC);
end function [f, nMCV, nRDW, nMCH, nHDW, nRho, v, h, nVersion] =
estimateReticFraction(sFCS, nVersion, nSigmaMin, nSigmaMax)
    if (nargin < 3)
        nSigmaMin = (2*sqrt(2*log(2)));
        nSigmaMax = Inf;
        if (nargin < 2)
            nVersion = 0;
        end
    end if (~exist(sFCS))
        sNewName = strrep(sFCS, 'Z:\Research\Microcytosis',
'C:\local\john\BWH\Microcytosis');
        if (~exist(sNewName))
            sNewName = strrep(sFCS, 'Z:\Research\Microcytosis',
'C:\local\jhiggins\research\microcytosis');
        end
        sFCS = sNewName;
    end

[d,p,h] = fcsread(sFCS);
    m = makeMieLookupTable;

if (nVersion == 0)
        d = filterRaw(d);
        [v, h, ix] = transformMie(m, d, 5);
        d = d(ix, :);
        [v, h, ix] = filterTransformed(v, h);
        d = d(ix, :);

n = hist(d(:,3), [1:256]);
        [pMax, ixMode] = max(n);
        ixHigh = find(n >= pMax/2);
        sigma_hat = range(ixHigh)/(2*sqrt(2*log(2)));
        ixV = find(d(:, 3) >= (median(d(:, 3)) + nSigmaMin*sigma_hat));
        if (isfinite(nSigmaMax))
            ixV = intersect(ixV, find(d(:, 3) <= (median(d(:, 3)) +
nSigmaMax*sigma_hat)));
        end
        f = 100*length(ixV)/size(d, 1);

[v, h, ix] = transformMie(m, d(ixV,:), 5);
        nMCV = mean(v);
        nRDW = 100*std(v)/mean(v);
        nMCH = mean(v.*h/100);
        nHDW = 100*std(100*v.*h)/mean(100*v.*h);
        nRho = corrcoef([v v.*h]);
    elseif (nVersion == 1)
        stPBANRES = getReticPBANRES(sFCS);
        [v, h, ix, vFull, hFull] = transformMie(m, d, inf);
        n99 = 250 - 2.5;
        ixBZ = find(d(:, 3) >= n99);
        ixNull = (union(find(isnan(hFull)), find(isnan(vFull))));
```

FIG. 15P

```
        ixNotAnalyzed = union(ixNull, ixBZ);
        ixAnalyzed = setdiff(1:size(d, 1), ixNotAnalyzed);

nBins = 99;
        [xCounts, xBins] = hist(d(:,2), nBins);
        ixX = intersect(find(d(ixAnalyzed,2) >=
mean(xBins(max(stPBANRES.nPLTThreshold, 2) + [-1 0]))), find(d(ixAnalyzed,2) <=
mean(xBins(stPBANRES.nMaxX + [0 1]))));

[yCounts, yBins] = hist(d(:,1), nBins);
        ixY = intersect(find(d(ixAnalyzed,1) > 0), find(d(ixAnalyzed,1) <=
mean(yBins(stPBANRES.nMaxY + [0 1]))));
        ixGated = intersect(ixX, ixY);

[zCounts, zBins] = hist(d(:,3), nBins);
        ixRetic = (find(d(ixAnalyzed(ixGated), 3) >=
mean(zBins(stPBANRES.nMinRTThreshold + [-1 0]))));
        ixLo = (find(d(ixAnalyzed(ixGated), 3) >=
zBins(stPBANRES.nLoThreshold)));
        ixMed = (find(d(ixAnalyzed(ixGated), 3) >=
zBins(stPBANRES.nMedThreshold)));

v = vFull(ixAnalyzed(ixGated(ixRetic)));
        h = hFull(ixAnalyzed(ixGated(ixRetic)));
        f = 100*length(ixRetic)/length(ixGated);
        nMCV = mean(v);
        nRDW = 100*iqr(v)*0.7413/nMCV;
        nMCH = mean(v.*h/100);
        nHDW = 100*iqr(100*v.*h)*0.7413/mean(100*v.*h);
        nRho = corrcoef([v v.*h]);
    elseif (nVersion == 2)
        stPBANRES = getReticPBANRES(sFCS);
        [v, h, ix, vFull, hFull] = transformMie(m, d, inf);
        n99 = 150 - 2.5;
        ixBZ = find(d(:, 3) >= n99);
        ixNull = (union(find(isnan(hFull)), find(isnan(vFull))));
        ixNotAnalyzed = union(ixNull, ixBZ);
        ixAnalyzed = setdiff(1:size(d, 1), ixNotAnalyzed);

nBins = 99;
        [xCounts, xBins] = hist(d(:,2), nBins);
        ixX = intersect(find(d(ixAnalyzed,2) >=
mean(xBins(max(stPBANRES.nPLTThreshold, 2) + [-1 0]))), find(d(ixAnalyzed,2) <=
mean(xBins(stPBANRES.nMaxX + [0 1]))));

[yCounts, yBins] = hist(d(:,1), nBins);
        ixY = intersect(find(d(ixAnalyzed,1) > 0), find(d(ixAnalyzed,1) <=
mean(yBins(stPBANRES.nMaxY + [0 1]))));
        ixGated = intersect(ixX, ixY);

[zCounts, zBins] = hist(d(:,3), nBins);
        ixRetic = (find(d(ixAnalyzed(ixGated), 3) >=
mean(zBins(stPBANRES.nMinRTThreshold + [-1 0]))));
        ixLo = (find(d(ixAnalyzed(ixGated), 3) >=
zBins(stPBANRES.nLoThreshold)));
        ixMed = (find(d(ixAnalyzed(ixGated), 3) >=
zBins(stPBANRES.nMedThreshold)));

nThreshold = prctile(d(ixAnalyzed(ixGated), 3),100*(1 -
stPBANRES.nReticCount/stPBANRES.nGatedCount));
```

FIG. 15Q

```
        ixRetic = find(d(ixAnalyzed(ixGated), 3) >= nThreshold);

v = vFull(ixAnalyzed(ixGated(ixRetic)));
        h = hFull(ixAnalyzed(ixGated(ixRetic)));
        f = 100*length(ixRetic)/length(ixGated);
        nMCV = mean(v);
        nRDW = 100*iqr(v)*0.7413/nMCV;
        nMCH = mean(v.*h/100);
        nHDW = 100*iqr(100*v.*h)*0.7413/mean(100*v.*h);
        nRho = corrcoef([v v.*h]);
    elseif (nVersion == 3)
        stPBANRES = getReticPBANRES(sFCS);
        [v, h, ix, vFull, hFull] = transformMie(m, d, inf);
        n99 = 250 - 2.5;
        ixBZ = find(d(:, 3) >= n99);
        ixNull = (union(find(isnan(hFull)), find(isnan(vFull))));
        ixNotAnalyzed = union(ixNull, ixBZ);
        ixAnalyzed = setdiff(1:size(d, 1), ixNotAnalyzed);

nBins = 99;
        [xCounts, xBins] = hist(d(:,2), nBins);
        ixX = intersect(find(d(ixAnalyzed,2) >=
mean(xBins(max(stPBANRES.nPLTThreshold, 2) + [-1 0]))), find(d(ixAnalyzed,2) <=
mean(xBins(stPBANRES.nMaxX + [0 1]))));

[yCounts, yBins] = hist(d(:,1), nBins);
        ixY = intersect(find(d(ixAnalyzed,1) > 0), find(d(ixAnalyzed,1) <=
mean(yBins(stPBANRES.nMaxY + [0 1]))));
        ixGated = intersect(ixX, ixY);

[zCounts, zBins] = hist(d(:,3), nBins);
        ixRetic = (find(d(ixAnalyzed(ixGated), 3) >=
mean(zBins(stPBANRES.nMinRTThreshold + [-1 0]))));
        ixLo = (find(d(ixAnalyzed(ixGated), 3) >=
zBins(stPBANRES.nLoThreshold)));
        ixMed = (find(d(ixAnalyzed(ixGated), 3) >=
zBins(stPBANRES.nMedThreshold)));

nThreshold = prctile(d(ixAnalyzed(ixGated), 3),100*(1 -
stPBANRES.nReticCount/stPBANRES.nGatedCount));
        ixRetic = find(d(ixAnalyzed(ixGated), 3) >= nThreshold);

v = vFull(ixAnalyzed(ixGated(ixRetic)));
        h = hFull(ixAnalyzed(ixGated(ixRetic)));
        nMCV = mean(v);
        nMCH = mean(v.*h/100);
        v = v*stPBANRES.nMCVr/nMCV;
        h = h*(stPBANRES.nMCHr/stPBANRES.nMCVr)/(nMCH/nMCV);
        nMCV = mean(v);
        nMCH = mean(v.*h/100);
        f = 100*length(ixRetic)/length(ixGated);
        nRDW = 100*iqr(v)*0.7413/nMCV;
        nHDW = 100*iqr(100*v.*h)*0.7413/mean(100*v.*h);
        nRho = corrcoef([v v.*h]);
    elseif (nVersion == 5)
        stPBANRES = getReticPBANRES(sFCS);
        [v, h, ix, vFull, hFull] = transformMie(m, d, inf);
        n99 = 250 - 2.5;
        ixBZ = find(d(:, 3) >= n99);
        ixNull = (union(find(isnan(hFull)), find(isnan(vFull))));
```

FIG. 15R

```
        ixNotAnalyzed = union(ixNull, ixBZ);
        ixAnalyzed = setdiff(1:size(d, 1), ixNotAnalyzed);

nBins = 99;
        [xCounts, xBins] = hist(d(:,2), nBins);
        ixX = intersect(find(d(ixAnalyzed,2) >=
mean(xBins(max(stPBANRES.nPLTThreshold, 2) + [-1 0]))), find(d(ixAnalyzed,2) <=
mean(xBins(stPBANRES.nMaxX + [0 1]))));

[yCounts, yBins] = hist(d(:,1), nBins);
        ixY = intersect(find(d(ixAnalyzed,1) > 0), find(d(ixAnalyzed,1) <=
mean(yBins(stPBANRES.nMaxY + [0 1]))));
        ixGated = intersect(ixX, ixY);

[zCounts, zBins] = hist(d(:,3), nBins);
        ixRetic = (find(d(ixAnalyzed(ixGated), 3) >=
mean(zBins(stPBANRES.nMinRTThreshold + [-1 0]))));
        ixLo = (find(d(ixAnalyzed(ixGated), 3) >=
zBins(stPBANRES.nLoThreshold)));
        ixMed = (find(d(ixAnalyzed(ixGated), 3) >=
zBins(stPBANRES.nMedThreshold)));

nThreshold = prctile(d(ixAnalyzed(ixGated), 3),100*(1 -
stPBANRES.nReticCount/stPBANRES.nGatedCount));
        ixRetic = find(d(ixAnalyzed(ixGated), 3) >= nThreshold);

v = vFull(ixAnalyzed(ixGated(ixRetic)));
        h = hFull(ixAnalyzed(ixGated(ixRetic)));

h_pg = v.*h/100;
        nMCV = mean(v);
        nMCH = mean(h_pg);
        nsdV = std(v);
        nsdH_PG = std(h_pg);

% Shift and scale to match the mean and variance.
        v = (v - nMCV)/nsdV;
        v = (v*stPBANRES.nRDWr*stPBANRES.nMCVr/100) + stPBANRES.nMCVr;
        h_pg = (h_pg - nMCH)/nsdH_PG;
        h_pg = (h_pg*stPBANRES.nCHDWr) + stPBANRES.nMCHr;
        h = 100*h_pg./v;
        nMCV = mean(v);
        nMCH = mean(v.*h/100);

nRDW = 100*iqr(v)*0.7413/nMCV;
        nHDW = 100*iqr(100*v.*h)*0.7413/mean(100*v.*h);
        nRho = corrcoef([v v.*h]);

f = 100*length(ixRetic)/length(ixGated);
    end
end function oQuasiLinearFit = getQuasiLinearFit(stParameters, vData, hcData)
    qft = fittype('a*x+b');
    oQuasiLinearFit = fit(vData, vData.*hcData/100, qft);
end function [stParameters, nSampleID] = getRBCPDFParameters(nModelParametersID)
```

FIG. 15S

```
    nSampleID = [];
    if (nargin == 0)
        stParameters.nMeshWidth = 1.8;
        stParameters.nMaxVolume = 180;
        stParameters.nMinVolume = 30;
        stParameters.nMaxHb = 60;
        stParameters.nMinHb = 0;
        [V,H] =
meshgrid([stParameters.nMinVolume:stParameters.nMeshWidth:stParameters.nMaxVolume
], ...
            [stParameters.nMinHb:stParameters.nMeshWidth:stParameters.nMaxHb]);
        H = flipud(H);
        stParameters.V = V;
        stParameters.H = H;

stParameters.sOptimizer = 'lsqnonlin';
        stParameters.sDeathFunction = 'Dimensionless Projection';
        stParameters.sFunctionalForm = 'Additive Exponential';
        stParameters.bParallel = 0;
        stParameters.bMatchParameters = 0;
        stParameters.bPenalizeFalsePositives = 0;
        stParameters.nMinAlpha = NaN;
        stParameters.nMaxAlpha = NaN;

stParameters.nMeanMarrowVolume = 109.3;
        stParameters.nCVMarrowVolume = 0.1129;
        stParameters.nMeanMarrowHb = 32.6;
        stParameters.nCVMarrowHb = 0.101;
        stParameters.nMarrowRho = 0.34;
        stParameters.vStar = 92.04;
        stParameters.hStar = 30.04;
        stParameters.nDays = 0;
        stParameters.muAgeTarg = 50;

sdV = (stParameters.nCVMarrowVolume*stParameters.nMeanMarrowVolume);
        sdH = (stParameters.nCVMarrowHb*stParameters.nMeanMarrowHb);
        nCovar = stParameters.nMarrowRho*sdV*sdH;
        mSigma = [sdV^2 nCovar; nCovar sdH^2];
        P_0 = mvnpdf([V(:) H(:)], [stParameters.nMeanMarrowVolume
stParameters.nMeanMarrowHb], mSigma);
        P_0 = P_0(:)/sum(P_0(:));
        stParameters.P_0 = P_0;

stParameters.alphav = .0017; % Rate of translation down the "optimal" HC
ratio: [0, 0.1];
        stParameters.alphah = stParameters.alphav; % Rate of translation down the
"optimal" HC ratio: [0, 0.1].
        stParameters.betav = 19.3; % Rate of movement toward the "optimal" ratio:
[0 120?];
        stParameters.betah = 9.0; % Rate of movement toward the "optimal" ratio:
[0 120?].
        stParameters.v50 = 77.9; %0.9*stParameters.vStar; % Volume where
P(clearance) = 50%: [0, 0.9]*MCV.
        stParameters.Dv = 2.6; %3.2774: [0 100?];
        stParameters.Dh = 0.0015; %.0793: [0 100?];
        stParameters.nSlope = 1;
        stParameters.alphaDecay = NaN;
        stParameters.sOptimalTrend = 'Linear';
```

FIG. 15T

```
else
    sODBC = 'microcytosis';
    r = [];
    conn = database(sODBC, '', '');
    csMP = getModelParameters(conn, nModelParametersID);

ssID = csMP{2};
    csSS = getSteadyStatebyID(conn, ssID);

ssVersion = csSS{15};
    if (~isfinite(ssVersion))
        ssVersion = 0;
    end afID = csSS{3};
    % Get the advia ID from the sample ID.
    csAdviaFile = getAdviaFileByID(conn, afID);
    csAdviaFile = expandFCSFilenames(csAdviaFile);
    nSampleID = afID;

simID = csMP{3};
    csSimulationParameters = getSimulationParametersByID(conn, simID);
    close(conn);

stParameters.nMeshWidth = csSimulationParameters{5};
    stParameters.nMaxVolume = csSimulationParameters{7};
    stParameters.nMinVolume = csSimulationParameters{6};
    stParameters.nMaxHb = csSimulationParameters{9};
    stParameters.nMinHb = csSimulationParameters{8};
    [V,H] =
meshgrid([stParameters.nMinVolume:stParameters.nMeshWidth:stParameters.nMaxVolume
], ...
        [stParameters.nMinHb:stParameters.nMeshWidth:stParameters.nMaxHb]);
    H = flipud(H);
    stParameters.V = V;
    stParameters.H = H;

stParameters.sOptimizer = csSimulationParameters{3};
    stParameters.sFunctionalForm = csSimulationParameters{11};
    stParameters.bMatchParameters = 0;
    stParameters.nMinAlpha = csSimulationParameters{13};
    stParameters.nMaxAlpha = csSimulationParameters{14};
    stParameters.sDeathFunction = csSimulationParameters{15};
    stParameters.bParallel = 0;
    if (strcmp(csSimulationParameters{16}, 'null'))
        stParameters.sOptimalTrend = 'Linear';
    else
        stParameters.sOptimalTrend = csSimulationParameters{16};
    end
    stParameters.bPenalizeFalsePositives = csSimulationParameters{18};
    if (strcmp(csSimulationParameters{18}, 'null') ||
isnan(csSimulationParameters{18}))
        stParameters.bPenalizeFalsePositives = 0;
    end stParameters.nMeanMarrowVolume = csSS{10};
    stParameters.nCVMarrowVolume = csSS{11};
    stParameters.nMeanMarrowHb = csSS{12};
    stParameters.nCVMarrowHb = csSS{13};
    stParameters.nMarrowRho = csSS{14};
```

FIG. 15,U

```
        stParameters.vStar = csSS{4};
        stParameters.hStar = csSS{6};
        stParameters.nDays = 0;

stParameters.muAgeTarg = csMP{11};

stParameters.alphav = csMP{12}; % Rate of translation down the "optimal"
HC ratio: [0, 0.1];
        stParameters.alphah = csMP{13}; % Rate of translation down the "optimal"
HC ratio: [0, 0.1].
        stParameters.betav = csMP{14}; % Rate of movement toward the "optimal"
ratio: [0 120?];
        stParameters.betah = csMP{15}; % Rate of movement toward the "optimal"
ratio: [0 120?].
        stParameters.v50 = csMP{16}; %0.9*stParameters.vStar; % Volume where
P(clearance) = 50%: [0, 0.9]*MCV.
        stParameters.Dv = csMP{17}; %3.2774: [0 100?];
        stParameters.Dh = csMP{18}; %.0793: [0 100?];
        if (size(csMP, 2) == 26)
            stParameters.nSlope = 1;
            stParameters.alphaDecay = NaN;
        elseif (size(csMP, 2) == 27)
            stParameters.nSlope = csMP{27};
            stParameters.alphaDecay = NaN;
        else
            stParameters.nSlope = csMP{27};
            stParameters.alphaDecay = csMP{28};
        end
        if (isnan(stParameters.nSlope))
            stParameters.nSlope = 1;
        end if (isnan(stParameters.alphaDecay))
            stParameters.alphaDecay = 5;
        end

[f, nMCV, nRDW, nMCH, nHDW, nRho, vData, hcData] =
estimateReticFraction(csAdviaFile{6}, ssVersion);
        [Phat, P, vi, hi] = makeEmpiricalPDF(vData, hcData);
        P_0 = interp2(vi, hi, Phat, V, H, 'linear', 0);
        P_0 = P_0(:)./sum(P_0(:));
        stParameters.P_0 = P_0;

[nMCV, nRDW, nCHCM, nHDW, nRho, vData, hcData] =
compareMieTransforms(csAdviaFile{5}, ssVersion);
        stParameters.vData = vData;
        stParameters.hcData = hcData;

if (strcmp(stParameters.sOptimalTrend, 'Quasi-linear'))
            stParameters.oQuasiLinearFit = getQuasiLinearFit(stParameters,
stParameters.vData, stParameters.hcData);
        end if 0
            sdV = (stParameters.nCVMarrowVolume*stParameters.nMeanMarrowVolume);
            sdH = (stParameters.nCVMarrowHb*stParameters.nMeanMarrowHb);
            nCovar = stParameters.nMarrowRho*sdV*sdH;
            mSigma = [sdV^2 nCovar; nCovar sdH^2];
            P_01 = mvnpdf([V(:) H(:)], [stParameters.nMeanMarrowVolume
stParameters.nMeanMarrowHb], mSigma);
```

FIG. 15V

```
            P_01 = reshape(sum(P_0(:))*P_01/sum(P_01(:)), size(V));
        end
    end
end
function [r, mu_v, cv_v, mu_h, cv_h] = computeRBCCorr(P, V, H)
    mu_v = P*(V(:))/sum(P(:));
    var_v = P*(V(:).^2)/sum(P(:)) - mu_v^2;
    cv_v = 100*sqrt(var_v)/mu_v;
    mu_h = P*(H(:))/sum(P(:));
    var_h = P*(H(:).^2)/sum(P(:)) - mu_h^2;
    cv_h = 100*sqrt(var_h)/mu_h;

cov_vh = P*(V(:).*H(:))/sum(P(:)) - 2*mu_v*mu_h + mu_v*mu_h;
    r = cov_vh/sqrt(var_v)/sqrt(var_h);
end function [mBirthAlive, vMeanAge, Pf, Pt] = computeAgeDistribution(P)
    vDailyTotals = sum(P');
    ixInsignificant = find(vDailyTotals < 1e-6);
    %vDailyTotals(ixInsignificant) = 0;
    nDays = numel(vDailyTotals);

% Matrix with current day in column and day-cohort in row.
    % The (i,j) entry is the fraction of cells born on the ith day alive on
    % the jth day.
    mBirthAlive = zeros(nDays, nDays);
    for ix = 1:nDays
        mBirthAlive(ix, ix:end) = vDailyTotals(1:(end - ix + 1));
    end % Compute the total density born on each day by adding up the amount
    % that each previous cohort lost the previous day.
    % mAge(i,j) = the absolute density of cells born on day i that are
    % cleared on day j.
    mAge = -1*[zeros(nDays, 1), diff(mBirthAlive')'];
    vWeights = ones(nDays, 1);
    for ix = 2:nDays
        mAge(ix,ix) = 0;
        vWeights(ix) = sum(mAge(:, ix));
        mAge(ix, :) = mAge(ix, :)*vWeights(ix);
    end % Convert mBirthAlive to absolute densities:
    % mBirthAlive(i,j) = absolute density of cells born on day i that
    % are alive on day j.  Column j represents the age distribution
    % for circulating cells on day j.
    mBirthAlive = mBirthAlive.*repmat(vWeights, 1, nDays);
    for ix = 1:nDays
        vMeanAge(ix) = (mBirthAlive(:, ix)')*[ix:-1:(ix - nDays + 1)]';
    end % Compute the total distribution on the last day.
    % The ith cohort has grown for (nDays - i) days.
    mWeights = flipud(repmat(mBirthAlive(:, end), [1 size(P, 2)]));
    Pnorm = P./repmat(sum(P')', [1 size(P, 2)]);
    Pf = Pnorm.*mWeights;
    if (size(Pf, 1) > 1)
        Pf = sum(Pf);
```

FIG. 15W

```
        end
    Pt = NaN*ones(nDays, size(Pf, 2));
    if (nargout == 4)
        tSamples = 1;
        for ix = 1:tSamples:(nDays - 1)
            mWeights = flipud(repmat(mBirthAlive(1:ix, ix), [1 size(P, 2)]));
            Ptemp = Pnorm(1:ix, :).*mWeights;
            if (size(Ptemp, 1) > 1)
                Ptemp = sum(Ptemp);
            end
            Pt(max(1, floor(ix/tSamples)), :) = Ptemp;
        end
        Pt(end, :) = Pf;
    end
end function [P, t, V, H, stParameters] = fdRBC(stParameters)
    P = [];
    t = [];
    % Get the parameters.
    if (~exist('stParameters'))
        stParameters = getRBCPDFParameters();
    end
    vt = [0:stParameters.nDays];
    V = stParameters.V;
    H = stParameters.H;
    P_0 = stParameters.P_0;

% Setup the clearance function.
    pCleared = getCleared(stParameters, V, H);
    stParameters.pCleared = pCleared;

% Set up the indices of the mesh points on the boundary.
    ixTopRight = (numel(V) - size(V, 1) + 1);
    ixBottomRight = numel(V);
    ixBottomLeft = size(V, 1);
    ixTopLeft = 1;
    ixRightEdge = [(numel(V) - size(V, 1) + 2):(numel(V) - 1)];
    ixTopEdge = [(size(V, 1) + 1):size(V, 1):(numel(V) - 2*size(V, 1) + 1)];
    ixLeftEdge = [2:(size(V, 1) - 1)];
    ixBottomEdge = [2*size(V, 1):size(V, 1):(numel(V) - size(V, 1))];
    ixVStep = size(V, 1);
    ixInterior = setdiff([1:numel(V)], [ixTopRight ixBottomRight ixBottomLeft
ixTopLeft ixRightEdge ixTopEdge ixLeftEdge ixBottomEdge]);

mVDot = vdot(stParameters, V, H);
    mHDot = hdot(stParameters, V, H);

if (0)
        % Code to draw the velocity fields.
        clf
        nRange = 0.25;
        [V,H] = meshgrid([stParameters.nMinVolume:.3:stParameters.nMaxVolume],
...
            [stParameters.nMinHb:0.1:stParameters.nMaxHb]);
        mVDot = vdot(stParameters, V, H);
        mHDot = hdot(stParameters, V, H);
        VC = H./V;
```

FIG. 15X

```
        ix = find(VC(:) > (1.0 - 
nRange)*(stParameters.hStar/stParameters.vStar));
        ix = intersect(ix, find(VC(:) < (1.0 + 
nRange)*(stParameters.hStar/stParameters.vStar)));
        mLength = mVDot.^2 + mHDot.^2;
        nScale = 4;
        %pvf = quiver(V(ix), H(ix),  -1*(abs(mVDot(ix)).^nScale), -
1*(abs(mHDot(ix)).^nScale),'autoscalefactor',1, 'linewidth', 2, 'maxheadsize',
0.5);
        plot([0 2*stParameters.vStar],[0 2*stParameters.hStar], 'color', 'k',
'linewidth', 4);
        hold on;
        pvf = quiver(V(ix), H(ix),  -1*(abs(mVDot(ix))/nScale), -
1*(abs(mHDot(ix))/nScale),'autoscale', 'off', 'linewidth', 2, 'maxheadsize', 0.2,
'color', 'b');
        yl = [29.5 30.5];
        %yl = [27.5 32.5];
        xl = (stParameters.vStar/stParameters.hStar)*yl;
        set(gca,'ylim', yl);
        set(gca,'xlim', xl);
        nSize = 20;
        xlabel('volume (fL)', 'fontsize', nSize);
        ylabel('hemoglobin (pg)', 'fontsize', nSize);
        set(gca,'fontsize',nSize);
    end

[spJacobian, J] = getJacobian(stParameters, mVDot, mHDot, ...
        ixTopRight, ixBottomRight, ixBottomLeft, ixTopLeft, ixRightEdge,
ixTopEdge, ixLeftEdge, ixBottomEdge, ixInterior, ixVStep);
    stParameters.J = J;

[spLaplacian, L] = getLaplacian(stParameters, numel(mVDot), ixTopRight,
ixBottomRight, ixBottomLeft, ixTopLeft, ...
        ixRightEdge, ixTopEdge, ixLeftEdge, ixBottomEdge, ixInterior, ixVStep);
    spJacobian = spones(J + L);
    stParameters.L = L;

if (stParameters.nDays)
        odeOptions = odeset('Vectorized', 'on', 'JPattern', spJacobian,
'OutputFcn', 'odeplot');
        odeOptions = odeset('Vectorized', 'on', 'JPattern', spJacobian, 'AbsTol',
1e-6, 'OutputFcn', 'odeplot');
        odeOptions = odeset('Vectorized', 'on', 'JPattern', spJacobian);
        optset = optimset('TolX', 10^(-12), 'MaxFun', 1e10, 'MaxIter', 1e10);
        [t, P] = ode15s(@fUpwind, vt, P_0, odeOptions);
        %[t, P] = fsolve(@fUpwind, P_0, optset);
        %[t, P] = fminsearch(@fUpwind, P_0, optset);
    end function dP_dt = fUpwind(t, P)
        dP_dt = zeros(size(P,1), size(P, 2));

[dP_Cleared, nCleared] = clearRBC(pCleared, P, V, H);
        P_born = P_0*nCleared;
        if 0
            dP_dt = J*P  + L*P - dP_Cleared + P_born;
        else
            dP_dt = J*P + L*P - dP_Cleared;
        end
    end
end
```

FIG. 15.Y

```
function pCleared = getCleared(stParameters, V, H)
    nSlope = stParameters.nSlope;
    if (isfield(stParameters, 'sDeathFunction'))
        assert(strcmp(stParameters.sDeathFunction, 'Projection') || ...
strcmp(stParameters.sDeathFunction, 'Dimensionless Projection') || ...
            strcmp(stParameters.sDeathFunction, 'Tunable Dimensionless
Projection') || strcmp(stParameters.sDeathFunction, '0.1 Dimensionless
Projection'));

if (strcmp(stParameters.sDeathFunction, '0.1 Dimensionless Projection'))
            nSlope = 0.1;
            stParameters.nSlope = 0.1;
        end if (strcmp(stParameters.sOptimalTrend, 'Quasi-linear'))
            theta = atan(stParameters.oQuasiLinearFit.a);
            mAngle = atan((H - stParameters.oQuasiLinearFit.b)./V);
            mNorm = (V.^2 + (H - stParameters.oQuasiLinearFit.b).^2).^(1/2);
            vr50 = (stParameters.v50^2 +
(stParameters.v50*stParameters.oQuasiLinearFit.a)^2)^(1/2);
        else
            theta = atan(stParameters.hStar/stParameters.vStar);
            mAngle = atan(H./V);
            mNorm = (V.^2 + H.^2).^(1/2);
            vr50 = (stParameters.v50^2 +
(stParameters.v50*stParameters.hStar/stParameters.vStar)^2)^(1/2);
        end
        Vr = mNorm.*cos(theta - mAngle);

if (strcmp(stParameters.sFunctionalForm, 'Hybrid') || ...
            strcmp(stParameters.sFunctionalForm, 'Exponential') || ...
            strcmp(stParameters.sFunctionalForm, 'Hybrid Exponential') || ...
            strcmp(stParameters.sFunctionalForm, 'Decaying Additive
Exponential') || ...
            strcmp(stParameters.sFunctionalForm, 'Additive Exponential'))
            if (strcmp(stParameters.sDeathFunction, 'Dimensionless Projection')
|| ...
                strcmp(stParameters.sDeathFunction, 'Tunable Dimensionless
Projection') || ...
                strcmp(stParameters.sDeathFunction, '0.1 Dimensionless
Projection'))
                pCleared = 1./(1 + exp(nSlope*100*(Vr - vr50)/vr50));
            else
                pCleared = 1./(1 + exp(nSlope*(Vr - vr50)));
            end
        elseif (strcmp(stParameters.sFunctionalForm, 'Simple'))
            pCleared = (Vr < vr50);
        end
        pCleared = reshape(pCleared, size(V));
    else
        theta = atan(stParameters.hStar/stParameters.vStar);
        R = [cos(theta) sin(theta); -1*sin(theta) cos(theta)];
        Vr = R(1,:)*[V(:)'; H(:)'];
        vr50 = R(1,:)*[stParameters.v50;
stParameters.v50*stParameters.hStar/stParameters.vStar];
        if (strcmp(stParameters.sFunctionalForm, 'Hybrid') ||
strcmp(stParameters.sFunctionalForm, 'Exponential') || ...
            strcmp(stParameters.sFunctionalForm, 'Hybrid Exponential') ||
strcmp(stParameters.sFunctionalForm, 'Additive Exponential') || ...
```

FIG. 15Z

```
                strcmp(stParameters.sFunctionalForm, 'Decaying Additive
Exponential'))
            pCleared = 1./(1 + exp(nSlope*100*(Vr - vr50)/vr50));
        elseif (strcmp(stParameters.sFunctionalForm, 'Simple'))
            pCleared = (Vr < vr50);
        end
        pCleared = reshape(pCleared, size(V));
    end
end function [dP_Cleared, nCleared] = clearRBC(pCleared, P, V, H)
    % The probability of being cleared is sigmoidal (logistic).
    pCleared = repmat(pCleared(:), 1, size(P, 2));

% Keep track of how many (probability density) are cleared.
    dP_Cleared = pCleared.*P;
    nCleared = sum(dP_Cleared);
end function [spLaplacian, L] = getLaplacian(stParameters, nVar, ixTopRight,
ixBottomRight, ixBottomLeft, ixTopLeft, ...
        ixRightEdge, ixTopEdge, ixLeftEdge, ixBottomEdge, ixInterior, ixVStep)

Lv = -2*speye(nVar);
    Lv(ixTopRight, [(ixTopRight - ixVStep)]) = 1;
    Lv(ixBottomRight, [(ixBottomRight - ixVStep)]) = 1;
    Lv(ixBottomLeft, [(ixBottomLeft + ixVStep)]) = 1;
    Lv(ixTopLeft, [(ixTopLeft + ixVStep)]) = 1;

for ix = 1:length(ixRightEdge)
        Lv(ixRightEdge(ix), [(ixRightEdge(ix) - ixVStep)]) = 1;
    end
    for ix = 1:length(ixTopEdge)
        Lv(ixTopEdge(ix), [(ixTopEdge(ix) - ixVStep) (ixTopEdge(ix) + ixVStep)])
= 1;
    end
    for ix = 1:length(ixLeftEdge)
        Lv(ixLeftEdge(ix), [(ixLeftEdge(ix) + ixVStep)]) = 1;
    end
    for ix = 1:length(ixBottomEdge)
        Lv(ixBottomEdge(ix), [(ixBottomEdge(ix) - ixVStep) (ixBottomEdge(ix) +
ixVStep)]) = 1;
    end
    for ix = 1:length(ixInterior)
        Lv(ixInterior(ix), [(ixInterior(ix) - ixVStep) (ixInterior(ix) +
ixVStep)]) = 1;
    end
    Lv = stParameters.Dv*Lv/(stParameters.nMeshWidth^2);

Lh = -2*speye(nVar);
    Lh(ixTopRight, [(ixTopRight + 1)]) = 1;
    Lh(ixBottomRight, [(ixBottomRight - 1)]) = 1;
    Lh(ixBottomLeft, [(ixBottomLeft - 1)]) = 1;
    Lh(ixTopLeft, [(ixTopLeft + 1)]) = 1;

for ix = 1:length(ixRightEdge)
        Lh(ixRightEdge(ix), [(ixRightEdge(ix) + 1) (ixRightEdge(ix) - 1)]) = 1;
    end
    for ix = 1:length(ixTopEdge)
        Lh(ixTopEdge(ix), [(ixTopEdge(ix) + 1)]) = 1;
```

FIG. 15AA

```
        end
        for ix = 1:length(ixLeftEdge)
            Lh(ixLeftEdge(ix), [(ixLeftEdge(ix) + 1) (ixLeftEdge(ix) - 1)]) = 1;
        end
        for ix = 1:length(ixBottomEdge)
            Lh(ixBottomEdge(ix), [(ixBottomEdge(ix) - 1)]) = 1;
        end
        for ix = 1:length(ixInterior)
            Lh(ixInterior(ix), [(ixInterior(ix) + 1) (ixInterior(ix) - 1)]) = 1;
        end
        Lh = stParameters.Dh*Lh/(stParameters.nMeshWidth^2);

L = Lv + Lh;
        spLaplacian = spones(L);
    end function [spJacobian, J] = getJacobian(stParameters, mVDot, mHDot, ...
            ixTopRight, ixBottomRight, ixBottomLeft, ixTopLeft, ixRightEdge,
    ixTopEdge, ixLeftEdge, ixBottomEdge, ixInterior, ixVStep)

Jv = -1*speye(numel(mVDot));
        Jh = -1*speye(numel(mVDot));

%%% Jv
        %Jv(ixTopRight, []);
        %Jv(ixBottomRight, []);
        Jv(ixBottomLeft, [(ixBottomLeft + ixVStep)]) = 1;
        Jv(ixTopLeft, [(ixTopLeft + ixVStep)]) = 1;
        % Jv(ixRightEdge, []);
        for ix = 1:length(ixTopEdge)
            Jv(ixTopEdge(ix), [(ixTopEdge(ix) + ixVStep)]) = 1;
        end
        for ix = 1:length(ixLeftEdge)
            Jv(ixLeftEdge(ix), [(ixLeftEdge(ix) + ixVStep)]) = 1;
        end
        for ix = 1:length(ixBottomEdge)
            Jv(ixBottomEdge(ix), [(ixBottomEdge(ix) + ixVStep)]) = 1;
        end
        for ix = 1:length(ixInterior)
            Jv(ixInterior(ix), [(ixInterior(ix) + ixVStep)]) = 1;
        end
        Jv = Jv.*(repmat(mVDot(:)', size(Jv, 1), 1));
        Jv = Jv/stParameters.nMeshWidth;

%%% Jh
        %Jh(ixTopRight, []);
        %Jh(ixTopLeft, []);
        Jh(ixBottomLeft, [(ixBottomLeft - 1)]) = 1;
        Jh(ixBottomRight, [(ixBottomRight - 1)]) = 1;
        %Jh(ixTopEdge, []);
        for ix = 1:length(ixRightEdge)
            Jh(ixRightEdge(ix), [(ixRightEdge(ix) - 1)]) = 1;
        end
        for ix = 1:length(ixLeftEdge)
            Jh(ixLeftEdge(ix), [(ixLeftEdge(ix) - 1)]) = 1;
        end
        for ix = 1:length(ixBottomEdge)
            Jh(ixBottomEdge(ix), [(ixBottomEdge(ix) - 1)]) = 1;
        end
        for ix = 1:length(ixInterior)
            Jh(ixInterior(ix), [(ixInterior(ix) - 1)]) = 1;
```

FIG. 15BB

```
    end
    Jh = Jh.*(repmat(mHDot(:)', size(Jh, 1), 1));
    Jh = Jh/stParameters.nMeshWidth;

J = Jv + Jh;
    J = -1*J;

spJacobian = spones(J);
end function dv_dt = vdot(stParameters, V, H)
    dV = getVDistance(stParameters, V, H);
    if (strcmp(stParameters.sFunctionalForm, 'Hybrid'))
        dv_dt = -1*stParameters.alphav*stParameters.vStar*...
            exp(stParameters.betav*(dV));
    elseif (strcmp(stParameters.sFunctionalForm, 'Exponential'))
        dv_dt = -1*(stParameters.alphav*V).*...
            max(1, stParameters.betav*(dV));
    elseif (strcmp(stParameters.sFunctionalForm, 'Piecewise'))
        deltaV = max(0, dV);
        nFast = min(zeros(size(deltaV)), deltaV -
stParameters.nCVMarrowVolume)*stParameters.betav;
        nSlow = max(deltaV, stParameters.nCVMarrowVolume)*stParameters.betav/4;
        dv_dt = -1*stParameters.alphav*(stParameters.vStar/stParameters.hStar)*(1
+ nFast + nSlow);
    elseif (strcmp(stParameters.sFunctionalForm, 'Simple'))
        dv_dt = -1*stParameters.alphav*stParameters.vStar*...
            max(1, stParameters.betav*(dV));
    elseif (strcmp(stParameters.sFunctionalForm, 'Additive Exponential'))
        dv_dt = -1*stParameters.alphav*V - stParameters.betav*(max(0, dV));
    elseif (strcmp(stParameters.sFunctionalForm, 'Decaying Additive
Exponential'))
        mNorm = (V.^2 + H.^2).^(1/2);
        starNorm = sqrt(stParameters.vStar^2 + stParameters.hStar^2);
        dv_dt = -1*stParameters.alphav*V.*exp(stParameters.alphaDecay*(mNorm -
starNorm)/starNorm) - stParameters.betav*(max(0, dV));
    elseif (strcmp(stParameters.sFunctionalForm, 'Hybrid Exponential'))
        dv_dt = -1*stParameters.alphav*V.*...
            exp(stParameters.betav*(dV));
    end
end function dV = getVDistance(stParameters, V, H)
    if (strcmp(stParameters.sOptimalTrend, 'Quasi-linear'))
        a = stParameters.oQuasiLinearFit.a;
        b = stParameters.oQuasiLinearFit.b;
        dV = (V - (H - b)/a)/stParameters.vStar;
    else
        dV = V/stParameters.vStar - H/stParameters.hStar;
    end
end function dh_dt = hdot(stParameters, V, H)
    dH = getHDistance(stParameters, V, H);
    if (strcmp(stParameters.sFunctionalForm, 'Hybrid'))
        dh_dt = -1*stParameters.alphah*stParameters.hStar*...
            exp(stParameters.betah*(dH));
    elseif (strcmp(stParameters.sFunctionalForm, 'Exponential'))
        dh_dt = -1*(stParameters.alphah*H).*...
            max(1, stParameters.betah*(dH));
    elseif (strcmp(stParameters.sFunctionalForm, 'Piecewise'))
```

FIG. 15CC

```
        deltaH = max(0, dH);
        nFast = min(zeros(size(deltaH)), deltaH -
stParameters.nCVMarrowHb)*stParameters.betah;
        nSlow = max(deltaH, stParameters.nCVMarrowHb)*stParameters.betah/4;
        dh_dt = -1*stParameters.alphah*(stParameters.vStar/stParameters.hStar)*(1
+ nFast + nSlow);
    elseif (strcmp(stParameters.sFunctionalForm, 'Simple'))
        dh_dt = -1*stParameters.alphah*stParameters.hStar*...
            max(1, stParameters.betah*(dH));
    elseif (strcmp(stParameters.sFunctionalForm, 'Additive Exponential'))
        dh_dt = -1*stParameters.alphah*H - stParameters.betah*(max(0, dH));
    elseif (strcmp(stParameters.sFunctionalForm, 'Decaying Additive
Exponential'))
        mNorm = (V.^2 + H.^2).^(1/2);
        starNorm = sqrt(stParameters.vStar^2 + stParameters.hStar^2);
        dh_dt = -1*stParameters.alphah*H.*exp(stParameters.alphaDecay*(mNorm -
starNorm)/starNorm) - stParameters.betah*(max(0, dH));
    elseif (strcmp(stParameters.sFunctionalForm, 'Hybrid Exponential'))
        dh_dt = -1*stParameters.alphah*H.*...
            exp(stParameters.betah*(dH));
    end
end function dH = getHDistance(stParameters, V, H)
    if (strcmp(stParameters.sOptimalTrend, 'Quasi-linear'))
        a = stParameters.oQuasiLinearFit.a;
        b = stParameters.oQuasiLinearFit.b;
        dH = (H - (V*a + b))/stParameters.hStar;
    else
        dH = H/stParameters.hStar - V/stParameters.vStar;
    end
end function [x, resnorm, output, jacobian, stParameters] = optFDPDF(vData, hcData,
stParameters)
    if (nargin == 2)
        stParameters = getRBCPDFParameters();
    end bMatchParameters = stParameters.bMatchParameters;
    bPenalizeFalsePositives = stParameters.bPenalizeFalsePositives;

% Use an empirical target distribution.
    [Phat, P_empirical, vi, hi] = makeEmpiricalPDF(vData, hcData);
    ixCells = find(Phat > 5);
    nCells = sum(Phat(ixCells));
    nCells = sum(Phat(:));
    stParameters.df = numel(ixCells);
    [r_targ, mu_v_targ, rdw_targ, mu_h_targ, hdw_targ] = computeRBCCorr(Phat(:)',
vi, hi);
    mu_age_targ = stParameters.muAgeTarg;
    vTarget = [r_targ , ...
        mu_v_targ, ...
        rdw_targ, ...
        mu_h_targ, ...
        hdw_targ, ...
        mu_age_targ];

if (strcmp(stParameters.sOptimalTrend, 'Quasi-linear'))
        x0 = [stParameters.alphav, ...
            stParameters.betav, ...
```

FIG. 15DD

```
            stParameters.betah, ...
            stParameters.v50, ...
            stParameters.Dv, ...
            stParameters.Dh, ...
            stParameters.alphah];
    else
        x0 = [stParameters.alphav, ...
            stParameters.betav, ...
            stParameters.betah, ...
            stParameters.v50, ...
            stParameters.Dv, ...
            stParameters.Dh];
    end
    if (strcmp(stParameters.sDeathFunction, 'Tunable Dimensionless Projection'))
        x0 = [x0, stParameters.nSlope];
    end
    if (strcmp(stParameters.sFunctionalForm, 'Decaying Additive Exponential'))
        x0 = [x0, stParameters.alphaDecay];
    end resnorm = [];
    jacobian = [];
    lb = zeros(size(x0));
    ub = inf(size(x0));
    if (~isnan(stParameters.nMinAlpha))
        lb(1) = stParameters.nMinAlpha;
        ub(1) = stParameters.nMaxAlpha;
    end if (strcmp(stParameters.sOptimizer, 'lsqnonlin'))
        optset = optimset('Display', 'iter', 'TolFun', 1e-15, 'TolX', 1e-15);
        %optset = optimset('Display', 'iter');
        [x,resnorm,residual,exitflag,output,lambda,jacobian] =
lsqnonlin(@nestedfun, x0, lb, ub, optset);
    elseif (strcmp(stParameters.sOptimizer, 'patternsearch'))
        if (stParameters.bParallel)
            optset = psoptimset('Display', 'diagnose', 'CompletePoll', 'on',
'UseParallel', 'always');
        else
            optset = psoptimset('Display', 'diagnose');
        end
        [x, resnorm, exitflag, output] = patternsearch(@nestedfun, x0, [], [],
[], [], lb, ub, [], optset);
    else
        optset = optimset('Display', 'iter', 'MaxFunEvals', 1000, 'TolFun', 1e-
2);
        [x,resnorm,exitflag,output] = fminsearch(@nestedfun, x0, optset);
    end % Nested function that computes the objective function
    function y = nestedfun(x)

% Setup the parameters.
        disp(x);
        stParameters.alphav = x(1); % Rate of translation down the "optimal" HC
ratio.
        bQuasiLinear = strcmp(stParameters.sOptimalTrend, 'Quasi-linear');
        if (bQuasiLinear)
            stParameters.alphah = x(7); % Rate of translation down the "optimal"
HC ratio.
        else
```

FIG. 15,EE

```
            stParameters.alphah = x(1); % Rate of translation down the "optimal"
HC ratio.
        end
        stParameters.betav = x(2); % Rate of movement toward the "optimal" ratio.
        stParameters.betah = x(3); % Rate of movement toward the "optimal" ratio.
        stParameters.v50 = x(4); % Volume where P(clearance) = 50%.
        stParameters.Dv = x(5);
        stParameters.Dh = x(6);

bTunable = strcmp(stParameters.sDeathFunction, 'Tunable Dimensionless
Projection');
        bDecaying = strcmp(stParameters.sFunctionalForm, 'Decaying Additive
Exponential');

if (bTunable)
            stParameters.nSlope = x(7 + bQuasiLinear);
        end
        if (bDecaying)
            stParameters.alphaDecay = x(7 + bQuasiLinear + bTunable);
        end % Simulate the evolution to steady state.
        [P, t, V, H, tParameters] = fdRBC(stParameters);
        if (stParameters.nDays)
            % Calculate the steady state parameters.
            [mBirthAlive, vMeanAge, Pf] = computeAgeDistribution(P);
            muAge = vMeanAge(end);
        else
            [Pf, A, muAge] = ssRBC(tParameters.J, tParameters.L, tParameters.P_0,
tParameters.pCleared);
            Pf = Pf(:)';
        end
        [r, mu_v, cv_v, mu_h, cv_h] = computeRBCCorr(Pf, V, H);
        stParameters.r = r;
        stParameters.mcv = mu_v;
        stParameters.mch = mu_h;
        stParameters.rdw = cv_v;
        stParameters.hdw = cv_h;
        stParameters.muAge = muAge;

vEstimate = [r, ...
            mu_v, ...
            cv_v, ...
            mu_h, ...
            cv_h, ...
            muAge];

if (bMatchParameters)
            % Try to match the parameters of the empirical distribution.
            vResiduals = vTarget - vEstimate;
            y = 100*(1./vTarget).*vResiduals;

% The average age is a weaker constraint.
            y(end) = y(end)/100;
        else
            % Evaluate the simulated distribution at the points in the
            % empirical distribution.
            Pf_hat = interp2(V, H, reshape(Pf, size(V)), vi, hi, 'linear', 0);
            Pf_hat = nCells*Pf_hat/sum(Pf_hat(:));
            ixCellSimulated = find(Pf_hat > 5);
            ixCellSimulatedFP = setdiff(ixCellSimulated, ixCells);
```

FIG. 15FF

```
            %nHat = sum(Pf_hat(ixCells));
            %Pf_hat = Pf_hat*(nCells/sum(Pf_hat(ixCells)));
            vResiduals = (Pf_hat(ixCells) - Phat(ixCells))./sqrt(Phat(ixCells));
            yFP = (Pf_hat(ixCellSimulatedFP) -
5)./sqrt(Pf_hat(ixCellSimulatedFP));
            y = [vResiduals(:); (numel(vResiduals)/10)*(mu_age_targ -
muAge)/sqrt(mu_age_targ)];
            if (bPenalizeFalsePositives)
                yFP = (Pf_hat(ixCellSimulatedFP) -
5)./sqrt(Pf_hat(ixCellSimulatedFP));
                y(end) = y(end) + norm(yFP)^2;
            end
            %norm(vResiduals)^2
            %[h, p, stats] = chi2gof(Pf_hat(ixCells), 'expected',
            %P_empirical(ixCells));
            %comparePDFs(Pf_hat, Phat, vi, hi);
        end
        disp(sprintf('df(%d); r: %0.2f (=> %0.2f); MCV: %0.2f (=> %0.2f); RDW:
%0.2f (=> %0.2f); MCH: %0.2f (=> %0.2f); HDW: %0.2f (=> %0.2f); muAge: %0.2f (=>
%0.2f)', ...
            numel(vResiduals), r, r_targ, mu_v, mu_v_targ, cv_v, rdw_targ, mu_h,
mu_h_targ, cv_h, hdw_targ, muAge, mu_age_targ));
        if (~strcmp(stParameters.sOptimizer, 'lsqnonlin'))
            y = norm(y)^2;
            if (strcmp(stParameters.sOptimizer, 'fminsearch'))
                lbPenalty = any(x < lb);
                ubPenalty = any(x > ub);
                y = y + 1e7*(lbPenalty + ubPenalty);
            end
        end
    end
end
```

FIG. 15GG

```
function [Pf, A, muAge] = ssRBC(J, L, P_0, pCleared)
    % Make a sparse diagonal from pCleared.
    spD = sparse(numel(pCleared));
    for ix = 1:numel(pCleared)
        spD(ix,ix) = pCleared(ix);
    end A = (L + J - spD);
    Pf = -1*A\(P_0(:));
    nMin = min(Pf(:));
    if (nMin < -eps)
        Pf = Pf + abs(nMin);
    end
    muAge = sum(Pf)/2;
end
```

FIG. 16

```
function [p, u] = calculateCompensation(sFCS, bPlot, nVersion, bRetic)
    if (nargin < 3)
        bRetic = 0;
        nVersion = 3;
        if (nargin < 2)
            bPlot = 0;
            if (nargin < 1)
                sFCS = getFCS();
            end
        end
    end % Load the FCS.
    p = [];
    for ix = 1:size(sFCS, 1)
        [nMCV, nRDW, nMCH, nHDW, nRho, v, hc, nVersion] = compareMieTransforms(sFCS{ix}, nVersion);

if (bRetic == 3)
            [f, nMCV, nRDW, nMCH, nHDW, nRho, v, hc, nVersion] = estimateReticFraction(sFCS{ix}, nVersion);
        end
        % Get the empirical retics and steady state.
        [Phat, P, vi, hi] = makeEmpiricalPDF(v, hc);

h = v.*hc/100;
        %vi = vi/(Phat(:)'*vi(:)/sum(Phat(:)));
        %hi = hi/(Phat(:)'*hi(:)/sum(Phat(:)));
        %v = v/mean(v);
        %h = h/mean(h);

if (bPlot)
            %figure;
            if (bRetic == 2)
                cColor = 'r';
            else
                cColor = 'b';
            end
            plotContourFit(vi, hi, Phat, cColor, bRetic);
        end % Transform.
        bRotateAndScale = 1;
        if (bRotateAndScale)
            theta = -atan(nMCH/nMCV);
            u = v*cos(theta) - h*sin(theta);
            w = v*sin(theta) + h*sin(theta);

ui = vi*cos(theta) - hi*sin(theta);
            wi = vi*sin(theta) + hi*cos(theta);
        else
            % Project, rotate, and scale;
            theta = atan(nMCH/nMCV);

p1 = [cos(theta)^2; sin(theta)*cos(theta)];
            p2 = [sin(theta)*cos(theta); sin(theta)^2];
            P = [p1 p2];
```

FIG. 17A

```
            theta = -1*theta;
            r1 = [cos(theta); sin(theta)];
            r2 = [-1*sin(theta); cos(theta)];
            R = [r1 r2];
            u = R*P*[v'; h'];
            v = u(2,:)';
            u = u(1,:)';
        end tp = [sum([u u u u u u u] < repmat([.70 0.75 0.79 0.82 0.85 0.90 0.95
1]*mean(u), numel(u), 1))/numel(u)];

ixLow = find(u < median(u));
        nLowVar = sqrt(sum(((u(ixLow) - median(u)).^2)/numel(ixLow)));
        tp = [tp nLowVar];
        p = [p; tp];
    end
end function sFCS = getFCS()
    sODBC = 'microcytosis';
    r = [];
    conn = database(sODBC, '', '');

%curs = exec(conn, ['select [RBC FCS File] from AdviaFile where [Diagnosis] =
''normalTrain''']);
    curs = exec(conn, ['select [RBC FCS File] from AdviaFile where [Diagnosis] =
''ironTest''']);
    curs = fetch(curs);
    sFCS = curs.Data;

close(conn);

if 0
    figure
    ix = 8;
    subplot(211)
    hist(mNorm(:,ix),20)
    xl1 = get(gca,'xlim')
    subplot(212)
    hist(mIron(:,ix))
    xl2 = get(gca,'xlim')
    set(gca,'xlim',[min(xl1(1), xl2(1)) max(xl1(2), xl2(2))]);
    subplot(211);
    set(gca,'xlim',[min(xl1(1), xl2(1)) max(xl1(2), xl2(2))]);
end
end
```

FIG. 17B

RED BLOOD CELL DYNAMICS FOR ADMINISTERING TREATMENT FOR IRON-DEFICIENCY ANEMIA

CLAIM OF PRIORITY

This application is a U.S. National Phase Application under 35 U.S.C. § 371 of International Patent Application No. PCT/US2011/052038, filed on Sep. 16, 2011, which claims the benefit of U.S. Provisional Patent Application Ser. No. 61/383,357, filed on Sep. 16, 2010, all of which are incorporated herein by reference in their entireties.

FEDERALLY SPONSORED RESEARCH OR DEVELOPMENT

This invention was made with Government support under Grant Nos. DK083242 and HL091331 awarded by the National Institutes of Health. The Government has certain rights in the invention.

TECHNICAL FIELD

This invention relates to methods for identifying patients with anemia or pre-anemia, and distinguishing thalassemia-trait anemia from iron-deficiency anemia and from other causes of anemia. The methods can also be used to optimize treatment, e.g., therapy with iron supplements and/or erythropoiesis-stimulating agents such as erythropoietin (EPO). Also described are devices and systems, e.g., for use in the described methods.

BACKGROUND

The systems controlling the number, size, hemoglobin concentrations, and other characteristics of circulating human red blood cells (RBCs) are poorly understood. After release from the bone marrow, RBCs undergo reduction in both volume and total hemoglobin content by an unknown mechanism (Lew V L, et al. (1995) Blood 86:334-341; Waugh R E, et al. (1992) Blood 79:1351-1358); after about 120 days, responding to an unknown trigger, they are removed.

SUMMARY

Based in part on theory from statistical physics and data from the hospital clinical laboratory (d'Onofrio G, et al. (1995) Blood 85:818-823), the present invention uses a master equation model for RBC maturation and clearance. The model accurately identifies patients with anemia, and distinguishes thalassemia-trait anemia from iron-deficiency anemia. Strikingly, it also identifies many pre-anemic patients several weeks before anemia becomes clinically detectable.

In one aspect, a method of determining a subject's risk of developing iron deficiency anemia (IDA) includes including in a sample red blood cells from the subject, determining a population mean corpuscular hemoglobin concentration (MCHC), and transforming each cell's volume and hemoglobin content into an index by projecting the volume and hemoglobin content onto the MCHC line. The method also includes determining a fraction of red blood cells in the sample whose transformed volume and hemoglobin content index falls below a threshold percentage of the mean projection location on the MCHC line to provide a sample fraction, and comparing the sample fraction to a reference fraction. The presence of a sample fraction that is above the reference fraction indicates that the subject is at risk of developing IDA.

In another aspect, a method of screening or selecting a subject for screening for a gastrointestinal (GI) disorder includes including in sample red blood cells from the subject, determining a population mean corpuscular hemoglobin concentration (MCHC), and transforming each cell's volume and hemoglobin content into an index by projecting the volume and hemoglobin content onto the MCHC line. The method also includes determining a fraction of red blood cells in the sample whose transformed volume and hemoglobin content index falls below a threshold percentage of the mean projection location on the MCHC line, and comparing the sample fraction to a reference fraction. The method further includes selecting the subject for GI evaluation or further screening if the sample fraction is below the reference fraction.

In another aspect, the disclosure features a method of making a differential diagnosis between iron deficiency anemia (IDA) and thalassemia trait (TT) in a subject who has microcytic anemia, e.g., a subject who does not have a chronic disease. The method includes determining a value for the magnitude of variation in the rate of hemoglobin content reduction ($D_h$) among cells in a sample of red blood cells from the subject, and comparing $D_h$ to a reference value. The presence of a $D_h$ that is above the reference value indicates that the subject has or is more likely to have IDA, and the presence of a Dh that is below the reference value indicates that the subject has or is more likely to have TT.

In another aspect a method for detecting the presence or use of blood doping or erythropoietic stimulant agents in a normal subject includes determining values for one or both of magnitude of variation in the rate of hemoglobin content reduction ($D_h$) and magnitude of variation in the rate of cell volume reduction ($D_v$) in a sample from the subject. The presence of $D_h$ and/or $D_v$ above a reference value indicates the presence or use of blood doping or using erythropoietic stimulant agents.

In another aspect, a method for optimizing dosage of erythropoietin (EPO) or other erythropoietic stimulant agents (ESA) in a subject includes determining a normalized critical volume ($v_c$) in a sample from a subject undergoing EPO or ESA treatment. The method also includes increasing the dose of EPO if the vc is below a lower reference level, or decreasing the dose of EPO if the vc is above an upper reference level.

In another aspect a method for treating a subject with iron includes determining the normalized critical volume ($v_c$) in a sample from a subject, and if the $v_c$ is below a lower reference level, administering a dose of iron or prescribing a course of iron supplementation.

In another aspect, the disclosure features a system that includes a computing device including a memory for storing instructions and one or more processors or processing devices capable of executing the stored instructions. The stored instructions, when executed, perform operations that include receiving data representative of the volume and hemoglobin concentration or content in each cell in the sample, and transforming each cell's volume and hemoglobin content into an index by projecting the volume and hemoglobin content onto a line representing mean red blood cell hemoglobin concentration (MCHC). Operations also include calculating a fraction of red blood cells in the sample whose transformed volume and hemoglobin content index falls below a threshold percentage of the mean projection, and providing an output representing the fraction.

In another aspect, the disclosure features one or more machine-readable storage devices configured to store instructions that are executable by one or more processors or processing devices. The instructions, when executed by the one or more processors perform operations including receiving data representative of volume and hemoglobin concentration in each cell in the sample, and transforming each cell's volume and hemoglobin content into an index by projecting the volume and hemoglobin content onto a line representing mean red blood cell hemoglobin concentration (MCHC). The operations also include calculating a fraction of red blood cells in the sample whose transformed volume and hemoglobin content index falls below a threshold percentage of the mean projection, and providing an output representing the fraction.

In another aspect, the disclosure features one or more machine-readable storage devices that include machine readable instructions to calculate one or more of the following:
(i) a population mean corpuscular hemoglobin concentration (MCHC), transformation of each cell's volume and hemoglobin content into an index by projecting the volume and hemoglobin content onto the MCHC line, and a fraction of red blood cells in the sample whose mean projection falls below a threshold percentage of the mean projection, (ii) a magnitude of variation in the rate of hemoglobin content reduction ($D_h$), (iii) a magnitude of variation in the rate of cell volume reduction ($D_v$), and (iv) a normalized critical volume or clearance threshold ($v_c$).

In another aspect a method of screening patients for thalassemia trait (TT) includes determining a value for the magnitude of variation in the rate of hemoglobin content reduction ($D_h$) in a sample from the subject, and comparing $D_h$ to reference a range. The presence of a $D_h$ that is outside the reference range indicates that the patient has or is likely to have TT and/or selecting the subject for genotyping or additional testing if the $D_h$ is outside the reference range, or if the subject is a pregnant woman, selecting the father for screening.

In another aspect, the disclosure features methods for making a differential diagnosis between anemia of chronic disease (ACD) and other causes of anemia, in a subject who has anemia (e.g., has been diagnosed with anemia). The method includes determining a value for one or more of the following: (i) the magnitude of variation in the rate of hemoglobin content reduction ($D_h$), (ii) a magnitude of variation in the rate of cell volume reduction ($D_v$), (iii) a normalized critical volume or clearance threshold ($v_c$), (iv) an average rate of slow-phase volume and hemoglobin content reduction ($\alpha$), (v) an average rate of fast-phase volume reduction ($\beta_v$), and (vi) an average rate of fast-phase hemoglobin content reduction ($\beta_h$); comparing these values to reference ranges, wherein the probability of a diagnosis of ACD is determined by the number of values within the reference range; comparing this probability to a threshold; and if the probability is above the threshold, choosing against transfusion therapy and/or choosing not to perform additional testing of iron levels.

In another aspect, the disclosure features a computer readable storage device configured to store computer readable instructions, which when executed by one or more processors cause operations including receiving a first set of parameters related to a time dependent, joint volume-hemoglobin distribution of reticulocytes or red blood cells and estimating a steady state distribution of red blood cells based on the first set of parameters. The operations also include calculating an objective function representing an extent of dissimilarity between the estimated steady state distribution and an empirical distribution of red blood cells.

In another aspect, the disclosure features a system that includes a computing device. The computing device includes a memory for storing instructions, and a detection module including one or more processors or processing devices capable of executing the stored instructions to perform various operations. The operations include receiving a first set of parameters related to a time dependent, joint volume-hemoglobin distribution of reticulocytes or red blood cells and estimating a steady state distribution of red blood cells based on the first set of parameters. The operations also include calculating an objective function representing an extent of dissimilarity between the estimated steady state distribution and an empirical distribution of red blood cells.

In another aspect, a computer implemented method includes receiving a first set of parameters related to a time dependent, joint volume-hemoglobin distribution of reticulocytes or red blood cells and estimating a steady state distribution of red blood cells based on the first set of parameters. The method also includes calculating an objective function representing an extent of dissimilarity between the estimated steady state distribution and an empirical distribution of red blood cells.

Implementations of the above methods, systems and computer readable storage devices can include any combination of the following features.

The dose of EPO can be adjusted to maintain a $v_c$ greater than 75%; or a $v_c$ between 78-82%, of the population mean volume ($\bar{v}$) in the subject. The dose of iron can be adjusted to maintain a $v_c$ greater than 78%; or a $v_c$ between 78-82%, of the population mean volume ($\bar{v}$) in the subject. The threshold percentage can be 70%, 75%, 80%, 85%, 90%, or 95% of the population mean projection on the MCHC line. The reference fraction is about 0.10, 0.11, 0.12, 0.13, 0.14, or 0.15. The sample can include whole blood from the subject. Data representative of mean red blood cell hemoglobin concentration (MCHC) in the sample can be received. A detection module can be configured to detect one or more, e.g., all, of red blood cell (RBC) cell volume (CV), mean cell volume (MCV), cell hemoglobin concentration (CHC), mean cell hemoglobin concentration (MCHC), and the mean cell hemoglobin content (MCH), as well as their population statistics. The volume and hemoglobin content of individual cells can be transformed such that the volume and hemoglobin content coordinates are projected onto the line representing the least-squares linear fit of all volume and hemoglobin content coordinates.

The computer or machine readable storage devices can include instructions to calculate one or more of: (i) a magnitude of variation in the rate of hemoglobin content reduction ($D_h$), (ii) a magnitude of variation in the rate of cell volume reduction ($D_v$), (iii) a normalized critical volume or clearance threshold ($v_c$), (iv) an average rate of slow-phase volume and hemoglobin content reduction ($\alpha$), (v) an average rate of fast-phase volume reduction ($\beta_v$), and (vi) an average rate of fast-phase hemoglobin content reduction ($\beta_h$).

The first set of parameters can be adjusted if a value of the objective function satisfies a predetermined threshold condition, to provide a second set of parameters. The second set of parameters is such that the extent of dissimilarity between a corresponding estimated steady state distribution and the empirical distribution is reduced. The second set of parameters can be provided to the one or more processors as the first set of parameters. The time dependent, joint volume-hemoglobin distribution of reticulocytes or red blood cells can be based on a blood sample obtained from a patient. The steady state distribution can be estimated based on a combination of linear operators and a measured state of the distribution. The linear operators can include at least one Jacobian and at least one Laplacian.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

In FIG. 1A, the reticulocyte distribution is shown as solid lines in the iso-probability density contours and the population of all RBCs as dashed lines. The diagonal line projecting to the origin in both panels represents the average intracellular hemoglobin concentration (MCHC) in the population. An RBC located anywhere on this line will have an intracellular hemoglobin concentration equal to the MCHC. Fast dynamics ($\beta$) first reduce volume and hemoglobin for the typical large immature reticulocytes shown in the top right of each panel. Slow dynamics ($\alpha$) then reduce volume and hemoglobin along the MCHC line. Because biological processes are inherently noisy, small random variations during the events required for reduction of volume and hemoglobin may cause individual cellular hemoglobin concentrations to drift about the MCHC line, fluctuating with magnitude (D) around the MCHC line as shown in the inset to FIG. 1B until reaching a critical volume ($v_c$ in FIG. 1B) when cells are removed.

FIG. 3A shows a normal CBC measured 116 days prior to the patient's presentation with IDA. The calculated $P_{0.85}$ (filled gray) is normal. FIG. 3B shows the normal CBC measured 65 days later and 51 days prior to detection of IDA. $P_{0.85}$ is abnormal even though the CBC is normal. Panel FIG. 3C shows the CBC at the time IDA was diagnosed.

FIG. 6A shows a view projected on vertical plane through the MCHC line (see FIG. 1). FIG. 6B shows a 90-degree rotated view looking toward the origin.

FIG. 7 shows that all model parameters have well-defined optimal neighborhoods. See equation 5 for objective function.

FIGS. 8B-8D are histograms showing the distributions of $P_{0.85}$ (8B), $P_{0.75}$ (8C), and $P_{0.90}$ (8D) for the steady state healthy subjects (top panel in each figure) and IDA subjects (bottom panel in each figure) shown in FIG. 2.

FIGS. 9A-9C show velocity fields for three of the different functional forms of single-RBC volume and hemoglobin content dynamics as listed in Table 1A-B. The black diagonal line shows constant hemoglobin concentration equal to MCHC.

FIGS. 10A-B are 3D graphs showing clearance probabilities for two of the different clearance functions described in Table 1A-B. FIG. 10A, functional forms A and C; FIG. 10B, functional form B. The MCHC line is shown in black.

FIG. 15 is an exemplary computer code for the program to infer the model parameters from the volume and hemoglobin content measurements for a patient blood sample.

FIG. 16 is an exemplary computer code for the called function "ssRBC," which calculates the steady state RBC distribution using a numerical approximation of Equation 4.

FIG. 17 is exemplary computer code for the program "calculateCompensation" which calculates the $P_{0.85}$ for a subject blood sample. This function also calls others but can be run independently of the parameter calculating code.

DETAILED DESCRIPTION

Red blood cells are removed from the circulation through a poorly-understood process. While the specific molecular and cellular mechanisms underlying these and other RBC maturation and clearance processes are unknown, it is likely that these processes are altered in states of disease and that these alterations lead to various differences in patients with these diseases. For example, if a particular cellular characteristic, like volume or hemoglobin concentration, changes during the course of a red blood cell's time in the circulation, it is likely that the average speed of this change across the population of red blood cells from a patient with some diseases will be different from the average speed of this change across the population of red blood cells from patients without the disease.

Figure 1A:
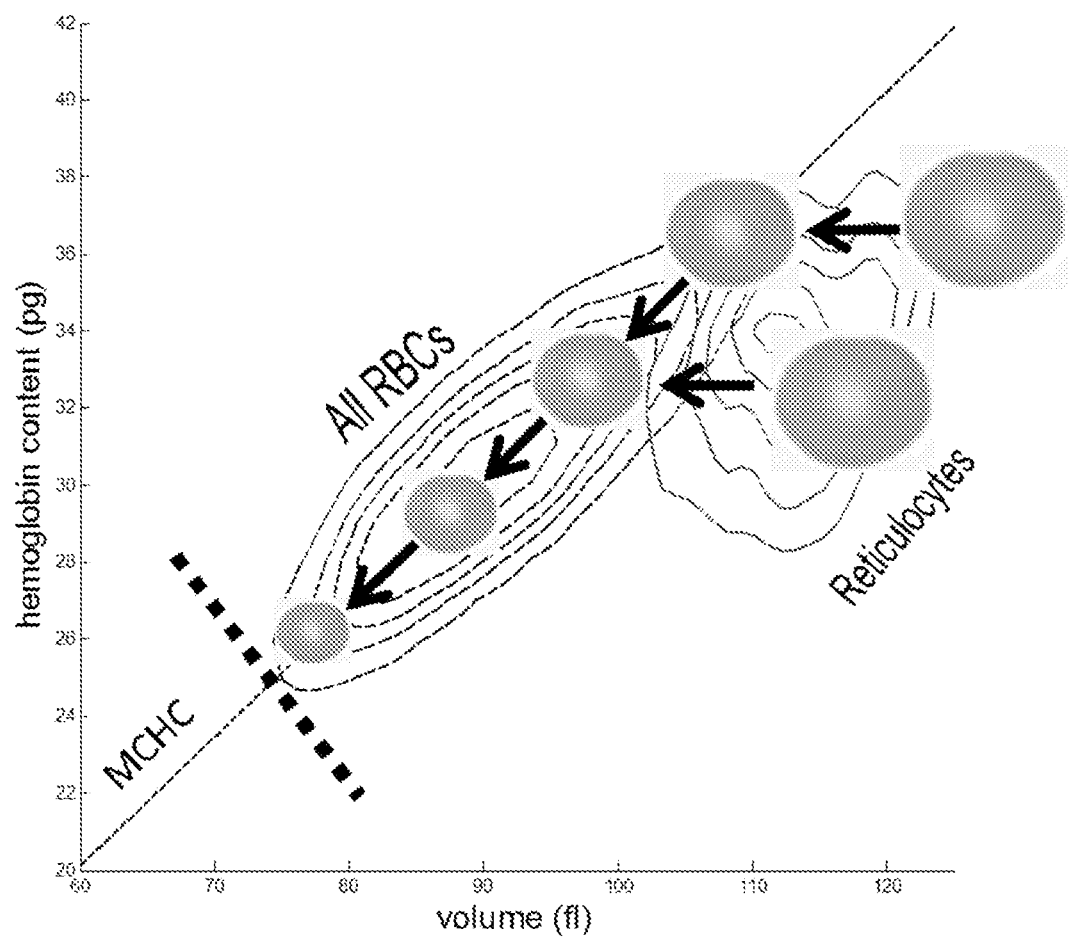
FIGS. 1A and 1B are an empirical measurement (1A) and dynamic model (1B) of co-regulation of volume and hemoglobin of an average RBC in the peripheral circulation.

In healthy human adults, about $2.5 \times 10^{11}$ new RBCs are released from the bone marrow into the peripheral circulation per day, and about the same number are cleared. The cells comprising the circulating population are thus continuously changing, but in healthy individuals (and patients with mild disease) the characteristics of the population are very stable. In the clinic, population characteristics such as the volume fraction of cells in the blood (hematocrit), the average RBC volume (MCV), the coefficient of variation in RBC volume (RDW), and the mean intracellular hemoglobin mass (MCH) are routinely measured in Complete Blood Counts (CBCs) (1). Recently, it has become possible to identify and characterize very young (hours or days old) circulating RBCs (reticulocytes) (2). RBCs undergo a rapid reduction in volume and hemoglobin in the few days after release from the bone marrow (3). This rapid phase is followed by a much longer period of slower reduction (4-7) during which volume and hemoglobin are co-regulated (8); see FIG. 1A.

A comparison of the probability distributions of reticulocytes and of all circulating RBCs (FIG. 1A) shows that the correlation between volume and hemoglobin content increases as the cells mature, from an initial correlation coefficient of about 0.40 in the reticulocyte population to about 0.85 in the full population. Thus, while many of the molecular mechanisms involved are unknown, it is clear that the average RBC matures in such a way that its hemoglobin concentration tends toward the population mean corpuscular hemoglobin concentration (MCHC), shown as an iso-concentration line in FIGS. 1A and 1B. The result of this co-regulation is that the variation in hemoglobin concentration is lower than that for volume and hemoglobin content (8).

The parameters disclosed herein show that RBCs in patients with TT and IDA remain in the periphery with much smaller volumes and lower hemoglobin contents, in both absolute and relative terms, than they would under normal conditions. Their persistence may reflect a compensatory delay in clearance in response to the less efficient erythropoiesis of these anemias. Thus, mechanisms must exist that can alter the behavior of the trigger for RBC clearance. Comparing RBC clearance in TT and IDA with that of healthy individuals or ACD patients may provide a new route to identifying the trigger. The variation in $v_c$ is much smaller than the variation in $\bar{v}$ for healthy individuals (14) suggesting that the trigger is highly correlated with position on the MCHC line.

Anemia

Anemia is a condition wherein the amount of hemoglobin present in the bloodstream is lower than normal. Anemia can be subdivided into three major groups based on the size of the red blood cells (measured as the MCV, or mean corpuscular volume). Normocytic anemia is diagnosed when the red blood cells are of normal size (i.e., 80-100 fL). Macrocytic anemia (commonly caused by B12 deficiency) is diagnosed when red blood cell size is larger than normal, i.e., an MCV of >100 fL. Microcytic anemia is when the red blood cells are smaller than normal, i.e., MCV<80 fL.

Diagnosing Pre-Anemia/Predicting Development of Anemia

Figure 3A:
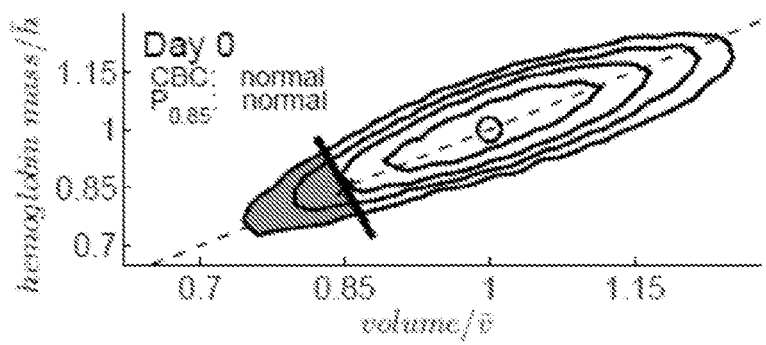
FIGS. 3A-C are contour plots of complete blood counts (CBCs) for a patient developing IDA after 4 months. Each plot shows contours enclosing 35%, 60%, 75%, and 85% of the joint volume-hemoglobin content probability density. The dashed line from the origin represents the MCHC. The circle shows the mean of the projections of each cell's volume-hemoglobin content coordinates onto the MCHC line. The short solid line perpendicular to the MCHC line marks the position along the line corresponding to 85% of the mean projection.
Figure 3B:
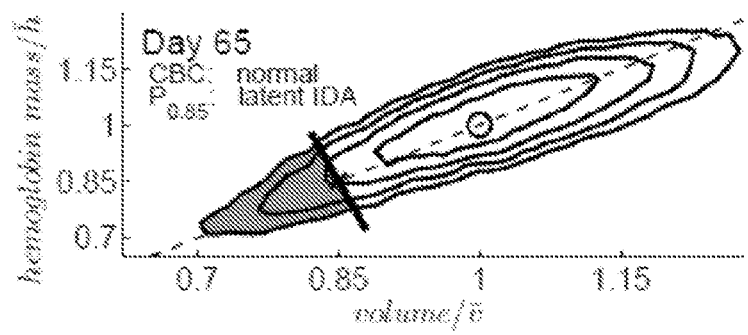
Figure 3C:
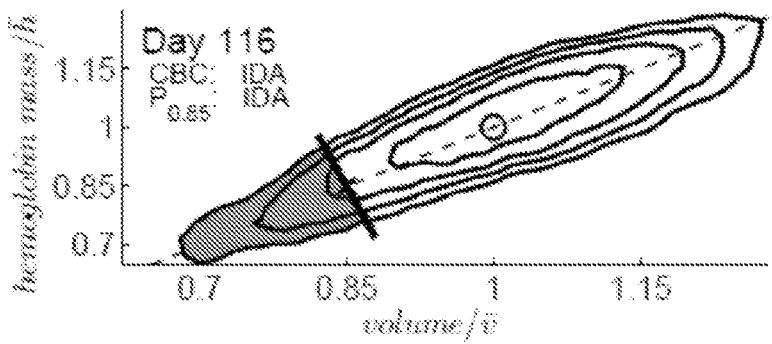
Figure 3D:
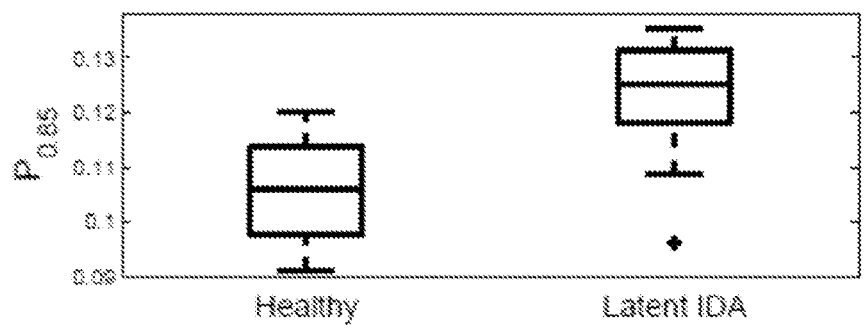
FIG. 3D shows boxplots of $P_{0.85}$ for 20 normal CBCs from patients who had a second normal CBC within 90 days and 20 normal CBCs from patients who were diagnosed with IDA up to 90 days later. $P_{0.85}$ successfully predicts IDA up to 90 days earlier than the actual diagnosis with a sensitivity of 75% and a specificity of 100%. See below and Example 3, "Predicting Iron Deficiency Anemia," for more detail.

The model and methods presented herein offer a potential way to identify patients with latent or compensated anemia before frank clinical anemia develops, by looking for signs of clearance delay. This possibility was tested in an independent set of patients who had normal CBCs followed at least 30 and no more than 90 days later by either another normal CBC or clinical IDA. For each patient sample, the (v,h) coordinates of all cells were projected onto the MCHC line and the probability density was integrated along this line below 85% of the mean ($P_{0.85}$). FIG. 3A-C shows the evolution of one patient's CBC from normal to latent IDA and ultimately to IDA. The CBC shown in the middle panel (FIG. 3B) was clinically unremarkable, but the $P_{0.85}$ was abnormal, predicting anemia that did not arise and come to medical attention for 51 days. FIG. 3D shows values of $P_{0.85}$ for 20 normal CBCs from patients who remained healthy and 20 normal CBCs from those who developed IDA between 30 and 90 days later. The value of $P_{0.85}$ predicted IDA with a sensitivity of 75% and a specificity of 100%. See Example 3, "Predicting Iron Deficiency Anemia." Current standard of care has a sensitivity of 0% in this population, because all CBCs were "normal." This model-based prediction relies on only a single CBC measurement at one point in time, in contrast to statistical regression approaches, which often rely on the integration of multiple measurements and types of information from different sources and different time points (15).

Thus, the methods described can be used to diagnose pre-anemia, or predict the development of anemia in a subject at least 30-90 days before it develops, e.g., when the subject still has an otherwise normal CBC (e.g., wherein the subject's HCT, MCV, RDW, MCH, MCHC, RBC, and HGB levels are all within normal ranges).

Normal CBC values may vary with the laboratory that performs the analysis, but in general normal values are as follows.

| Parameter | Value |
| --- | --- |
| Hematocrit (HCT) (varies with altitude) | Male: 40.7 to 50.3% Female: 36.1 to 44.3% |
| Mean Red Blood Cell Volume (MCV) | 80 to 95 femtoliters |
| Red Blood Cell Distribution Width (RDW) | 11.5-14.5% |
| Mean Cell Hemoglobin (MCH) | 27 to 31 pg/cell |
| (MCHC) | 32 to 36 gm/dL |
| Red Blood Cell (RBC) count (varies with altitude) | Male: 4.7 to 6.1 million cells/uL Female: 4.2 to 5.4 million cells/uL |
| Hemoglobin (HGB) (varies with altitude) | Male: 13.8 to 17.2 gm/dL Female: 12.1 to 15.1 gm/dL |

Figure 5:
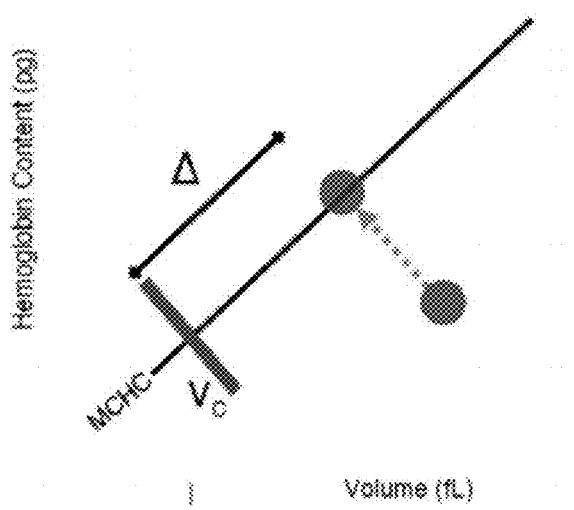
FIG. 5 is a schematic of the projected distance ($\Delta$) used to calculate the probability of clearance as described in Equation 3. The cell is projected onto the MCHC line, and the probability of clearance is a function of the distance from the projected point to a threshold ($v_c$) along this line.

The methods include determining cell volume and HGB content (e.g., HGB mass or concentration) for each cell in a sample from a subject, calculating the distribution of volume and HGB content values across all cells in the sample, calculating the transformation of each cell's volume and hemoglobin, e.g., as shown in FIG. 5, calculating the distribution of such transformations for all cells in the sample, and determining the percentage of the cells whose transformations are below a threshold level of transformed volume and HGB content, e.g., as shown in FIGS. 3A-D and 8A-D. In some embodiments, the methods include determining, e.g., in a sample comprising red blood cells from the subject, a population mean corpuscular hemoglobin concentration (MCHC); calculating the distribution of volume and HGB content values across all cells in the sample, calculating the transformation of each cell's volume and hemoglobin, e.g., as shown in FIG. 5, calculating the distribution of such transformations for all cells in the sample, determining the fraction of red blood cells in the sample whose transformations fall below a threshold percentage of the mean transformation to provide a sample fraction; and comparing the sample fraction to a reference fraction, wherein the presence of a sample fraction that is below the reference fraction indicates that the subject is at risk of developing anemia, e.g., IDA. Values for the threshold percentage and reference level can be selected using methods known in the art, and can represent values that maximize sensitivity and specificity. In some embodiments, the threshold percentage is 70%, 75%, 80%, 85%, 90%, or 95% of the population mean MCHC. In some embodiments, the reference fraction is about 0.10, 0.11, 0.12, 0.13, 0.14, or 0.15. One of skill in the art would readily be able to identify optimal threshold percentages and reference fractions using known statistical methodology.

Differential Diagnosis: Thalassemia Versus Iron Deficiency Anemia

The differential diagnosis of a microcytic anemia includes iron deficiency anemia (IDA), thalassemia trait (TT), anemia of chronic disease (ACD), and other causes of anemia.

ACD typically involves a reduction in hematocrit to no more than 20% below the lower limit of normal, normal or high ferritin, and a low or normal total iron binding capacity. If a reduced RBC clearance threshold ($v_c$) represents an adaptive physiologic response to offset the anemia, then perhaps one would expect the normal $v_c$ seen here for ACD, where the anemia itself may represent an adaptive physiologic response (18). The presence of anemia in a subject with chronic disease typically suggests a diagnosis of ACD. Chronic diseases typically associated with ACD include autoimmune disorders, e.g., Crohn's disease, systemic lupus erythematosus, rheumatoid arthritis, and ulcerative colitis; cancer, e.g., lymphoma and Hodgkin's disease; chronic kidney disease; liver disease, e.g., cirrhosis; and chronic infections, e.g., bacterial endocarditis, osteomyelitis (bone infection), HIV/AIDS, hepatitis B or hepatitis C. See, e.g., Gardner and Benz Jr., "Anemia of chronic diseases." In: Hoffman et al., eds. *Hematology: Basic Principles and Practice.* 5th ed. Philadelphia, Pa.: Elsevier Churchill Livingstone; 2008:chap 37.

IDA typically involves a reduction in hematocrit, low MCV, and low ferritin. Mild IDA typically involves a reduction in hematocrit to no more than 20% below the lower limit of normal. Patients with IDA may show historical evidence of normal MCV with normal hematocrit.

Figure 2:
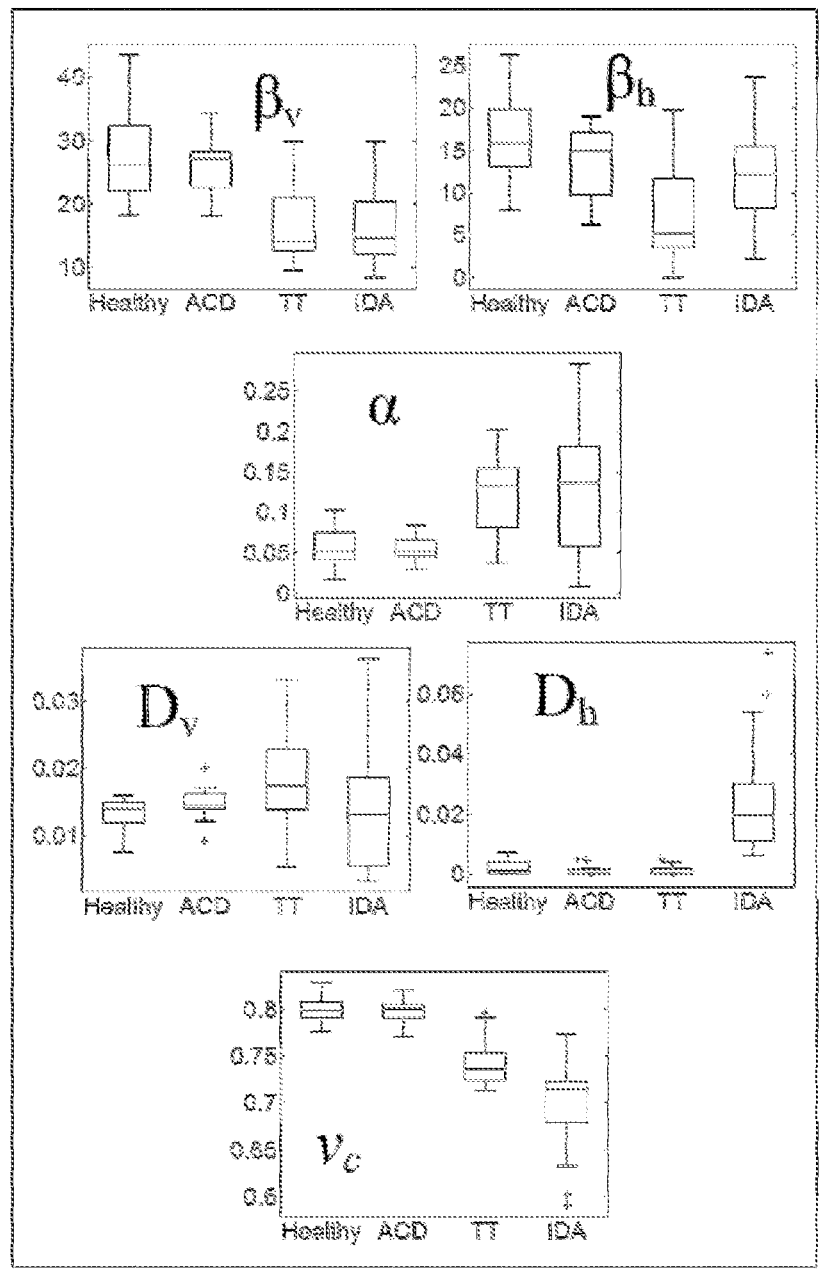
FIG. 2 is a set of six boxplots of model parameters for 20 healthy individuals and patients with three forms of mild anemia: 11 with anemia of chronic disease (ACD), 33 with thalassemia trait (TT), and 27 with iron deficiency anemia (IDA). The top and bottom edges of each box are located at the $75^{th}$ and $25^{th}$ percentiles. The median is indicated by a horizontal line in the interior of the box. Vertical lines extend to data points whose distance from the box is less than 1.5-times the inter-quartile distance. More extreme data points are shown as plus (+) symbols. The fast dynamics are characterized by $\beta$, the slow by $\alpha$, random fluctuations by D, and the clearance threshold by $v_c$.
Figure 4:
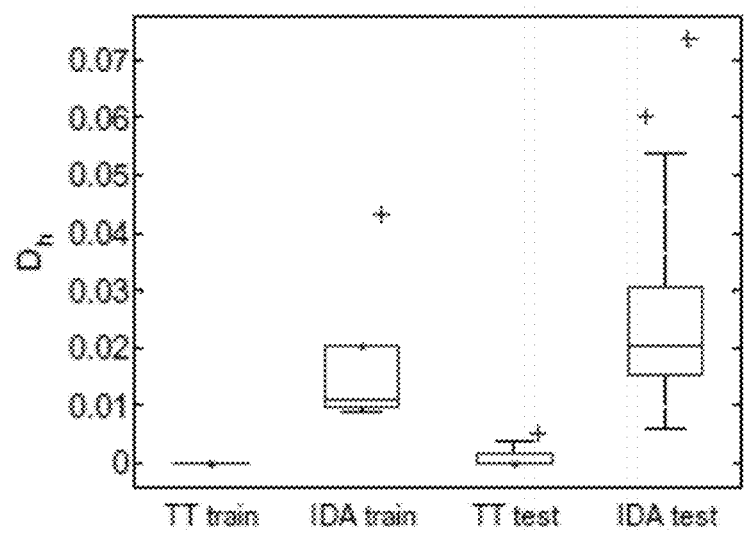
FIG. 4 is a box plot showing the distributions of $D_h$ for 5 training cases with TT, 5 training cases with IDA, 28 test cases with TT, and 22 test cases with IDA. The results illustrate the ability of the present methods to differentiate between TT and IDA as causes of microcytic anemia.

TT is typically associated with either a high hemoglobin A2 fraction, or with the presence of one or more alpha globin gene mutations. TT often involves a reduction in hematocrit usually to no more than 20% below the lower limit of normal, low MCV, and normal ferritin. TT is one of the most commonly screened conditions in the world, but existing diagnostic methods are either very expensive or have unacceptably low diagnostic accuracy, with false positive rates of up to 30% (19-20). The model and methods described herein provide a new and possibly more accurate way to distinguish between IDA and TT and possibly other causes of anemia FIG. 2 shows that $D_h$ differentiates IDA and TT, the two most common causes of microcytic anemia. An exemplary threshold value for $D_h$ of 0.0045 was established by analyzing 10 training samples. 50 independent patient samples were then analyzed where diagnosis of either mild IDA or TT could be confidently established, and $D_h$ was calculated. FIG. 4 shows that this $D_h$ threshold had a diagnostic accuracy of 98%, correctly identifying 22/22 cases of IDA and 27/28 cases of TT, and outperforming other published approaches by between 6 and 41% (20). See Example 4, "Differential Diagnosis of Microcytic Anemia."

Thus, the methods described herein can include making a differential diagnosis between iron deficiency anemia (IDA) and thalassemia trait (TT) and possibly other causes of anemia in a subject who has microcytic anemia by a method that includes determining a value for the magnitude of fluctuation from the mean hemoglobin content ($D_h$) in a sample from the subject, and comparing $D_h$ to a reference value. The presence of a $D_h$ that is above the reference value indicates that the subject has IDA, and the presence of a $D_h$ that is below the reference value indicates that the subject has TT.

Optimizing Erythropoiesis Stimulating Agent (e.g., Erythropoietin (EPO)) and/or Iron Supplementation Therapy The methods described herein can also be used to optimize EPO or iron supplementation therapy. For example, the methods could include determining the normalized critical volume, $v_c$, in a sample from a subject undergoing EPO treatment.

In some embodiments, the dose of EPO or iron supplementation is adjusted to maintain the $v_c$ or $D_h$ at a desired level, e.g., a level above or below a threshold level, or a level within a desired range. For example, as noted herein $v_c$ in normal healthy individuals is about 80% of the population mean volume, $\bar{v}$, or about 72 fL for a typical MCV of 90 fL. Thus, in some embodiments, the methods include adjusting the dose of EPO or iron supplementation to maintain a $v_c$ of greater than 70% of $\bar{v}$ in the subject; $v_c$ of greater than 75% of $\bar{v}$ in the subject; a $v_c$ between 75-85% of $\bar{v}$ in the subject. In some embodiments, the methods include adjusting the treatment to maintain a $v_c$ greater than 70%; or a $v_c$ between 70-75%. In some embodiments, $v_c$ or $D_h$ is monitored over time, and the dose of EPO or iron supplementation administered to the subject is adjusted to keep $v_c$ or $D_h$ above or below a selected threshold, or within a given range.

Identifying Subjects with an Elevated Risk of GI Disorder

IDA or otherwise unexplained anemia is often the initial presentation in serious conditions including gastrointestinal disorders such as colon cancer (16) and childhood malnutrition (17). Other GI disorders associated with IDA include colorectal (e.g., colon) cancer; gastrointestinal tract ulcers (gastric, peptic, cecal); diverticulitis; ischemic bowel; gastric cancer; gastritis; esophagitis; GI polyps; inflammatory bowel disease (Crohn's Disease, ulcerative colitis); and Celiac disease. Earlier detection or prediction of anemia via this method would enable a faster response to such conditions. Thus, the methods herein can be used for screening or for recommendation additional screening, e.g., for a GI disorder (e.g., using a colonoscopy) or for nutritional evaluation. Appropriate patient work-up could then be initiated sooner, e.g., performing colonoscopy, or appropriate treatment could then be initiated sooner, e.g., prescribing iron supplementation.

Detecting Blood Doping

An athlete's performance, particularly in aerobic sports, can be influenced by the number of RBCs present; the more RBCs, the greater the capacity for transport and delivery of oxygen from lungs to working muscles. An acute and temporary increase in red blood cells can be obtained by means of blood transfusions, referred to as blood doping, or the use of erythropoietic stimulant agents such as erythropoietin, analogs and mimetics. Blood doping can be notoriously difficult to detect. See, e.g., Jelkmann and Lundby, Blood. 2011 Sep. 1; 118(9):2395-404; Segura et al., "Current strategic approaches for the detection of blood doping practices," Forensic Sci Int. 2011 Aug. 31. [Epub ahead of print]. The present methods can be used to detect the presence of an abnormal distribution of RBC volume and HGB content, which would indicate the likely use of blood doping or erythropoietic stimulant agents. For example, in some embodiments, the values for one or both of the magnitude of fluctuation from the mean hemoglobin content ($D_h$) and the magnitude of fluctuation from the mean cell volume ($D_v$) are determined in a sample from a subject suspected of blood doping or using erythropoietic stimulant agents, and the presence of $D_h$ and/or $D_v$ above a reference value indicates the presence or use of blood doping or using erythropoietic stimulant agents.

Samples, Systems, Software, and Assay Methods

The methods described herein are practiced using peripheral blood samples obtained using known collection methodology that preserves RBCs intact (e.g., a blood draw with an appropriate amount of vacuum (draw) and a needle large enough to allow the RBCs to be collected without substantial hemolysis, e.g., a needle of at least 25 g or larger). The measurements are preferably made within 24, 12, or 6 hours of collection. Reticulocyte and CBC measurements can be made using any methods or devices known in the art that can measure both RBC volume (e.g., using low angle (2°-3°) scatter detection) and hemoglobin mass or concentration (e.g., using high angle (5°-15°) scatter detection). Exemplary methods are described in US20110178716, US20110164803, US 20110149061, 20110077871, 20110070606, and 20110070210.

In some embodiments, the measurements are made using a hemanalyzer, e.g., a manual, semi-automated, or automated hematology analyzer, examples of which are known on the art and described in, e.g., U.S. Pat. Nos. 5,017,497, 5,266,269, 5,378,633, 5,631,165, 5,812,419, 6,228,652, 6,524,858, 6,320,656, 7,324,194, and 7,981,681, as well as published U.S. Patent Applications US20080153170, US20080158561, US20080268494, US20110178716, 20110077871, and 20110070606, the disclosures of which are incorporated herein by reference in their entirety. Hemanalyzers useful in the present methods can use any detection method known in the art, e.g., flow cytometry or optical or image-based analysis or impedance based. Hemanalyzers useful in the present methods will typically be those that are capable of measuring all the parameters of the CBC. Specifically, the analyzers should be able to determine at least the red blood cell (RBC) cell volume (CV), and either the cell hemoglobin concentration (CHC) or cell hemoglobin mass (CH).

A number of models of hematology analyzers are commercially available, e.g., from Abbott Laboratories (Abbott Park, Ill., United States) (e.g., the Cell-Dyn Sapphire); and Siemens (Deerfield, Ill., United States) (e.g., the Advia 120 or 2120 automated hemanalyzer). Other manufacturers include Beckman Coulter, Inc. (Fullerton, Calif., United States); TOA Medical Electronics Co., (Kobe, Japan); Constitution Medical (Boston, Mass.); and HORIBA ABX Inc (Irvine, Calif., United States).

The present invention also provides hematology analyzer systems comprising a detection module for measuring a clinical sample; and a computing device that is in communication with the detection module and comprises programming for determining, based on the output of the detection module, one or more of: (i) a population mean corpuscular hemoglobin concentration (MCHC) and the fraction of red blood cells in the sample whose transformed volume and hemoglobin content fall below a threshold percentage of the average of all transformed volume and hemoglobin contents, to determine a sample fraction; (ii) a magnitude of variation among cells in the population in the rate of hemoglobin content reduction ($D_h$); (iii) a magnitude of variation among cells in the population in the rate of cell volume reduction ($D_v$); and/or (iv) a normalized critical volume ($v_c$) or other clearance threshold. In some embodiments, the computing device is a separate computer, using inputs from the hemanalyzer. In some embodiments, the computing device is integrated into, or part of, a hemanalyzer device.

In general, the detection module comprises an analysis chamber configured to hold a sample comprising red blood cells, e.g. whole blood, for analysis. In some embodiments, the detection module comprises a flow cytometer configured to analyze the sample. In some embodiments, the detection module comprises an optical or image analyzer configured to analyze the sample.

Also provided herein is computer-readable medium comprising programming to calculate one or more of: (i) a population mean corpuscular hemoglobin concentration (MCHC) and the fraction of red blood cells in the sample whose transformed volume and hemoglobin content fall below a threshold percentage of the average of all transformed volume and hemoglobin contents, to determine a sample fraction; (ii) a magnitude of variation among cells in the population in the rate of hemoglobin content reduction ($D_h$); (iii) a magnitude of variation among cells in the population in the rate of cell volume reduction ($D_v$); and/or (iv) a normalized critical volume ($v_c$) or other clearance threshold.

In some embodiments, data from a hematology analyzer is received (e.g., red blood cell (RBC) cell volume (CV), mean cell volume (MCV), cell hemoglobin concentration (CHC) or cell hemoglobin content (CH), mean cell hemoglobin concentration (MCHC), and the mean cell hemoglobin content (MCH), as well as their population statistics), by a computing device that then executes programming containing an algorithm as described herein for the calculation of one or more of (i) a population mean corpuscular hemoglobin concentration (MCHC) and the fraction of red blood cells in the sample whose transformed volume and hemoglobin content fall below a threshold percentage of the average of all transformed volume and hemoglobin contents, to determine a sample fraction; (ii) a magnitude of variation among cells in the population in the rate of hemoglobin content reduction ($D_h$); (iii) a magnitude of variation among cells in the population in the rate of cell volume reduction ($D_v$); and/or (iv) a normalized critical volume ($v_c$) or other clearance threshold.

In some embodiments, the computing device is a separate computer, using inputs from the hemanalyzer. In some embodiments, the computing device is integrated into, or part of, a hemanalyzer device.

The programming can be provided in a physical storage or transmission medium. A computing device (e.g., a separate device or an information processing module that is part of a hemanalyzer system) receiving the instructions can then execute the algorithm and/or process data obtained from the subject method. Examples of storage media that are computer-readable include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information can be "stored" on computer readable medium, where "storing" means recording information such that it is accessible and retrievable at a later date by a computer on a local or remote network. In some embodiments, the methods described herein are automatically executed each time a sample is run.

Figure 14:
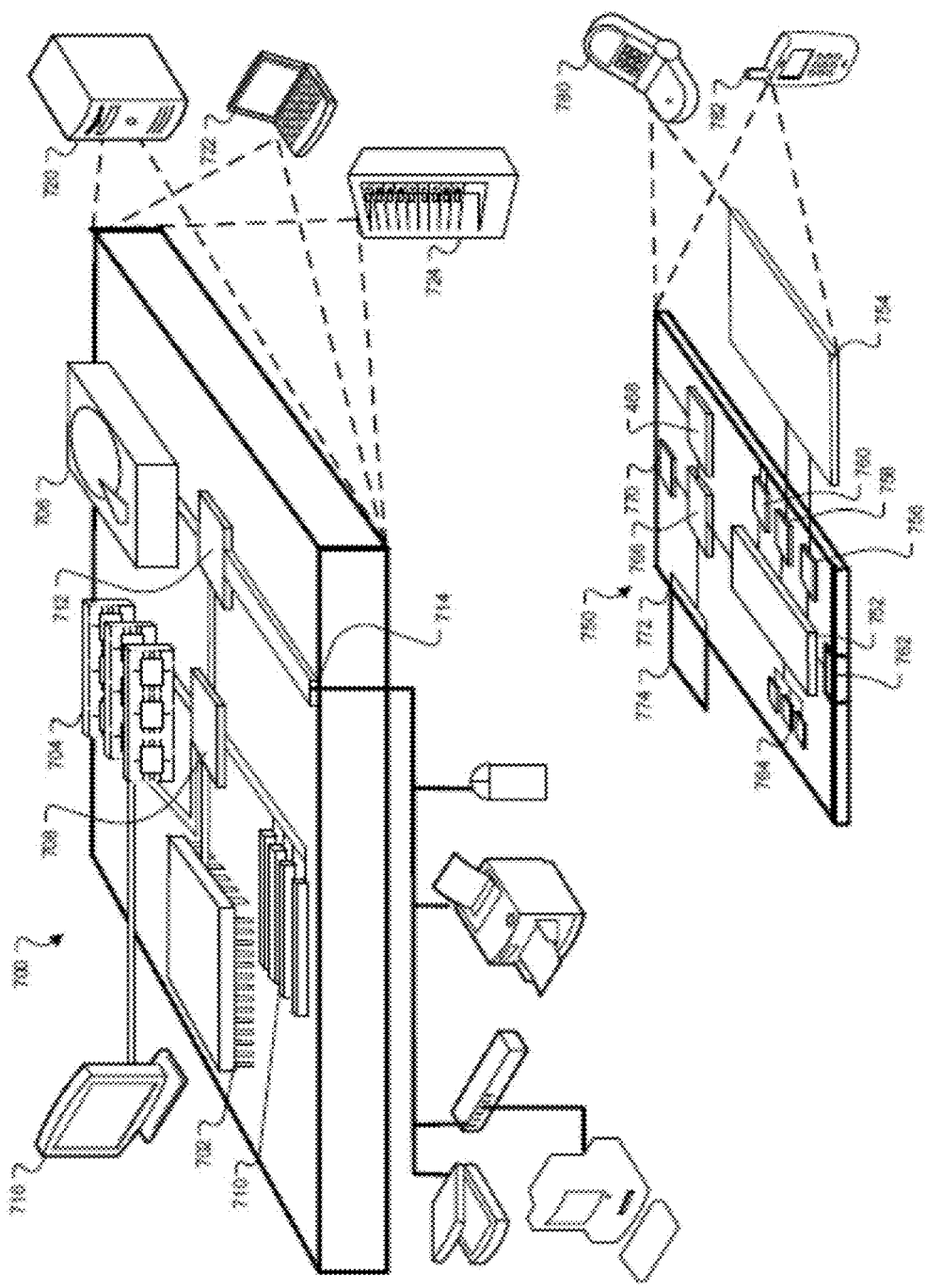
FIG. 14 is a block diagram illustrating an exemplary computing device for use in the present invention.

FIG. 14 shows an example of computer device 700 and mobile computer device 750, which can be used with the techniques described here. Computing device 700 is intended to represent various forms of digital computers, including, e.g., laptops, desktops, workstations, personal digital assistants, servers, blade servers, mainframes, and other appropriate computers. Computing device 750 is intended to represent various forms of mobile devices, including, e.g., personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 700 is intended to represent various forms of digital computers, including, e.g., laptops, desktops, workstations, personal digital assistants, servers, blade servers, mainframes, and other appropriate computers, including computers that are incorporated into hemanalyzer systems or devices. Computing device 750 is intended to represent various forms of mobile devices, including, e.g., personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 700 includes processor 702, memory 704, storage device 706, high-speed user interface 708 connecting to memory 704 and high-speed expansion ports 710, and low speed user interface 712 connecting to low speed bus 714 and storage device 706. Each of components 702, 704, 706, 708, 710, and 712, are interconnected using various busses, and can be mounted on a common motherboard or in other manners as appropriate. Processor 702 can process instructions for execution within computing device 700, including instructions stored in memory 704 or on storage device 706 to display graphical information for a GUI on an external input/output device, including, e.g., display 716 coupled to high speed user interface 708. In other implementations, multiple processors and/or multiple buses can be used, as appropriate, along with multiple memories and types of memory. Also, multiple computing devices 700 can be connected, with each device providing portions of the necessary operations (e.g., as a server bank, a group of blade servers, or a multi-processor system).

Memory 704 stores information within computing device 700. In one implementation, memory 704 is a volatile memory unit or units. In another implementation, memory 704 is a non-volatile memory unit or units. Memory 704 also can be another form of computer-readable medium, including, e.g., a magnetic or optical disk.

Storage device 706 is capable of providing mass storage for computing device 700. In one implementation, storage device 706 can be or contain a computer-readable medium, including, e.g., a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product also can contain instructions that, when executed, perform one or more methods, including, e.g., those described above. The information carrier is a computer- or machine-readable medium, including, e.g., memory 704, storage device 706, memory on processor 702, and the like.

High-speed controller 708 manages bandwidth-intensive operations for computing device 700, while low speed controller 712 manages lower bandwidth-intensive operations. Such allocation of functions is an example only. In one implementation, high-speed controller 708 is coupled to memory 704, display 716 (e.g., through a graphics processor or accelerator), and to high-speed expansion ports 710, which can accept various expansion cards (not shown). In the implementation, low-speed controller 712 is coupled to storage device 706 and low-speed expansion port 714. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router, e.g., through a network adapter.

Computing device 700 can be implemented in a number of different forms, as shown in the figure. For example, it can be implemented as standard server 720, or multiple times in a group of such servers. It also can be implemented as part of rack server system 724. In addition or as an alternative, it can be implemented in a personal computer including, e.g., laptop computer 722. In some examples, components from computing device 700 can be combined with other components in a mobile device (not shown), including, e.g., device 750. Each of such devices can contain one or more of computing device 700, 750, and an entire system can be made up of multiple computing devices 700, 750 communicating with each other.

Computing device 750 includes processor 752, memory 764, an input/output device including, e.g., display 754, communication user interface 766, and transceiver 768, among other components. Device 750 also can be provided with a storage device, including, e.g., a microdrive or other device, to provide additional storage. Each of components 750, 752, 764, 754, 766, and 768, are interconnected using various buses, and several of the components can be mounted on a common motherboard or in other manners as appropriate.

Processor 752 can execute instructions within computing device 750, including instructions stored in memory 764. The processor can be implemented as a chipset of chips that include separate and multiple analog and digital processors. The processor can provide, for example, for coordination of the other components of device 750, including, e.g., control of user interfaces, applications run by device 750, and wireless communication by device 750.

Processor 752 can communicate with a user through control user interface 758 and display user interface 756 coupled to display 754. Display 754 can be, for example, a TFT LCD (Thin-Film-Transistor Liquid Crystal Display) or an OLED (Organic Light Emitting Diode) display, or other appropriate display technology. Display user interface 756 can comprise appropriate circuitry for driving display 754 to present graphical and other information to a user. Control user interface 758 can receive commands from a user and convert them for submission to processor 752. In addition, external user interface 762 can communicate with processor 742, so as to enable near area communication of device 750 with other devices. External user interface 762 can provide, for example, for wired communication in some implementations, or for wireless communication in other implementations, and multiple user interfaces also can be used.

Memory 764 stores information within computing device 750. Memory 764 can be implemented as one or more of a computer-readable medium or media, a volatile memory unit or units, or a non-volatile memory unit or units. Expansion memory 774 also can be provided and connected to device 750 through expansion user interface 772, which can include, for example, a SIMM (Single In Line Memory Module) card user interface. Such expansion memory 774 can provide extra storage space for device 750, or also can store applications or other information for device 750. Specifically, expansion memory 774 can include instructions to carry out or supplement the processes described above, and can include secure information also. Thus, for example, expansion memory 774 can be provide as a security module for device 750, and can be programmed with instructions that permit secure use of device 750. In addition, secure applications can be provided through the SIMM cards, along with additional information, including, e.g., placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, including, e.g., those described above. The information carrier is a computer- or machine-readable medium, including, e.g., memory 764, expansion memory 774, and/or memory on processor 752, that can be received, for example, over transceiver 768 or external user interface 762.

Device 750 can communicate wirelessly through communication user interface 766, which can include digital signal processing circuitry where necessary. Communication user interface 766 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 768. In addition, short-range communication can occur, including, e.g., using a Bluetooth®, WiFi, or other such transceiver (not shown). In addition, GPS (Global Positioning System) receiver module 770 can provide additional navigation- and location-related wireless data to device 750, which can be used as appropriate by applications running on device 750.

Device 750 also can communicate audibly using audio codec 760, which can receive spoken information from a user and convert it to usable digital information. Audio codec 760 can likewise generate audible sound for a user, including, e.g., through a speaker, e.g., in a handset of device 750. Such sound can include sound from voice telephone calls, can include recorded sound (e.g., voice messages, music files, and the like) and also can include sound generated by applications operating on device 750.

Computing device 750 can be implemented in a number of different forms, as shown in the figure. For example, it can be implemented as cellular telephone 780. It also can be implemented as part of smartphone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or a combination of such back end, middleware, or front end components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

EXAMPLES

The invention is further described in the following examples, which do not limit the scope of the invention described in the claims.

Example 1. Model Development

Figure 1B:
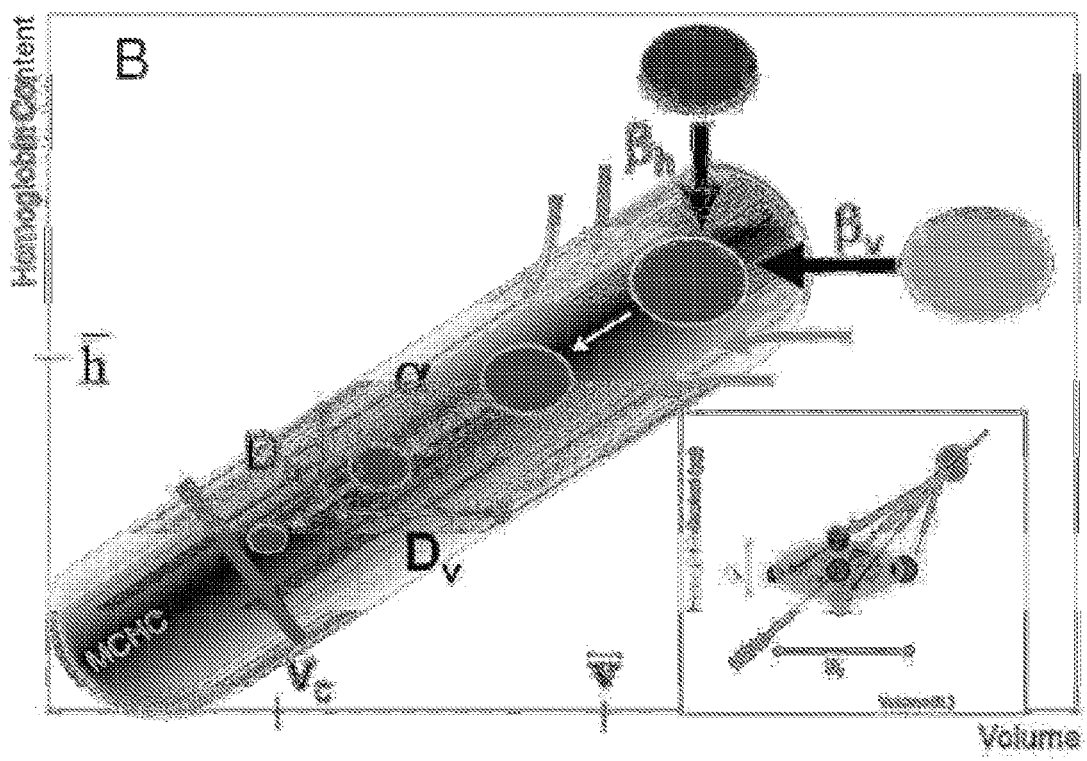

The volume and hemoglobin regulation of an individual RBC in vivo during the course of its lifetime is extremely complex and difficult to understand. Understanding the average behavior of a large population of RBCs may be more tractable. To gain insight into this population-level behavior, a model of RBC maturation and clearance was developed that describes the dynamics of an RBC population. The model decomposes the volume (v) and hemoglobin (h) dynamics of an average RBC over time (t) into deterministic reductions (f) and random fluctuations (ξ) whose specific functional form can vary, with one example shown in Equation 1, where v and h are scaled by their population means ($\bar{v}$, $\bar{h}$), and t is scaled by the average cell age ($\bar{\tau}$). Based on data from prior reports (3-5, 7), two parameters were introduced into the deterministic component: a fast change (β) whose effect dominates until the RBC is close to the MCHC line, and a slow change (α). The random fluctuation can be modeled as a Gaussian or similarly distributed random variable with mean zero and variance given by a diffusion tensor 2D, as shown in FIG. 1B and Equation 1.

$$\begin{bmatrix} \dfrac{dv}{dt} \\ \dfrac{dh}{dt} \end{bmatrix} = f + \zeta \quad (1)$$

$$f = \begin{cases} \alpha \cdot e^{\beta_v(v-h)} \\ \alpha \cdot e^{\beta_h(h-v)} \end{cases}$$

$$\zeta = \begin{cases} N(0, 2D_v) \\ N(0, 2D_h) \end{cases}$$

As with inverse problems in general and human pathophysiology in particular (9), this problem is ill-posed in the sense that different functional forms of f will reproduce the in vivo dynamics. The precise functional form of f is not essential. The behavior of this model relied on the qualitative combination of fast and slow deterministic dynamics and random fluctuations. Table 1A-B shows different types of functional forms that could be used in the model.

Table 1A Functional Forms for f

| | f |
|---|---|
| A | $f_v = -\alpha \cdot e^{\beta_v(v-h)}$<br>$f_h = -\alpha \cdot e^{\beta_h(h-v)}$ |
| B | $f_v = -\alpha \cdot \max\{\beta_v(v-h), 1\}$<br>$f_h = -\alpha \cdot \max\{(\beta_h(h-v), 1\}$ |
| C | $f_v = -\alpha \cdot v \cdot \max\{\beta_v(v-h), 1\}$<br>$f_h = -\alpha \cdot h \cdot \max\{\beta_h(h-v), 1\}$ |
| D | $f_v = -\alpha \cdot v \cdot e^{\beta_v(v-h)}$<br>$f_h = -\alpha \cdot h \cdot e^{\beta_h(h-v)}$ |
| E | $f_v = -\alpha - \max\{\beta_v(v-h), 0\}$<br>$f_h = -\alpha - \max\{\beta_h(v-h), 0\}$ |
| D | $f_v = -\alpha_v \cdot v \cdot e^{\beta_v(v-h)}$<br>$f_h = -\alpha_h \cdot h \cdot e^{\beta_h(h-v)}$ |

Table 1B. Functional Forms for d

| | d |
|---|---|
| A | $d(v, h) = \dfrac{1}{1+e^\Delta}$ |
| B | $d(v, h) = \begin{cases} 1 & \Delta \le 0 \\ 0 & \Delta > 0 \end{cases}$ |
| C | $d(v, h; k) = \dfrac{1}{1+e^{k\Delta}}$ |

FIGS. 9A-C show velocity fields corresponding to forms A-C off, and FIGS. 10A-B show the clearance function (d) forms A and B. τ is the mean age of cells in the population. The definition of Δ is set forth below.

Figure 11:
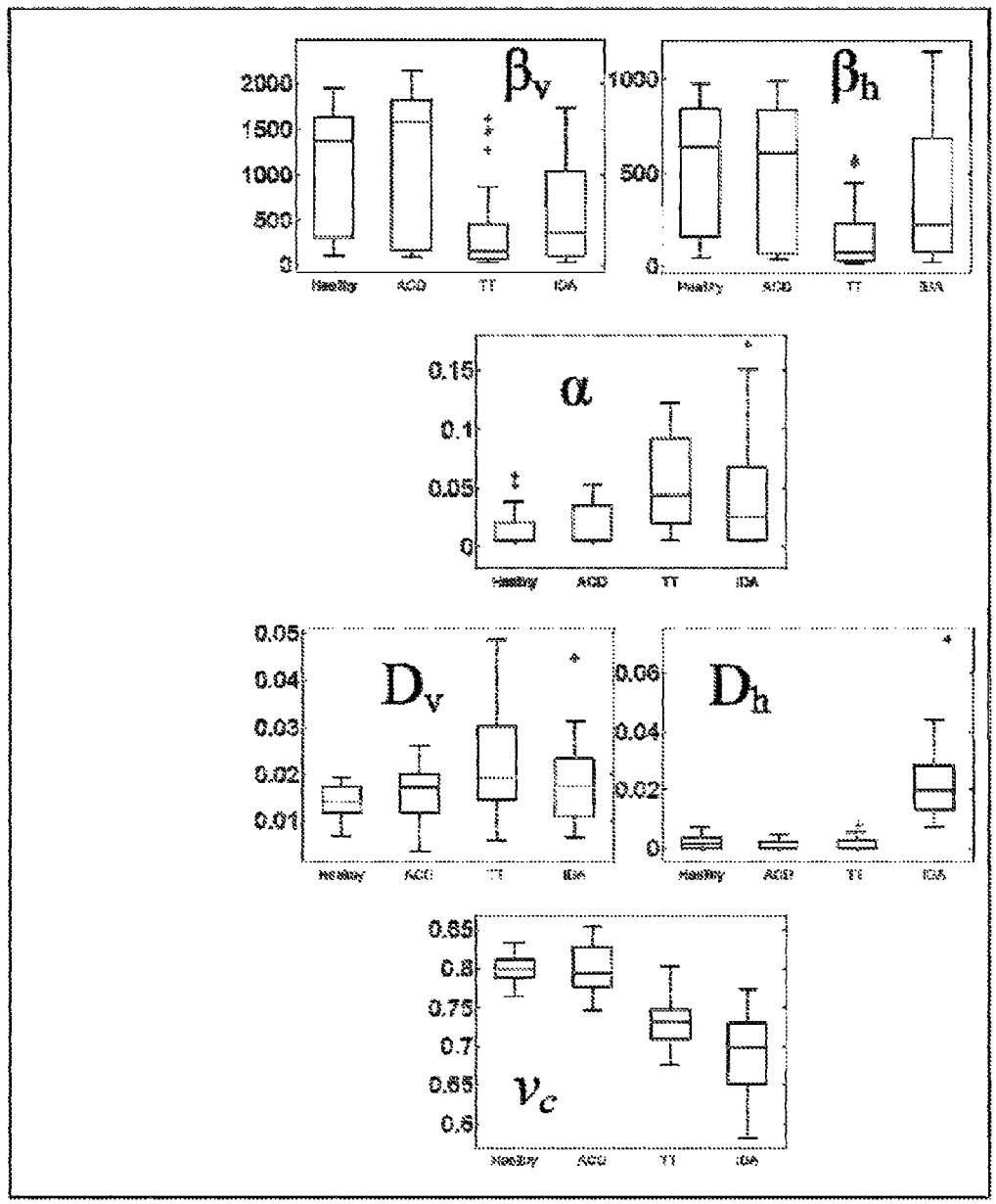
FIG. 11 is a set of six boxplots of model parameters based on functional form B from Table 1A-B for 20 healthy individuals and how they change for patients with three forms of mild anemia: 11 with anemia of chronic disease (ACD), 33 with thalassemia trait, and 27 with iron deficiency anemia. The upper and lower edges of each box are located at the 75th and 25th percentiles. The median is indicated by a horizontal line in the interior of the box. Vertical lines extend to data points that are within 1.5 times the interquartile distance from the box. More extreme data points are shown as plus (+) symbols. The fast dynamics are characterized by β, the slow by α, random fluctuations by D, and the clearance threshold by $v_c$.
Figure 12:
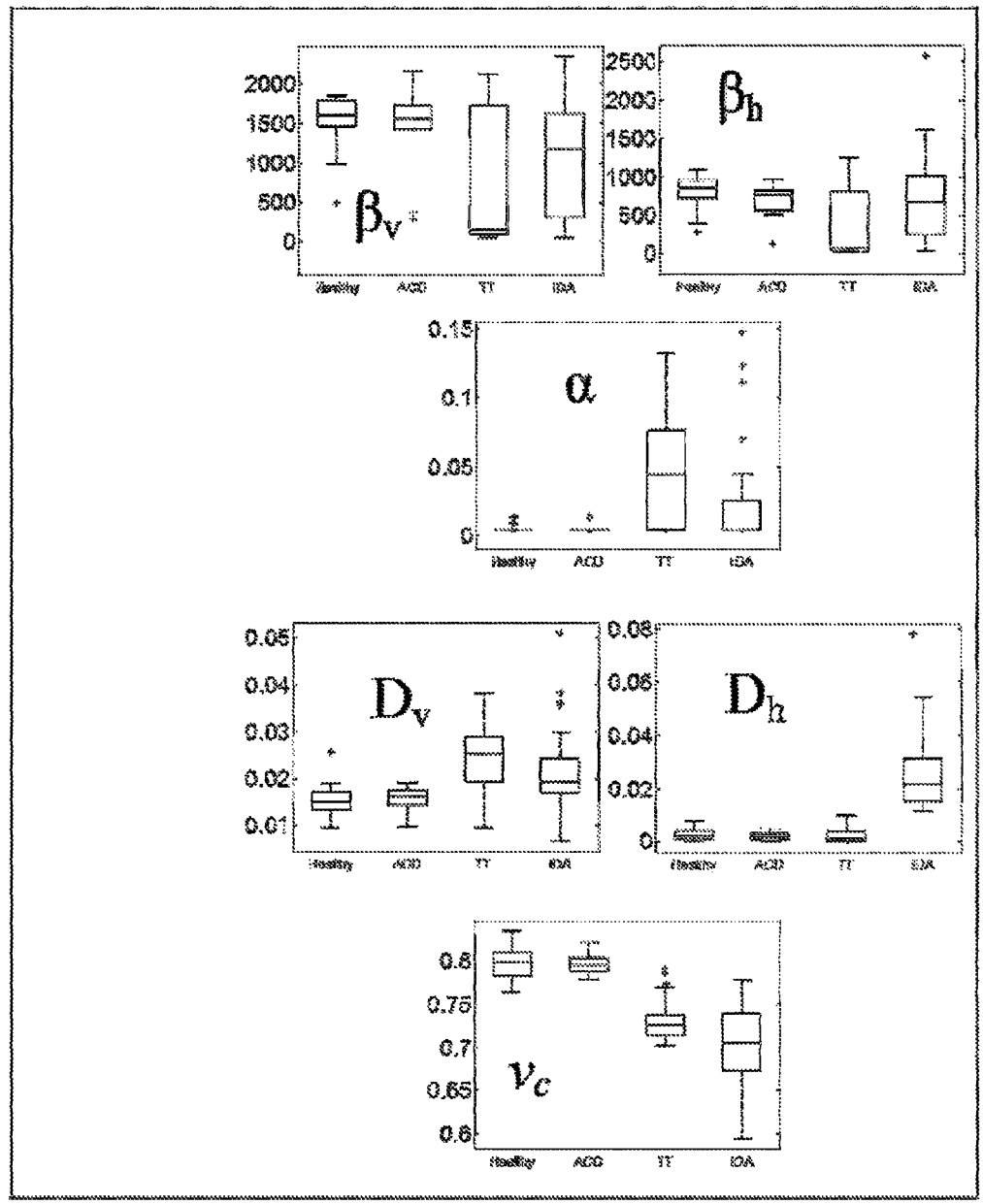
FIG. 12 is a set of six boxplots of model parameters based on functional form C from Table 2 for 20 healthy individuals and how they change for patients with three forms of mild anemia: 11 with anemia of chronic disease (ACD), 33 with thalassemia trait, and 27 with iron deficiency anemia. The upper and lower edges of each box are located at the 75th and 25th percentiles. The median is indicated by a horizontal line in the interior of the box. Vertical lines extend to data points that are within 1.5 times the interquartile distance from the box. More extreme data points are shown as plus (+) symbols. The fast dynamics are characterized by β, the slow by α, random fluctuations by D, and the clearance threshold by $v_c$.
Figure 13A:
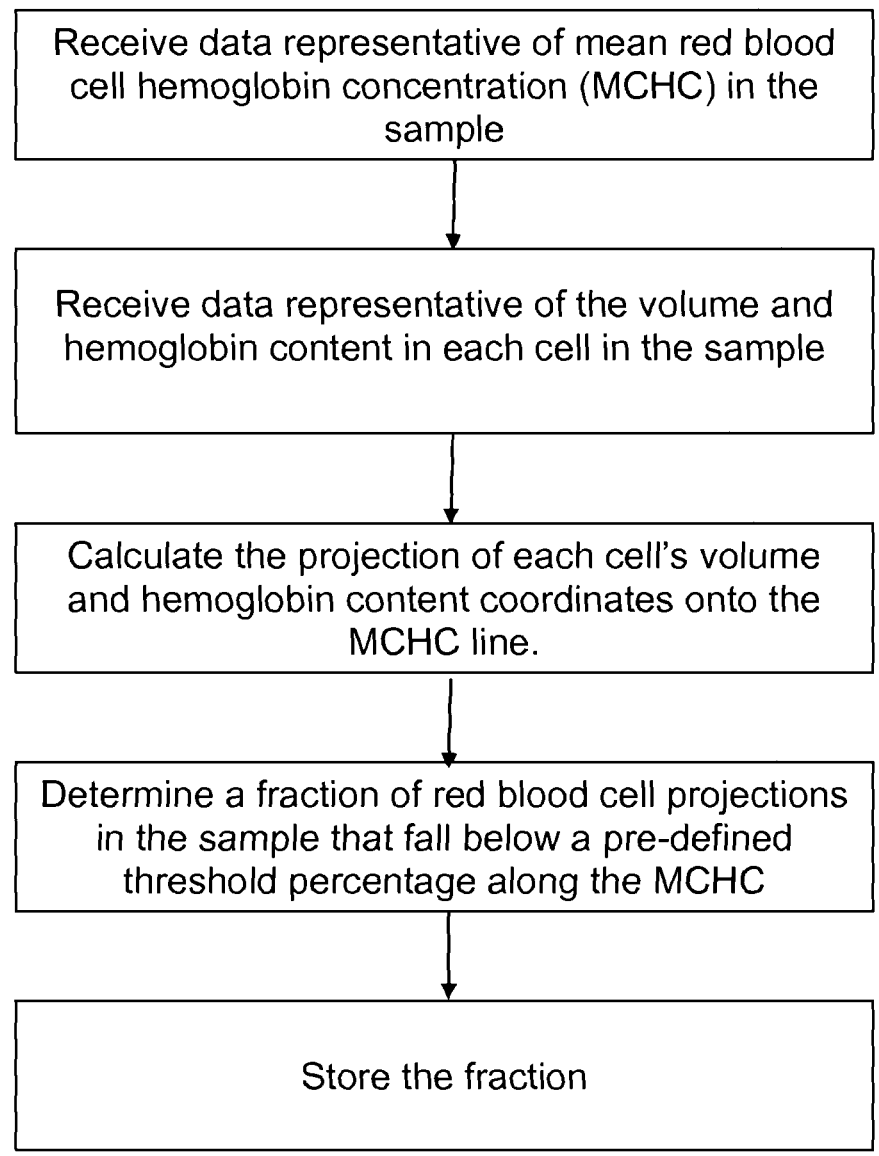
FIGS. 13A-B are block diagrams illustrating exemplary method steps for determining the fraction of cells in a sample whose volume and hemoglobin content, when projected on the MCHC line, falls below a threshold percentage of the mean projection location along this line according to some embodiments of the present invention.
Figure 13B:
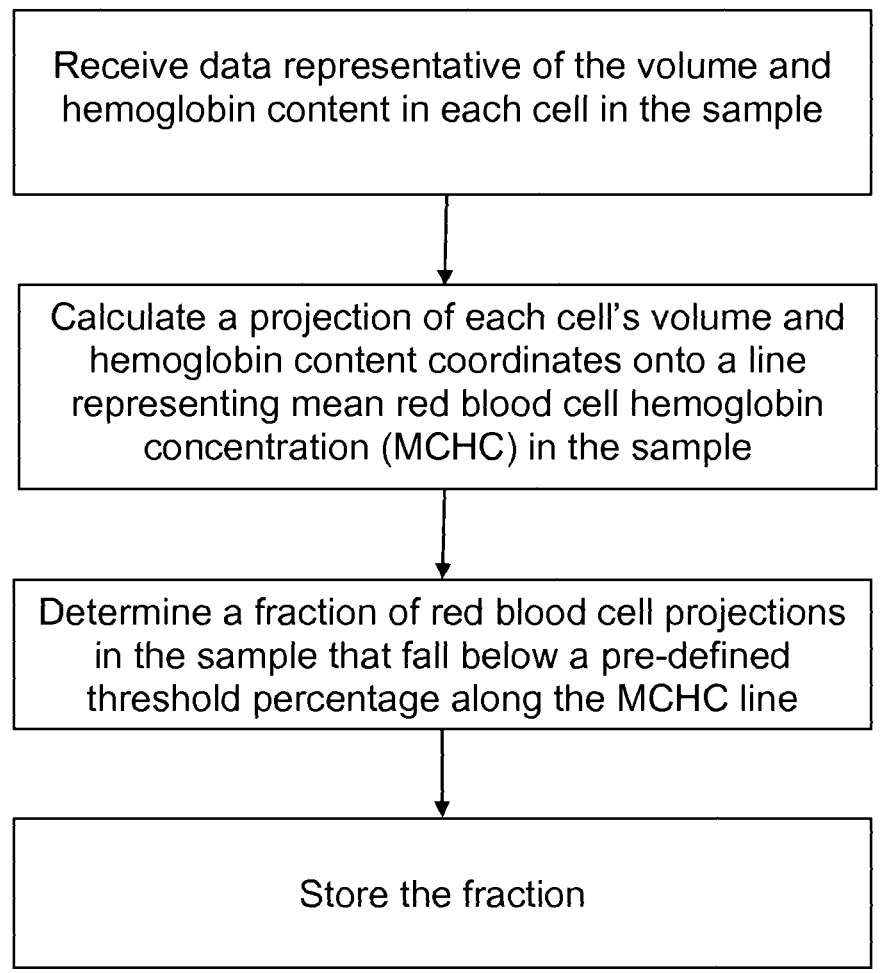

Parameters were estimated for different functional forms of the deterministic evolution (f) and clearance functions (d). The qualitative results are consistent for these different functional forms, suggesting that these results represent characteristics of in vivo pathophysiology and not overfitting of data. Details of the functional forms are shown in Table 1A-B, and the estimates for forms A-C are shown in boxplots in FIGS. 2, 11, and 12.

In the present model, the random fluctuation and deterministic dissipation or reduction of volume and hemoglobin content for a typical individual cell was described by a Langevin equation, commonly used to model Brownian motion in a potential (10). The dynamics of the entire circulating population of RBCs can then be described by a master equation for the time-dependent joint volume-hemoglobin probability distribution (P(v,h,t)) which can be approximated by a Fokker-Planck equation (10-11). Equation 2 describes the drift (f), diffusion (D), birth (b), and death (d) of probability density for this joint volume-hemoglobin distribution.

$$\frac{\partial P}{\partial t} = -\nabla \cdot (Pf) + \nabla \cdot (D \cdot \nabla P) + b(v, h, t) - d(v, h, t)P \quad (2)$$

$$D = \begin{bmatrix} D_v & 0 \\ 0 & D_h \end{bmatrix}$$

The birth and death processes account for the RBCs that are constantly added to and removed from the population. In states of health and mild illness, the total number of cells added equals the total number removed: $\iint d(v,h)P\, dv\, dh = \iint b(v,h)dv\, dh$. The precise trigger and mechanism for RBC removal are not fully understood (12), but empirical measurements such as those shown in FIG. 1A suggest that there is a threshold ($v_c$) along the MCHC line beyond which most RBCs have been cleared.

Based on observations of empirical RBC distributions, probability of RBC clearance was modeled as a function of the RBC volume and hemoglobin content. Each RBC's position in the volume-hemoglobin content plane was projected onto the MCHC line, and the probability of clearance (d) was defined variously, for instance as a sigmoid (FIG. 10A) or step (FIG. 10B) function of the distance from this projected point to a threshold, $v_c$, on this line. See FIGS. 1 and 5 and Table 1B. Equation 3 quantifies this relationship.

$$d(v, h) = \frac{1}{1 + e^\Delta} \quad (3)$$

or $$d(v, h) = \begin{cases} 1 & \Delta \le 0 \\ 0 & \Delta > 0 \end{cases}$$

$$\Delta(v, h) = 100 \cdot \frac{\cos(\theta)\sqrt{(v\bar{v})^2 + (h\bar{h})^2} - v_c\sqrt{\bar{h}^2 + \bar{v}^2}}{v_c\sqrt{\bar{h}^2 + \bar{v}^2}}$$

$$\theta = \tan^{-1}\left(\frac{\bar{h}}{\bar{v}}\right) - \tan^{-1}\left(\frac{h\bar{h}}{v\bar{v}}\right)$$

CBC measurements vary from person to person but do not change significantly for a healthy individual (13) indicating that these dynamic processes reach a steady state $$P_\infty \lim_{t \to \infty} P(v, h, t) \to P_\infty(v, h), \text{ i.e., } \frac{\partial P_\infty}{\partial t} = 0$$

in vivo, where

For a given set of parameters, Equation 2 could be solved numerically using a finite difference approximation for first order $$\left(J = \frac{\Delta_k[f \cdot P](v)}{k} + \frac{\Delta_k[f \cdot P](h)}{k}\right)$$

and second order $$\left(L = D_v \frac{\delta_k^2[P](v)}{k^2} + D_h \frac{\delta_k^2[P](h)}{k^2}\right)$$

spatial derivatives with boundary conditions of vanishing probability at volumes and hemoglobin contents outside the pathophysiological range and initial conditions equal to the empirically measured reticulocyte distribution. The volume-hemoglobin content plane was discretized with a constant mesh width and represented as a vector (P) of variables equal to the probability density in each mesh cell. Simulation results reported here were executed with a mesh width of 1.8 fL along the volume axis and 1.8 pg along the hemoglobin content axis. This mesh width was comparable to the analytic resolution of the empirical volume and hemoglobin content measurements. All results were confirmed using a smaller mesh width (1.2 fL and 1.2 pg). The convection contribution (f) was modeled numerically using an upwind finite difference approximation of the spatial derivative. The resulting linear system of ordinary differential equations was integrated using the MATLAB ode15s integrator and iterated until a steady state ($P_\infty$) was reached.

The steady state distribution for the numerical problem ($P_\infty$) was also determined analytically; the numerical approximations of the evolution (J+L) and clearance (d) terms are linear operators and the integral scaling the birth process is a constant equal to the reciprocal of twice the mean age $$\left(\frac{1}{2\bar{\tau}}\right).$$

The linear operators can be inverted, yielding a family of steady state distributions indexed by the mean cell age, as shown in equation 4.

$$\frac{dP_\infty}{dt} = 0 = -J \cdot P_\infty + L \cdot P_\infty + d \cdot P_\infty + P_0 \int_h \int_v d(v, h) = \quad (4)$$

$$(-J + L + d) \cdot P_\infty + P_0 \frac{1}{2\bar{\tau}} \Rightarrow P_\infty = -(-J + L + d)^{-1} P_0 \frac{1}{2\bar{\tau}}$$

There were negligible differences between the steady state distributions obtained by the analytic and finite difference approaches.

With appropriate choice of parameters ($\alpha$, $\beta$, D, and $v_c$), the model described herein faithfully reproduces the observed distribution of RBC populations in healthy individuals.

Example 2. Validation

To test whether the model can distinguish the dynamics of RBC populations in healthy individuals from those for anemic individuals, CBC and reticulocyte measurements were obtained for individuals with three common forms of anemia with different underlying etiologies: anemia of chronic disease (ACD), an inflammatory condition; thalassemia trait (TT), a genetic disorder; and iron deficiency anemia (IDA), a nutritional condition (14). Mild cases of each anemia where RBC population characteristics appeared stable and a quasi-steady state assumption was reasonable were selected, as were several apparently healthy controls.

Blood samples and CBC results were obtained from the clinical laboratory of a tertiary care adult hospital under a research protocol approved by the Partners Healthcare Institutional Review Board. Reticulocyte and CBC measurements were made within 6 hours of collection (21) on a Siemens Advia 2120 automated hemanalyzer.

IDA was defined as mild reduction in hematocrit to no more than 20% below the lower limit of normal, low MCV, low ferritin, and historical evidence of normal MCV with normal hematocrit. Patients with acute illness, acute bleeding, transfusion in the prior 6 months, concurrent hospitalization, chronic inflammatory illness, or hemoglobinopathy were excluded.

TT was defined as either a high hemoglobin A2 fraction, or heterozygosity for the presence of an alpha globin gene mutation, as well as a reduction in hematocrit to no more than 20% below the lower limit of normal, low MCV, and normal ferritin. Patients with acute illness, acute bleeding, transfusion in the prior 6 months, concurrent hospitalization, chronic inflammatory illness, or additional hemoglobinopathy were excluded.

ACD was defined as a reduction in hematocrit to no more than 20% below the lower limit of normal, normal or high ferritin, and a low or normal total iron binding capacity. Patients with acute illness, acute bleeding, transfusion in the prior 6 months, concurrent hospitalization, or hemoglobinopathy were excluded.

For each patient sample, an optimal parameter set ($\alpha$, $\beta$, D, and $v_c$) was identified that reproduced the steady state observed for that patient. A least-squares fit between the simulated steady state distribution and the measured CBC distribution was used to identify the best fit. Where repeat tests were available for the same individual, it was found that any variation in fitted parameters was explained by analytic variation in the CBC measurement.

Optimal neighborhoods in parameter space were identified for each patient using gradient and non-gradient optimization methods. A patient's empirically measured reticulocyte distribution and an initial randomly chosen parameter set were used as a starting point. The resulting steady state RBC distribution was calculated using equation 4. This calculated distribution ($P_\infty$) was then compared with the empirical distribution ($P_{CBC}$). The quality of the parameter estimates was quantified by computing an objective function equal to the sum of the normalized squared residuals for the discretized distributions, as shown in equation 5, where i and j represent indices of cells in the discretized volume-hemoglobin plane.

$$C(P_{CBC}^{i,j}, P_\infty^{i,j}) = \sum_{i,j} \frac{(P_{CBC}^{i,j} - P_\infty^{i,j})^2}{P_{CBC}^{i,j}} \quad (5)$$

Figure 6A:
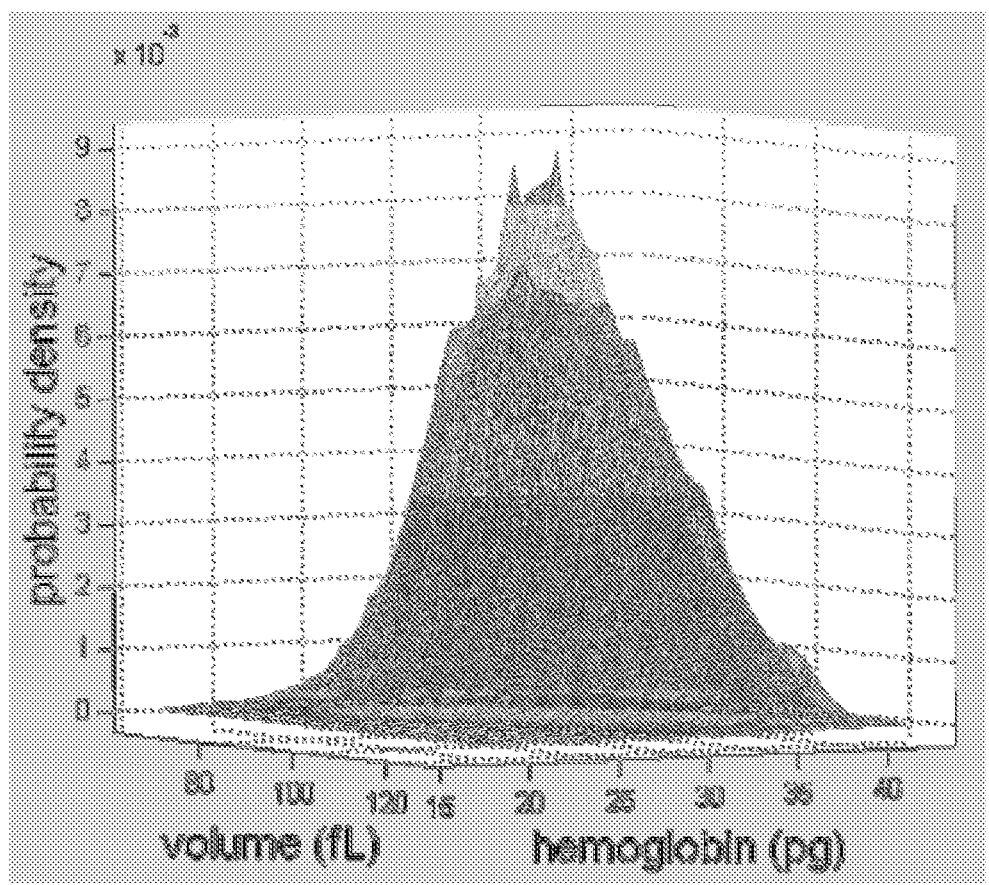
FIGS. 6A-B are 3D graphs showing a comparison of fitted (dark gray) and empirical (light gray) steady state joint volume-hemoglobin content probability distributions for a healthy individual.
Figure 6B:
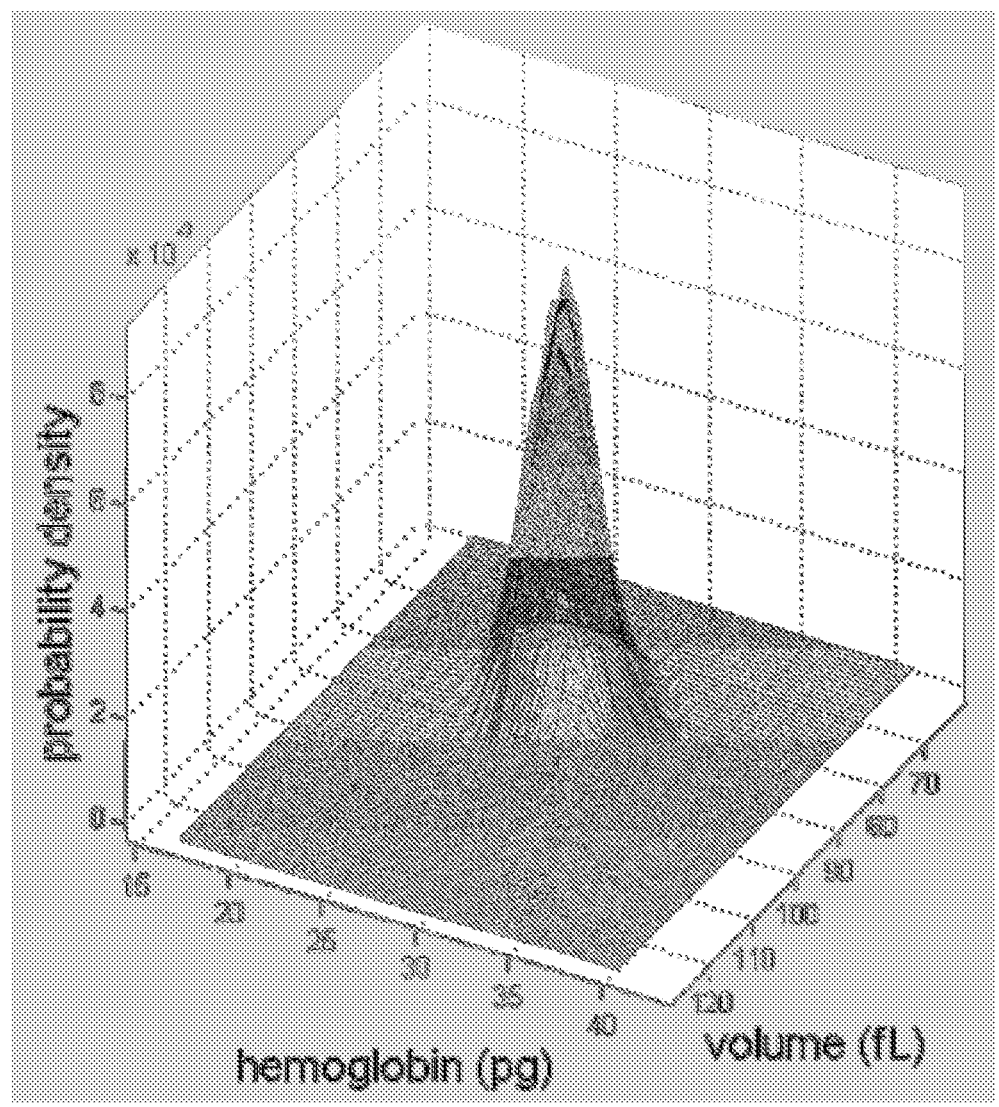

In general, the objective function provides a measure of an extent of dissimilarity (or similarity) between the two distributions. The parameter values can be adjusted based on whether a value of the objective function satisfies a threshold condition. For example, the parameter values can be adjusted until the value of the objective function is above or below a threshold. If the objective function represents a measure of dissimilarity (e.g. mean squared difference, sum of absolute differences etc.), the objective function is sought to be reduced by adjusting the parameters. Alternatively, if the objective function represents a measure of similarity (e.g. correlation coefficient, mutual information etc.) the objective function is sought to be increased by adjusting the parameters. In this example, new parameter values were then chosen to reduce this objective function. Gradient-based (lsqnonlin function) and non-gradient-based (fminsearch and patternsearch functions) optimization algorithms in MATLAB were used to search for optimal parameters. All parameters were constrained to be non-negative and defined a uniform initial parameter space to exclude mean cell ages greater than 1000 or less than 5 days. Initial parameters were then picked from this space using latin hyper-square sampling. One optimization constraint was imposed, limiting $\alpha$ to be small enough that the mean cell age would be greater than 5 days and large enough that the mean cell age would less than 1000 days. FIG. 6 shows that the model provides a faithful reproduction of $P_{CBC}$ for this healthy patient by comparing the simulated and measured steady state probability distributions. When projected along the MCHC line, the empirical distribution for this patient had slightly higher density near the mode and slightly lower in the regions to either side of the mode.

Figure 7:
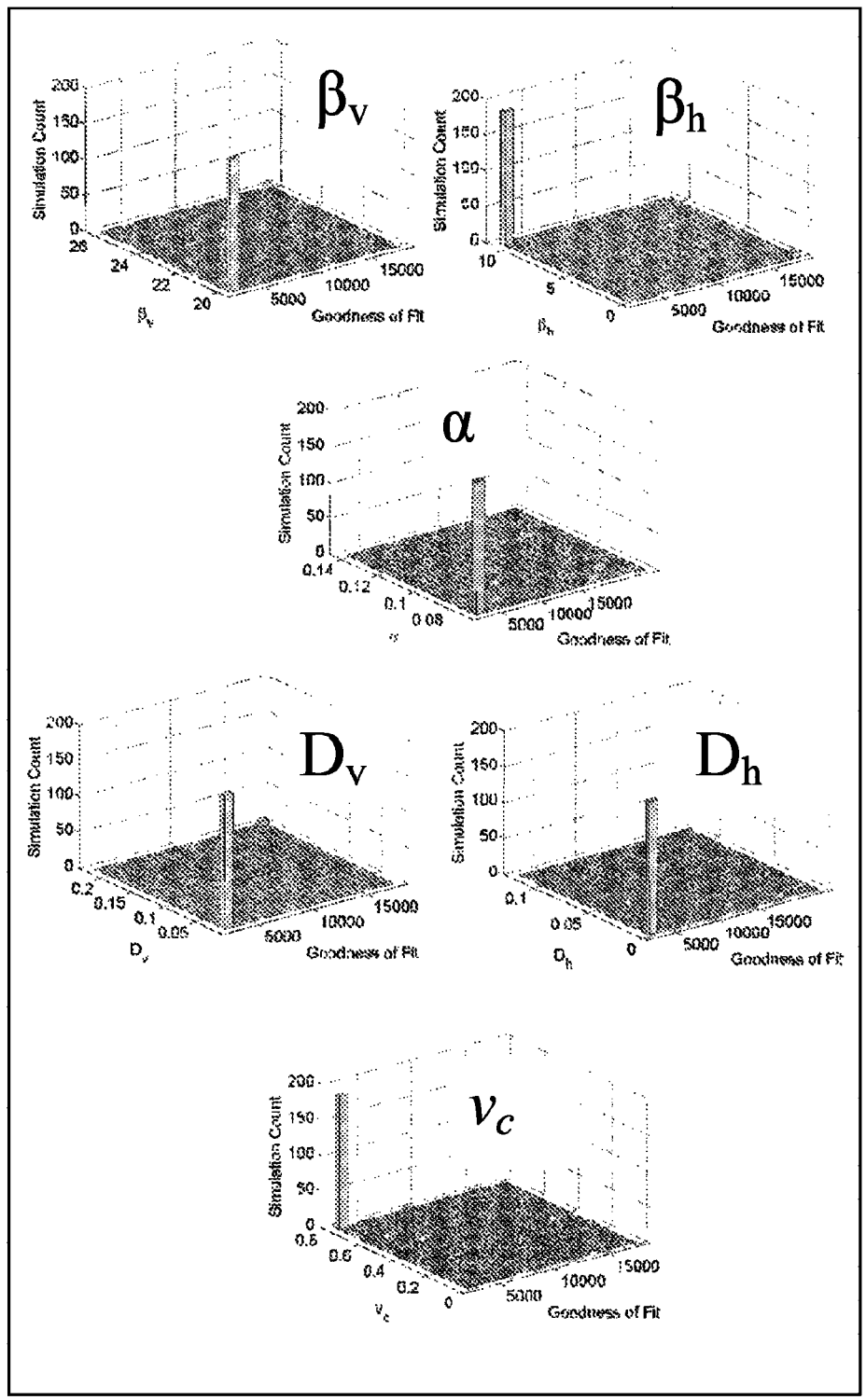
FIG. 7 is a set of six histograms of optimized parameter values from more than 200 separate simulations and the goodness of fit as determined by a sum of squared residuals objective function. Smaller values of the objective function signify a better fit.

FIG. 7 shows the smallest local minima for parameters obtained from more than 200 optimizations for a single patient. Some results had local minima above the range of the axes. The best fits among all simulations form a small neighborhood of values for all parameters, demonstrating that the parameter estimation process reached a well-defined optimal neighborhood for this patient's blood sample.

Fitted parameters for healthy and anemic individuals are shown in FIG. 2 and median fitted parameters are listed in Table 2.

TABLE 2

Median Values of Non-dimensional and Dimensional Fitted Parameters (where appropriate).

|  | Normal | ACD | TT | IDA |
|---|---|---|---|---|
| $\beta_v$ | 26 | 27 | 14 | 15 |
| $\beta_h$ | 16 | 15 | 5 | 12 |
| $\alpha$ | 0.05 (0.09 fL/d and 0.03 pg/d) | 0.05 (0.09 fL/d and 0.03 pg/d) | 0.13 (0.20 fL/d and 0.07 pg/d) | 0.13 (0.20 fL/d and 0.07 pg/d) |
| $D_v$ | 0.014 (2.3 fL$^2$/d) | 0.015 (2.4 fL$^2$/d) | 0.017 (2.2 fL$^2$/d) | 0.013 (1.7 fL$^2$/d) |
| $D_h$ | 0.0014 (0.025 pg$^2$/d) | $2.7 \times 10^{-5}$ ($4.9 \times 10^{-4}$ pg$^2$/d) | $2.7 \times 10^{-15}$ ($10^{-14}$ pg$^2$/d) | $3.6 \times 0.019$ (0.34 pg$^2$/d) |
| Vc | 0.80 (72 fL) | 0.80 (72 fL) | 0.74 (59 fL) | 0.71 (56 fL) |

There were clear differences between the best-fit parameters derived for healthy individuals and those with anemia, and the different anemic conditions had different characteristic parameter sets. For example, healthy individuals and ACD patients have high $\beta_v$, and $\beta_h$ and low $\alpha$, i.e. they lost relatively more of their volume and hemoglobin during the fast phase than they did during the slow phase. In contrast, patients with TT and IDA lost relatively more volume and hemoglobin during the slow phase than in the fast phase. Patients with ACD showed slightly elevated $D_v$ and slightly reduced $D_h$ relative to healthy individuals, while TT was associated with a larger increase in $D_v$ along with a substantially reduced $D_h$. IDA patients had a $D_v$ similar to that of healthy individuals and showed dramatic elevation in $D_h$ with most individuals more than ten times higher than normal. The normalized critical volume, $v_c$, in healthy individuals and those with ACD was approximately 80% of $\bar{v}$, or about 72 fL. Most patients with TT or IDA typically had a reduced $\bar{v}$ and reduced $\bar{h}$. FIG. 2 shows that in addition to absolute reductions in $\bar{v}$ and $\bar{h}$, the $v_c$ for these patients was further reduced and showed much greater variability across different individuals.

Example 3. Predicting Iron Deficiency Anemia

This Example tested the hypothesis that compensated or latent IDA can be predicted in some cases at least 90 days earlier than is currently possible based on an expanding population of cells that project along the MCHC line closer to the origin than the mean. The projection operation is pictured in FIG. 5. The projected position (u) of each cell with volume (v) and hemoglobin (h) along the MCHC line was first determined:

$$u = v \cdot \cos\theta - h \cdot \sin\theta$$

$$\theta = -\tan^{-1}\left(\frac{\bar{h}}{\bar{v}}\right)$$

A threshold along the MCHC line was defined as a proportion ($\varphi$) of the average projected position $\bar{u}$: $\varphi \cdot \bar{u}$. The fraction of projected cells located between the origin and this threshold was then calculated as follows, where $f_{MCHC}$ is the probability density of the projected cells as a function of location on the MCHC line:

$$P_\varphi = \int_0^{\varphi \cdot \bar{u}} f_{MCHC}(u)\,du$$

Figure 8A:
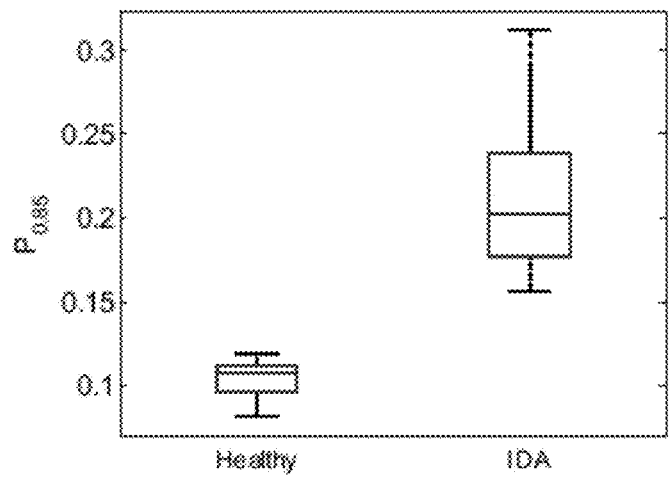
FIG. 8A is a boxplot showing the distributions of $P_{0.85}$ for the "Healthy" and "IDA" patients shown in FIG. 2. Based on these results, a threshold value for $P_{0.85}$ of 0.121 was selected for use in a test of an independent set of patients shown in FIG. 3D. This figure is an example of methods for identifying a threshold for latent IDA.
Figure 8B:
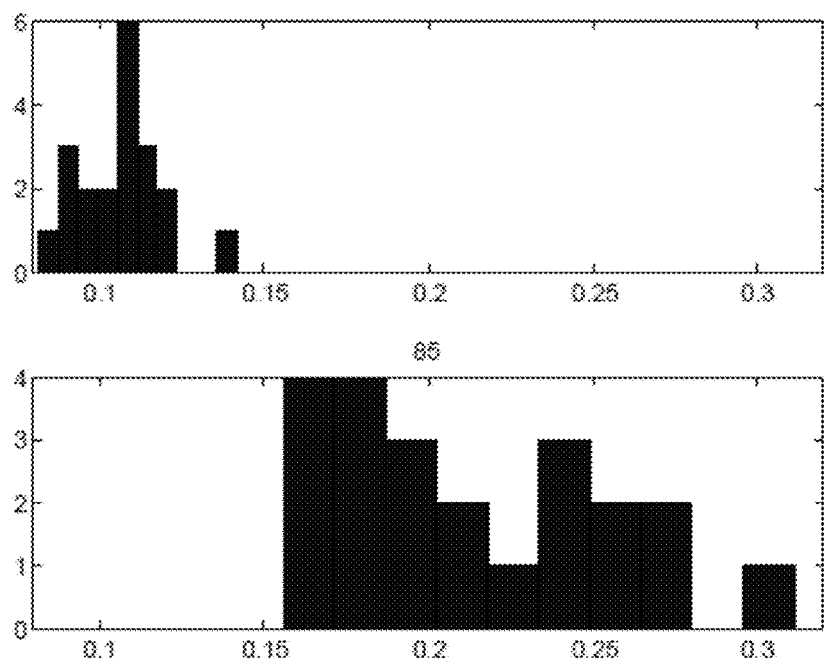

The $\varphi$=85% threshold was chosen by comparing the discrimination efficiency of different thresholds for the steady state CBCs used in FIG. 2. The 85% threshold shown in FIGS. 8A-B provided the greatest separation when compared to other thresholds (including 70%, 75% (shown in FIG. 8C), 80%, 90% (FIG. 8D), and 100%). A threshold value for $P_{0.85}$ of 0.121 was selected based on this training set.

40 new and independent patient CBCs, all of which were normal, were then identified. 20 of these normal CBCs came from individuals who had an additional normal CBCs 30-90 days later, and 20 of these normal CBCs came from individuals who presented with IDA no more than 90 days later. Patients with acute bleeding or any iron supplementation between the two CBCs were excluded. The definition of IDA is set forth above in Example 1. FIGS. 3A-D show that the threshold of 0.121 for $P_{0.85}$ was able to predict IDA with a sensitivity of 75% and a specificity of 100% in this independent test group.

Example 4. Differential Diagnosis of Microcytic Anemia

To assess the diagnostic accuracy of $D_h$ in differentiating the two most common causes of microcytic anemia, parameters were fit for 10 training cases: 5 with IDA and 5 with TT, as shown in FIG. 4. Case definitions are provided above in Example 2. The TT training set had $D_h$ ranging from $1.7 \times 10^{-15}$ to $2.3 \times 10^{-15}$. The IDA training set had $D_h$ ranging from 0.009 to 0.043. A threshold value equal to 0.0045, the average of the lowest $P_h$ among the IDA training set and the highest of the TT training set, was selected. 50 new and independent cases were then identified, 22 with IDA and 28 with TT. All 22 IDA cases were correctly classified, and 27/28 TT cases were correctly classified for an overall diagnostic accuracy of 98%. This accuracy is superior to that of 4 commonly cited discriminant functions (20): the Green & King formula yielded an accuracy of 92%, Micro/Hypo 84%, Mentzer 68%, and England & Fraser 57%. See reference (20) for further details on these other discriminant functions.

1. Fauci A S (2008) *Harrison's principles of internal medicine*/editors, Anthony S. Fauci . . . [et al.] (McGraw-Hill Medical, New York) 17th Ed pp v. <1-2>.

2. Donofrio G, et al. (1995) Simultaneous Measurement of Reticulocyte and Red-Blood-Cell Indexes in Healthy-Subjects and Patients with Microcytic Anemia. *Blood* 85(3): 818-823.

3. Gifford S C, Derganc J, Shevkoplyas S S, Yoshida T, & Bitensky M W (2006) A detailed study of time-dependent changes in human red blood cells: from reticulocyte maturation to erythrocyte senescence. *British Journal of Haematology* 135(3):395-404.

4. Waugh R E, et al. (1992) Rheologic Properties of Senescent Erythrocytes—Loss of Surface-Area and Volume with Red-Blood-Cell Age. *Blood* 79(5):1351-1358.

5. Willekens F L, et al. (2003) Hemoglobin loss from erythrocytes in vivo results from spleen-facilitated vesiculation. *Blood* 101(2):747-751.

6. Sens P & Gov N (2007) Force balance and membrane shedding at the red-blood-cell surface. *Phys Rev Lett* 98(1): 018102.

7. Willekens F L, et al. (2005) Liver Kupffer cells rapidly remove red blood cell-derived vesicles from the circulation by scavenger receptors. *Blood* 105(5):2141-2145.

8. Lew V L, Raftos J E, Sorette M, Bookchin R M, & Mohandas N (1995) Generation of Normal Human Red-Cell Volume, Hemoglobin Content, and Membrane Area Distributions by Birth or Regulation. *Blood* 86(1):334-341.

9. Zenker S, Rubin J, & Clermont G (2007) From inverse problems in mathematical physiology to quantitative differential diagnoses. *PLoS Comput. Biol.* 3(11):2072-2086.

10. Zwanzig R (2001) *Nonequilibrium statistical mechanics* (Oxford University Press, Oxford; New York) pp ix, 222 p.

11. Kampen N Gv (1992) *Stochastic processes in physics and chemistry* (North-Holland, Amsterdam; New York) Rev. and enl. Ed pp xiv, 465 p.

12. Lang K S, et al. (2005) Mechanisms of suicidal erythrocyte death. *Cellular Physiology and Biochemistry* 15(5):195-202.

13. Garner C, et al. (2000) Genetic influences on F cells and other hematologic variables: a twin heritability study. *Blood* 95(1):342-346.

14. Robbins S L, Kumar V, & Cotran R S (2010) *Robbins and Cotran pathologic basis of disease* (Saunders/Elsevier, Philadelphia, Pa.) 8th Ed pp xiv, 1450 p.

15. Milbrandt E B, et al. (2006) Predicting late anemia in critical illness. *Crit. Care* 10(1).

16. Rockey D C & Cello J P (1993) Evaluation of the Gastrointestinal-Tract in Patient with Iron-Deficiency Anemia. *N. Engl. J. Med.* 329(23):1691-1695.

17. Lozoff B, Jimenez E, & Wolf A W (1991) Long-Term Developmental Outcome of Infants with Iron-Deficiency. *N. Engl. J. Med.* 325(10):687-694.

18. Zarychanski R & Houston D S (2008) Anemia of chronic disease: A harmful disorder or an adaptive, beneficial response? *Can. Med. Assoc. J.* 179(4):333-337.

19. Jopang Y P, Thinkhamrop B, Puangpruk R, & Netnee P (2009) False Positive Rates of Thalassemia Screening in Rural Clinical Setting: 10-Year Experience in Thailand. *Southeast Asian J. Trop. Med. Public Health* 40(3):576-580.

20. Ntaios G, et al. (2007) Discrimination indices as screening tests for beta-thalassemic trait. *Ann. Hematol.* 86(7):487-491.

21. Lippi G, Salvagno G L, Solero G P, Franchini M, & Guidi G C (2005) Stability of blood cell counts, hematologic parameters and reticulocytes indexes on the Advia A120 hematologic analyzer. *J. Lab. Clin. Med.* 146(6):333-340.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
   measuring, using a hemanalyzer, a complete blood count (CBC) of a sample of red blood cells from a subject, a volume and a hemoglobin content of each red blood cell in the sample, and a mean corpuscular hemoglobin concentration (MCHC) of a population of the red blood cells of the sample;
   identifying that the subject does not have iron deficiency anemia (IDA) based on the CBC;
   transforming, using a suitably programmed computing device, the volume and the hemoglobin content of each red blood cell into an index by projecting the volume and the hemoglobin content of each red blood cell onto an MCHC line defined by the MCHC;
   determining, using the computing device, a sample percentage of the red blood cells is above a reference percentage, wherein, in a portion of the red blood cells corresponding to the sample percentage, the index of each red blood cell falls below a threshold location on the MCHC line, the threshold location corresponding to a percentage of a mean of the indexes of the red blood cells; and
   administering treatment for IDA to the subject who does not have IDA based on determining that the sample percentage is above the reference percentage.

2. The method of claim 1, wherein the threshold location corresponds to 70%, 75%, 80%, 85%, 90%, or 95% of the mean of the indexes.

3. The method of claim 1, wherein the reference percentage is about 10%, 11%, 12%, 13%, 14%, or 15%.

4. The method of claim 1, wherein the sample comprises whole blood from the subject.

5. The method of claim 1, wherein projecting the volume and the hemoglobin content of each red blood cell onto the MCHC line comprises performing a projection operation defined by $$u = v \cdot \cos\theta - h \cdot \sin\theta$$

$$\theta = -\tan^{-1}\left(\frac{\bar{h}}{\bar{v}}\right)$$

for each red blood cell, wherein $\bar{v}$ is a mean cell volume measured in the CBC, $\bar{h}$ is a mean cell hemoglobin content measured in the CBC, v is a volume of a red blood cell, h is a hemoglobin content of the red blood cell, and u is an index of a projection of the red blood cell onto the MCHC line.

* * * * *